(12) United States Patent
Aksit et al.

(10) Patent No.: US 12,263,066 B2
(45) Date of Patent: Apr. 1, 2025

(54) APPARATUSES, SYSTEMS AND METHODS FOR PERFORATING AND ASPIRATING INNER EAR

(71) Applicant: The Trustees of Columbia University in the City of New York, New York, NY (US)

(72) Inventors: Aykut Aksit, New York, NY (US); Jeffrey W. Kysar, New York, NY (US); Anil K. Lalwani, New York, NY (US); Daniel N. Arteaga, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 738 days.

(21) Appl. No.: 17/074,134

(22) Filed: Oct. 19, 2020

(65) Prior Publication Data

US 2021/0045925 A1 Feb. 18, 2021

Related U.S. Application Data

(63) Continuation of application No. PCT/US2019/028368, filed on Apr. 19, 2019.
(Continued)

(51) Int. Cl.
*A61B 17/3205* (2006.01)
*A61B 17/34* (2006.01)
(Continued)

(52) U.S. Cl.
CPC ...... *A61F 11/202* (2022.01); *A61B 17/32053* (2013.01); *A61B 17/3415* (2013.01);
(Continued)

(58) Field of Classification Search
CPC .. A61F 11/202; A61F 11/20; A61B 17/32053; A61B 17/3415; A61B 2017/00867; A61B 2017/320064; A61B 2017/3454; A61B 2217/005; A61B 10/0045; A61B 2010/0054; A61B 10/0266; A61B 10/04; A61B 2010/045;
(Continued)

(56) References Cited

U.S. PATENT DOCUMENTS 6,671,559 B2 12/2003 Goldsmith et al.
2003/0229322 A1 12/2003 Macrae
(Continued)

FOREIGN PATENT DOCUMENTS

WO 2015013120 1/2015
WO WO-2015200923 A2 * 12/2015 ......... A61B 10/0045

OTHER PUBLICATIONS

Karkas A et al. Benefit of Preoperative Temporal Bone CT for Atraumatic Cochlear Implantation Journal of Otology & Neurotology Mar. 2018—vol. 39—Issue 3—pp. 186-194.
(Continued)

*Primary Examiner* — Katherine M Rodjom
(74) *Attorney, Agent, or Firm* — BakerHostetler

(57) ABSTRACT

An apparatus for controlled perforation and aspiration of the inner ear having a distal portion including a plurality of apices and a plurality of valleys therebetween defining a plurality of serrated blades.

19 Claims, 31 Drawing Sheets

Related U.S. Application Data

(60) Provisional application No. 62/660,046, filed on Apr. 19, 2018.

(51) Int. Cl.
*A61F 11/20* (2022.01)
*A61B 17/00* (2006.01)
*A61B 17/32* (2006.01)

(52) U.S. Cl.
CPC ............ *A61B 2017/00867* (2013.01); *A61B 2017/320064* (2013.01); *A61B 2017/3454* (2013.01); *A61B 2217/005* (2013.01)

(58) Field of Classification Search
CPC . A61B 10/0233; A61M 5/3286; A61M 5/158; A61M 2210/0662
See application file for complete search history.

(56) References Cited

U.S. PATENT DOCUMENTS

| | | |
|---|---|---|
| 2006/0161255 A1 | 7/2006 | Zarowski et al. |
| 2010/0106134 A1 | 4/2010 | Jolly et al. |
| 2016/0331954 A1 | 11/2016 | Gibson |
| 2017/0172804 A1 | 6/2017 | Watanabe et al. |
| 2017/0239482 A1 | 8/2017 | Gibson et al. |
| 2017/0354434 A1* | 12/2017 | Guiles .................. A61B 17/322 |

OTHER PUBLICATIONS

Josephine Granna et al. Toward automated cochlear implant insertion using tubular manipulators, Proceedings of SPIE vol. 9786/ Issue 1 pp. F-1-F-8 Mar. 2016.

Tarasidis GS et al. Hearing Preservation After Penetrating Cochlear Injury. Annals of Otology, Rihonology & Laryngology vol. 126 / Issue 2 pp. 163-165 Nov. 2016.

Marco Caversaccio et al. Robotic cochlear implantation: surgical procedure and first clinical experience Acta Oto-Laryngologica vol. 137/ Issue 4 pp. 447-454 Feb. 2017.

B A. Mendis et al. Assistive surgical manipulator for cochlear implant surgery IEEE Xplore pp. 784-789 Mar. 2014.

International Search Report cited in PCT/US2019/028368, Oct. 24, 2019, 6 pages.

\* cited by examiner

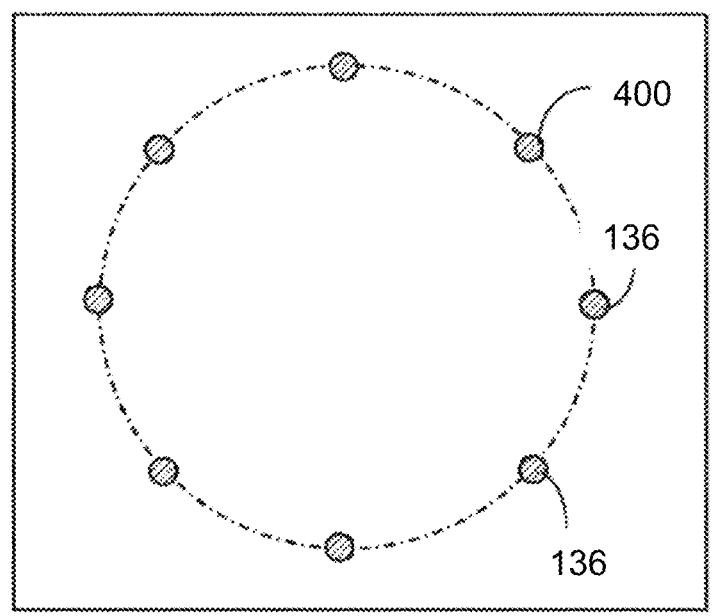
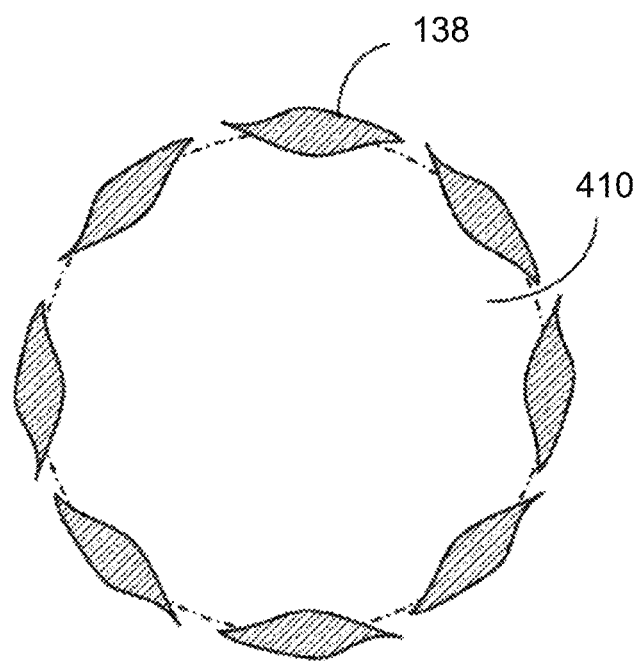
FIG. 9

FIG. 16
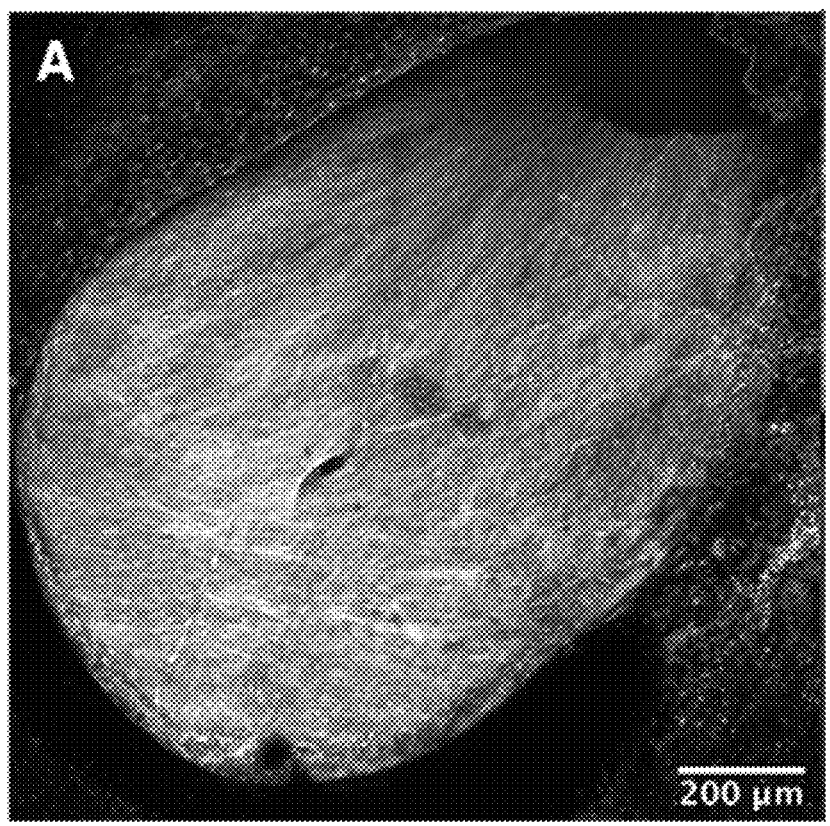
FIG. 17
FIG. 18
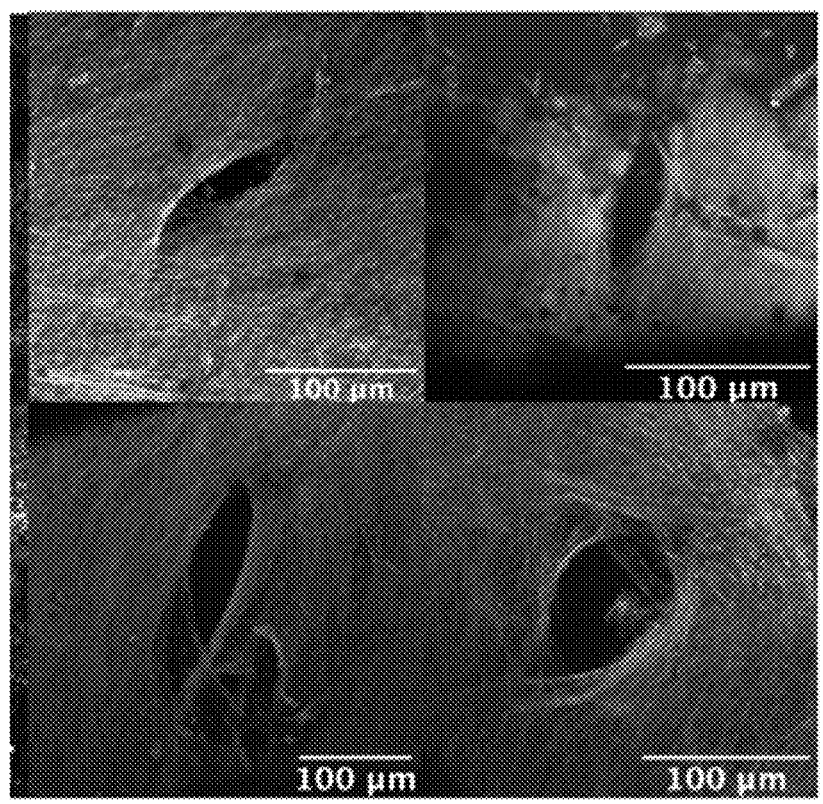
FIG. 19
FIG. 20

FIG. 22
FIG. 24
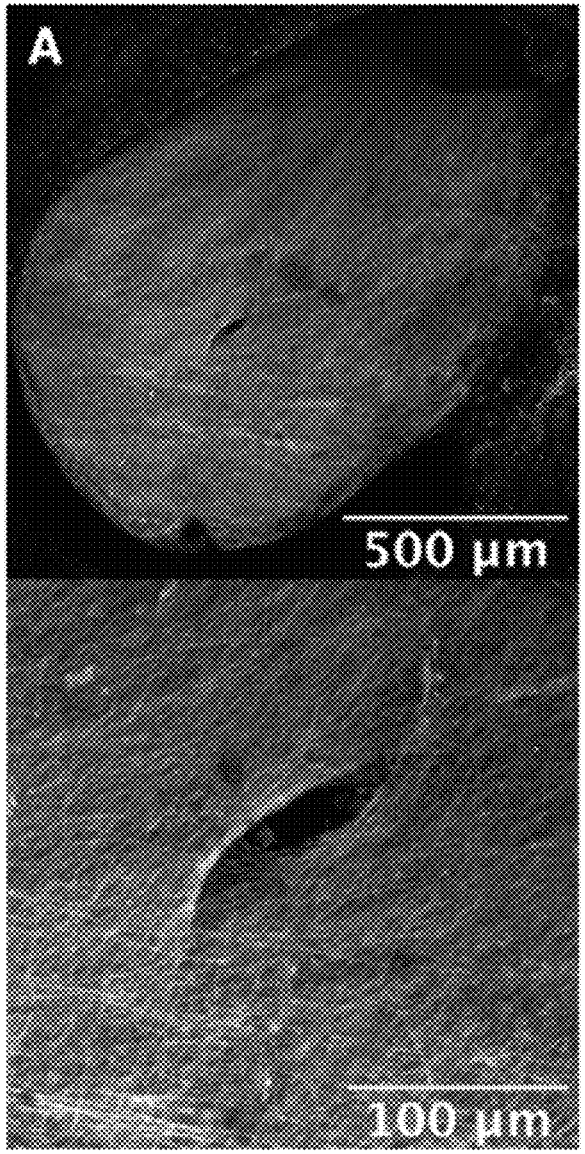
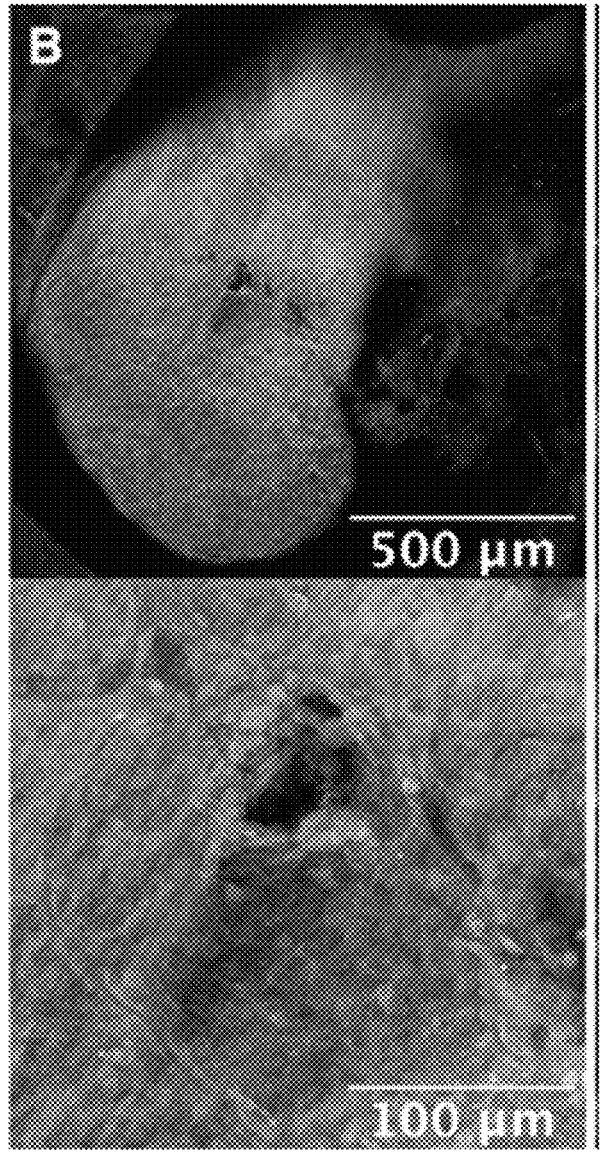
FIG. 23
FIG. 25

FIG. 27  FIG. 29

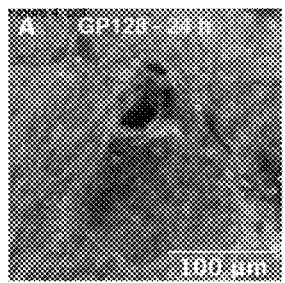 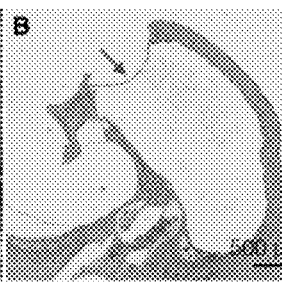 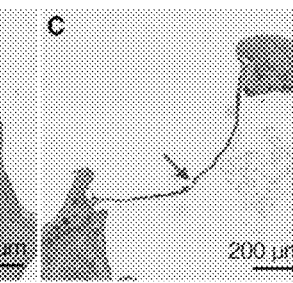 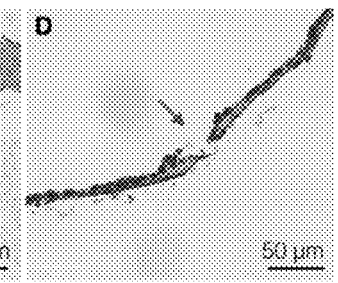
FIG. 30     FIG. 31     FIG. 32     FIG. 33
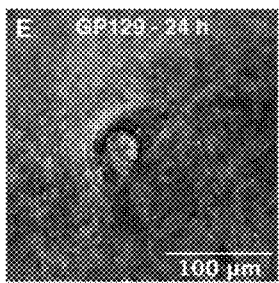 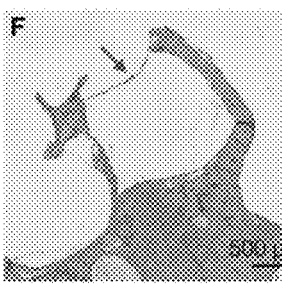 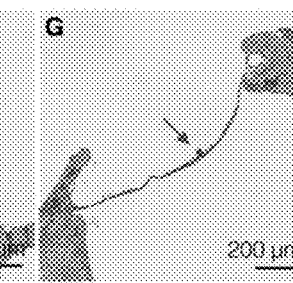 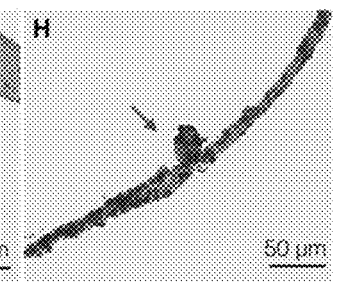
FIG. 34     FIG. 35     FIG. 36     FIG. 37

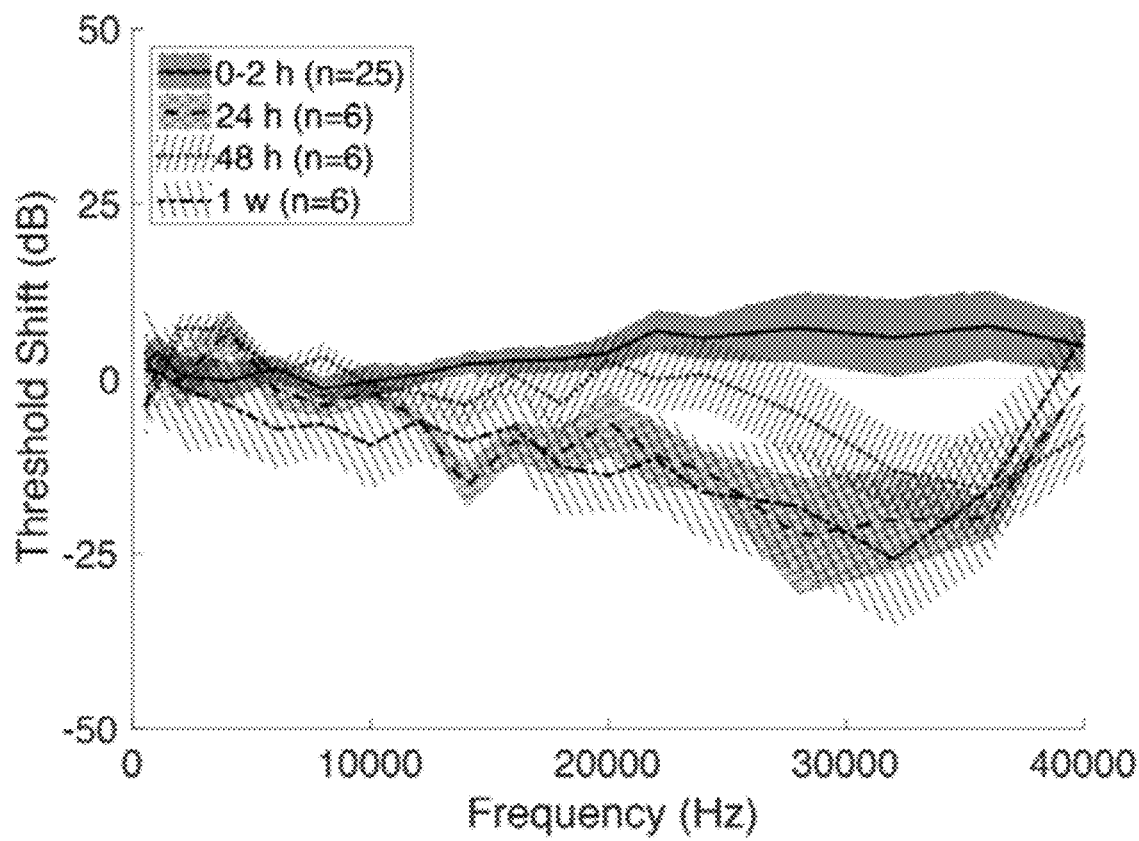
FIG. 38
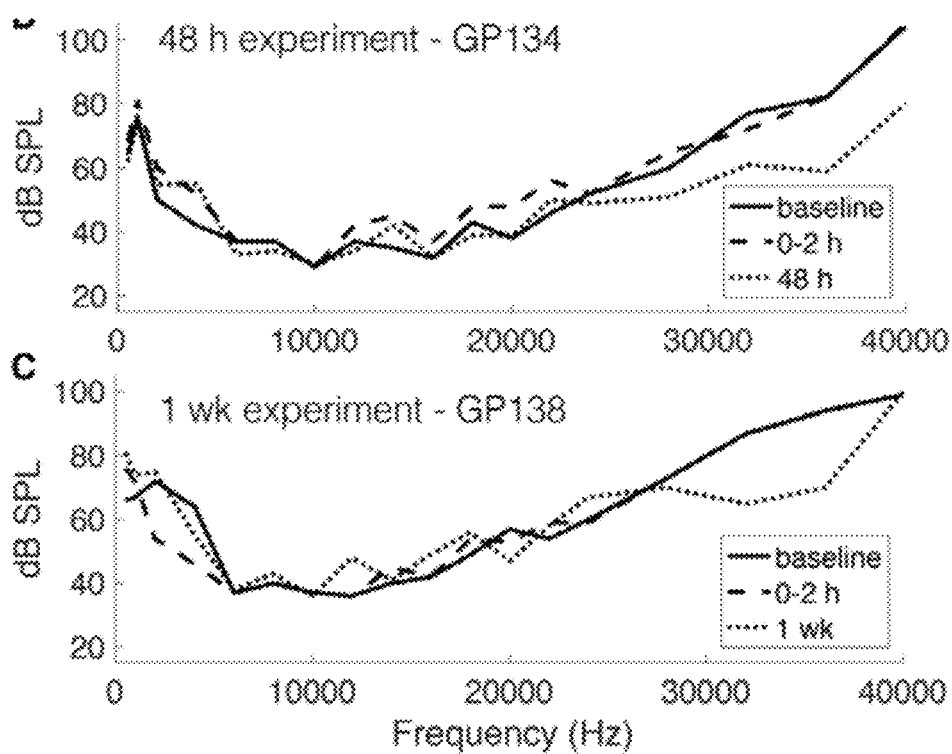
FIG. 39
FIG. 40

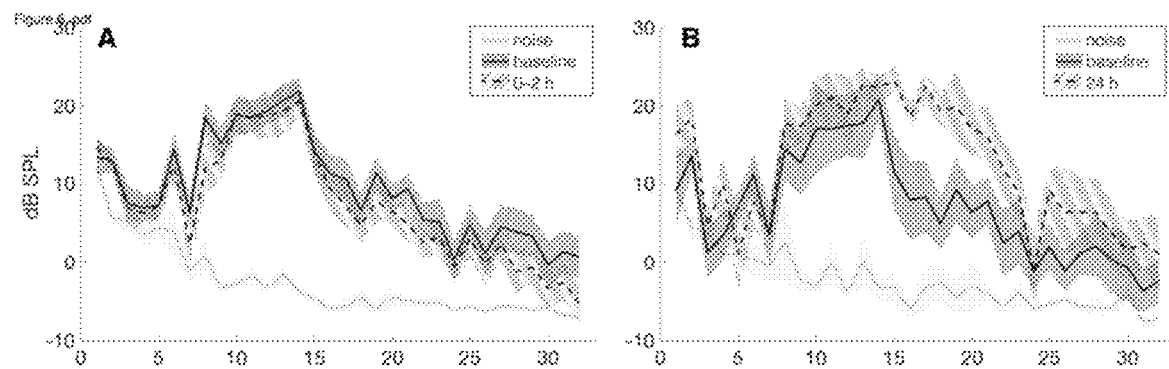
FIG. 41  FIG. 42
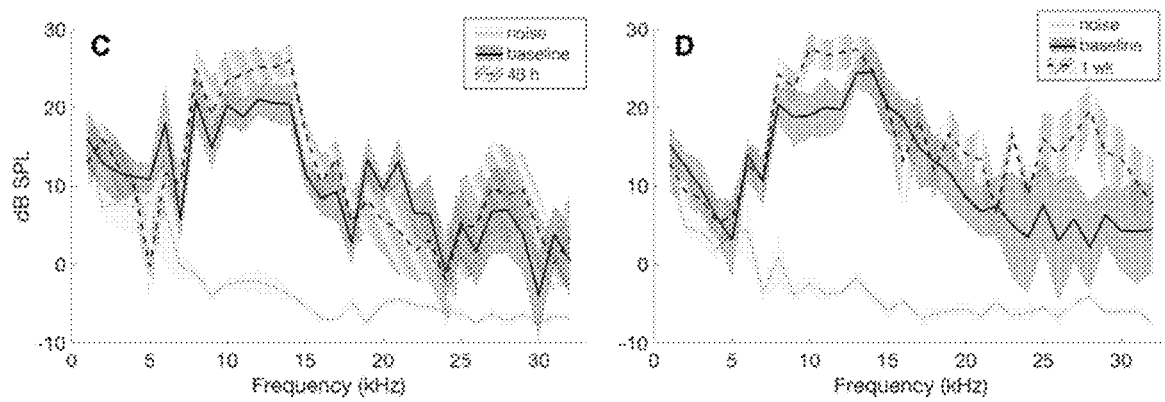
FIG. 43  FIG. 44

APPARATUSES, SYSTEMS AND METHODS FOR PERFORATING AND ASPIRATING INNER EAR

CROSS-REFERENCE

This application is a Continuation of International Application No. PCT/US2019/028368, filed Apr. 19, 2019, which claims priority to U.S. Provisional Application No. 62/660,046 filed Apr. 19, 2018, entitled "Apparatuses, Systems and Methods for Perforating and Aspirating Inner Ear," which are incorporated by reference in their entirety herein.

GOVERNMENT FUNDING

This invention was made with Government Support Under Contracts No. R01-DC014547; P30-CA013696; S10-RR025686 awarded by the National Institutes of Health. The government has certain rights in the invention.

TECHNICAL FIELD

The disclosed subject matter describes apparatuses, systems and methods directed to controlled precision of perforating a thin membrane in an inner ear. More particularly, the subject matter described is a punch device configured to produce a controlled and precisely shaped and sized perforation in a thin membrane of the inner ear. Further, the punch device apparatus may be configured to aspirate perilymph fluid from within the inner ear and introduce drugs to the inner ear.

BACKGROUND

The inner ear is a common site of pathology that can have debilitating effects on one's quality of life. Symptoms such as hearing loss, tinnitus, and vertigo are quite prevalent in the general population, and are frequently the cause of a patient's presentation to the physician. These symptoms, either alone or in combination with one another, can be reflective of underlying otologic disorders that necessitate specific medical or surgical intervention. Despite previous research and innovation, effective treatments for inner ear illnesses such as sudden sensorineural hearing loss (SSNHL) and Ménière's disease have remained particularly elusive. A major reason for the inability to precisely diagnose a patient is the current inability to perform specific diagnostics within the inner ear. This is due to the anatomic inaccessibility of the cochlea of the inner ear. As a consequence, the physician is often not able to determine the specific etiology of a patient's presentation, and thus is unable to target treatments for the individual cause. For example, over 70% of SSNHL cases remain idiopathic, while Meniere's disease is a clinical diagnosis of exclusion that typically takes 3-5 years of expensive testing and a worsening, often-permanent clinical presentation to reach. The treatments for these and similar diseases, meanwhile, are typically non-specific intratympanic steroids or ototoxic antibiotics because the exact cause remains unidentified. However, treatment with these drugs provide unproven efficacy in meta-analyses, and can harm the patient's current cochlear functioning.

Within the cochlea, the scala tympani and scala vestibuli are filled with a solution of fluid called perilymph. This solution is critical to the transduction of air vibrations into neural signals via the hair cells. When a patient has an acute or chronic illness of inner ear etiology, it is highly likely to be reflected by abnormalities in the chemical make-up of the perilymph, such as changes in the presence or concentration of various ions, proteins, bacteria, or viruses. Previous intra-operative studies on perilymph collection during cochlear implantation or tumor resection have allowed clinicians to differentiate disease etiology. During cochlear implantation surgery, an incision is created in the interface between the inner and middle ears, such as the round window membrane (RWM) to allow insertion of a tubular cochlear implant. In animal studies, methods of perilymph sampling have often utilized the creation of a basal or apical cochleostomy, requiring disruptive surgical drilling of the cochlear wall and putting the patient at risk for hearing loss.

The RWM and the oval window are entrances into the scalae and thus provide a promising portal for fluid aspiration of perilymph. Currently, clinicians employ devices and techniques developed for other purposes to enter the inner ear. Generally, a hypodermic needle is used to create an incision in the round window membrane or a myringotomy knife is used to create a slit or cruciform to make an opening large enough to insert an implant for both tympanostomy and cochlear implant. These methods create either a smaller hole (so that a cochlear implant insertion results in expanding the hole in the compliant membrane), or a larger hole (so that the leak is present or is closed somehow). Traumatic perforation inhibits effective membrane healing, and also contaminates perilymph samples with tissue fluid, blood, and cerebrospinal fluid (CSF) as perilymph is lost to the middle ear.

Conventional hypodermic needles typically have a bevel-cut tip to reduce the force required to penetrate the tissue of a patient's inner ear. During the penetration of a thin membrane with a hypodermic needle, the tip of the needle pushes the membrane causing the deflection until the tip causes a rupture of the membrane. The force applied to the membrane drops at the moment of the membrane rupture. Pushing the needle further into the membrane again requires increase of the force to create the hole and to push against friction until the shaft of the needle is in the membrane. During the course of this penetration process, the flexible membrane undergoes significant deformation. The diameter of the hole left in the membrane is a result of inelastic deformation and release of pretension of the membrane without any loss of the tissue. Therefore the diameter of the hole will not become the diameter of the needle and can't be controlled well. However, since the membrane is in pretension, there is a threshold needle size below which perforation will results in a stable opening and above which perforation will induce ripping in the membrane that will result in an opening larger than the needle. Needle design must be based upon this constraint.

Existing treatment of diseases affecting the cochlea, such as sudden sensorineural hearing (SSNH) loss and Meniere's disease, have been associated with inconsistent drug delivery and frequent side effects. Currently, the most common treatment for these disorders is intratympanic injection during which liquid glucocorticoid or gentamicin is delivered via needle and syringe through the tympanic membrane and into the middle ear. The injected therapeutic diffuses across the RWM and into the diseased cochlea. However, intratympanic (IT) dosing suffers from two flaws inherent to the technique. First, diffusion of drug into the cochlea depends on the time of contact between the therapeutic agent and the RWM. While contact is maintained when the patient is lying down, liquid therapeutic is inevitably lost via the Eustachian tube once the patient sits upright. Second, the rate of molecular transport across the round window membrane (RWM) itself is highly variable.

Therefore, there is a need for an apparatus that can create a precise, circular perforation in a thin membrane, aspirate perilymph from the inner ear without causing traumatic perforation of the membranes, as well as an apparatus useful for efficient and specific diagnoses of inner ear problems to allow for more personalized and targeted inner ear therapy. There is a further need for new tools to improve upon the existing IT dosing technique and to reduce the variability in drug delivery to the cochlea.

SUMMARY

The present disclosure provides enabled teachings of an apparatus and method for the atraumatic, precise perforation of a thin membrane and sampling fluid in the inner ear. The apparatus and methods for perforation and aspiration of the inner ear described in this disclosure aid clinicians to individualize inner ear diagnosis and treatment. Effective fluid analysis of the perilymph through various techniques, including liquid chromatography-tandem mass spectrometry (LC-MS/MS) can provide personalized and accurate diagnostics. Such analysis comes at a time when the amount of data describing gene expression and proteomics is rapidly growing.

According to an example embodiment of the inventive concepts disclosed herein, an apparatus designed for easy access to the thin membrane of the inner ear via an ear canal and middle ear space is provided. The apparatus perforates the thin membrane with minimal damage. In one example embodiment, the apparatus comprises a hollow tubular member having a proximal portion and a distal portion and a length there between. The distal portion includes a plurality of alternating apices and valleys forming serrated blades for precise circular perforation of a thin membrane of the inner ear, such as the round window membrane and tympanic membrane. The tip also comprises an inside bevel around its circumference. Notably, the inside bevel provides for capture of the plug of tissue cut from the membrane.

According to another example embodiment of the inventive concepts disclosed herein, the apparatus is an aspiration device capable of aspirating inner ear fluid precisely and efficiently. In this aspect, the tubular member may further include a proximal end adapted for connection to a vacuum or other suction means. In another example embodiment, the tubular member may include an aspirating force within its hollow tubular member. In some example embodiments the lumen formed by the hollow tubular member, at least at its distal end, may include a chamber, such as a small distal volume of the lumen. A pulse of negative pressure can be developed within the small volume inside the lumen to create an aspirating force.

In some non-limiting example embodiments, the apparatus includes a handle. The handle may have a curved tip made of medical grade stainless steel, whose dimensions are suitable for the anatomy of the ear. The apparatus may further include a stopper disposed proximal to the distal portion of the tubular member.

According to another exemplary embodiment, a method of treatment of the inner ear is disclosed herein, including providing a plurality of microperforations in the membrane of the inner ear; and injecting the region via intratympanic dosing adjacent to the microperforations with a drug formulation dissolved in a compound that undergoes gelification at human body temperature. In some embodiments, the method includes providing four or more perforations about 100 µm in size. In some embodiments, the compound is a hydrogel. In some embodiments, the hydrogel includes polaxamer 407. In some embodiments, the drug formulation is gentamicin.

According to another exemplary embodiment, a system for treating a membrane of the inner ear via intratympanic dosing is disclosed including at least one needle for providing a plurality of microperforations in the membrane; and a drug formulation dissolved in a compound that undergoes gelification at human body temperature. In some embodiments, the needle defines an outer diameter of about 100 µm (microns). In some embodiments, the membrane in the round window membrane (RWM). In some embodiments, the drug is gentamicin. In some embodiments, the compound is a hydrogel. In some embodiments, the hydrogel includes poloxamer 407.

In another non-limiting example embodiments, a method for manufacturing the apparatus is provided.

BRIEF DESCRIPTION OF THE DRAWINGS

A detailed description of various aspects, features and embodiments of the subject matter described herein is provide with reference to the accompanying drawings, which are briefly described below. The drawings are illustrative and are not necessarily drawn to scale, with some components being exaggerated for clarity. The drawings illustrate various aspects and features of the present subject matter and may illustrate one or more embodiment(s) or example(s) of the present subject matter in whole or in part. Together with the description, the drawings serve to explain the principles of the disclosed subject matter.

FIG. 9 is a depiction of crack propagation of a thin membrane caused by operation of an apparatus illustrated in FIG. 2.

FIGS. 16-20 are enlarged images of RWM perforated in vivo.

FIGS. 22-29 are enlarged images of RWM membrane healing following perforation in vivo.

FIGS. 30-37 are enlarged histological samples illustrating post-perforation sites following 24 hours of healing.

FIGS. 38-40 are plots illustrating auditory response using CAP following perforation.

FIGS. 41-44 are plots illustrating auditory response using DPOAE following perforation.

FIG. 45 is a perspective view of an apparatus in accordance with a non-limiting exemplary embodiment of the disclosed subject matter.

FIG. 46 is an enlarged view of the distal portion of the apparatus illustrated in

FIG. 47 is an enlarged view of the distal portion of the apparatus illustrated in FIG. 47, implemented in two sizes.

DETAILED DESCRIPTION OF THE DISCLOSED SUBJECT MATTER

The disclosed subject matter is directed to systems, methods and apparatuses that enable the easy and precise perforation of tympanic or round window membranes (RWM) of the inner ear of a subject to accommodate an implant, such as cochlear implant, or alternatively, to aspirate fluid from the inner ear or deliver drugs to the inner ear. The apparatus may also be used for tympanostomy. In addition, methods of manufacturing and using the apparatus are described.

In accordance with an example embodiment, an apparatus is described for making at least one perforation in a thin membrane of the inner ear such that the at least one perforation may have an optimal shape and size to accommodate a permanent or semi-permanent implant with minimal physical consequences to the inner ear. With respect to this aspect, FIG. 2 generally depicts an apparatus comprising a handle 200, a tubular member 100, a distal portion 120 and a stopper 110. The tubular member 100 is engaged to the distal end of a handle 200. The tubular member 100 comprises a proximal portion and the distal portion 120. The proximal portion may be secured to a handle (not shown). The stopper 110, which is separated apart and proximal from the distal portion 120 provides control of the depth of insertion of the tubular member 100 into the inner ear.

Figure 3:
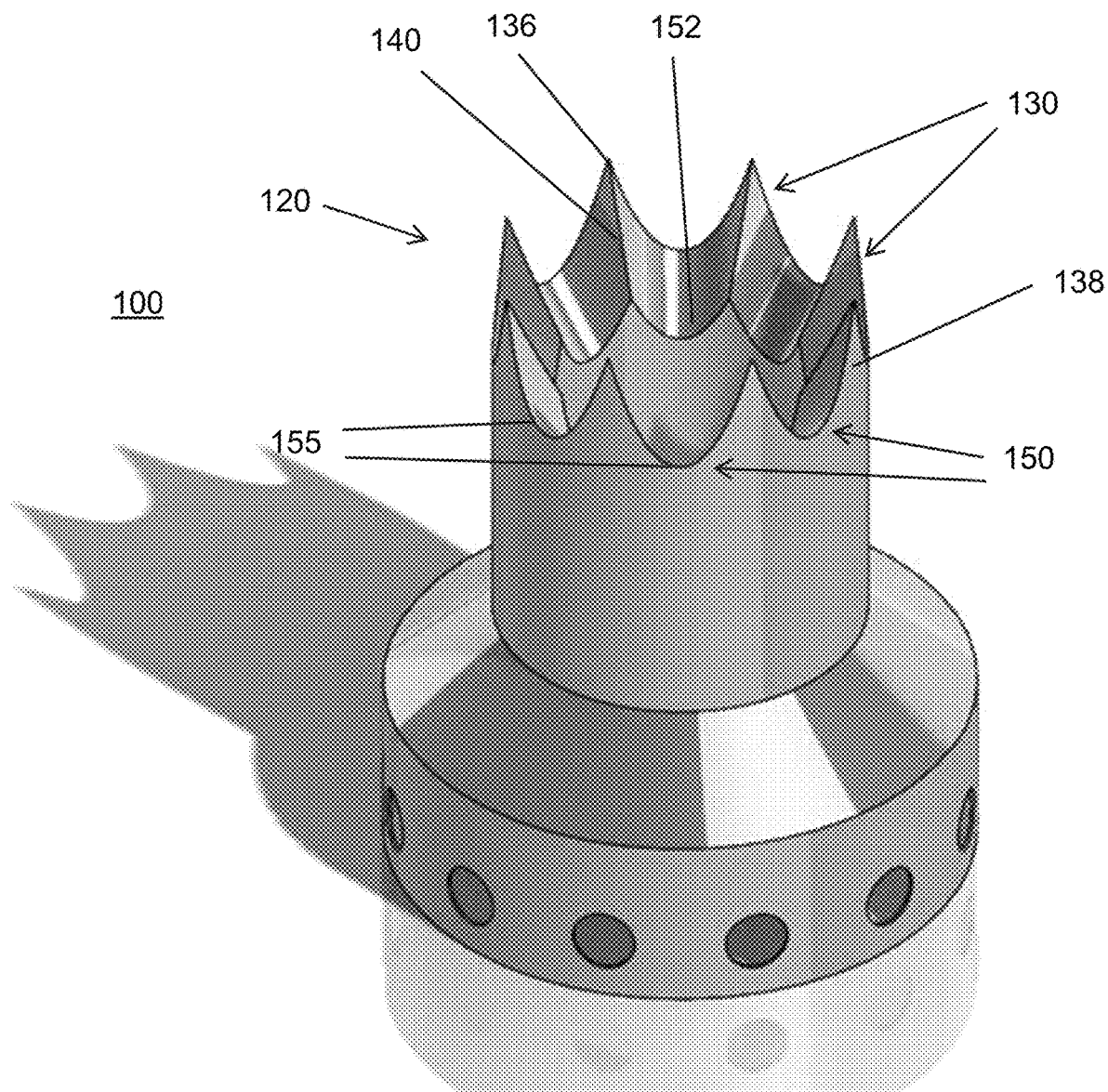
FIGS. 3, 4, and 5 are perspective views of the distal section (tip) of the apparatus illustrated in FIG. 2, in accordance with a non-limiting exemplary embodiment of the disclosed subject matter.
Figure 4:
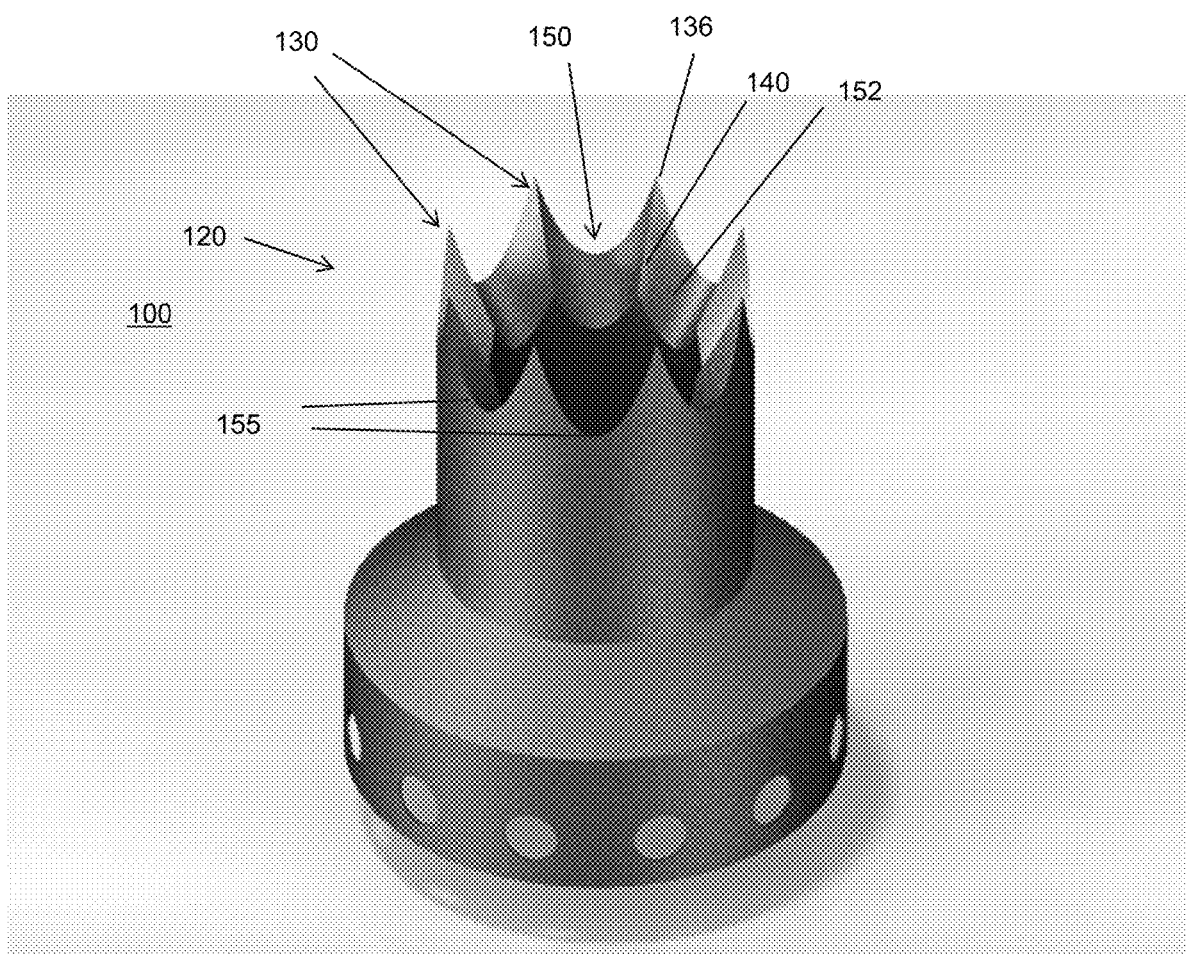

Next, referring to FIGS. 3 and 4, the distal portion 120 of the tubular member 100 is illustrated in detail The distal portion 120 includes a plurality of alternating apices 130 and valleys 150, which form a serrated blade at the distal end of the tubular member 100, wherein the distal portion 120 comprises an inside bevel around the circumference of the distal portion 120.

In an example embodiment depicted in FIGS. 3 and 4, the apices 130 may include a pointed tip 136 at the distal most end and a trailing edge 140. The trailing edge 140 extends proximally from the pointed tip 136 of the distal most end of the apices 130 to a valley 150. Thereby, forming a cutting blade. The valleys 150 include an arcuate edged surface 152 disposed between pairs of adjoining apices 130 that forms an inside bevel bounded by the cutting edges 140 and 155. The apices 130 and the valleys 150 formed by the inner surface of the distal portion 120 of the tubular member 100 constitute a continuous arris, or ridge formed by the meeting of the two surfaces at an interior angle, functioning as cutting edges.

In the example embodiment shown in FIGS. 3 and 4, the plurality of alternating apices 130 and valleys 150 form a plurality, e.g., eight, octagonal serrated blades 138. The pointed tip 136 and the trailing edge 140 may be configured in a sharp slender needle, which enables penetration of a desired membrane of an inner ear, for example, with minimal force. The arcuate bottom edge can be beveled sharply facing the inner cylinder of the needle such that the desired membrane may be readily cut along the line of the circle of the tubular needle, as shown in FIG. 9. The arris or ridge of the tip to the bottom edge serration is configured to maintain the sharp edge against the membrane to cut it efficiently. Thus, the distal portion of the tubular member 120 in some example embodiments has a crown shaped configuration. For ease of description, such needle tips are referred to herein as crown needles.

As depicted in the non-limiting exemplary embodiment of FIGS. 3 and 4, the beveled or serrated edges of the apices 130 extend proximally from a base portion of the distal portion 120 of the tubular member 100 to the pointed tip 136 of the apices 130. The apex or crown of the serrated tip is positioned radially outward at an angle from the inner diameter of the needle, providing an inside bevel. That is, the apex or crown shape formed by the apices 130 and the adjoining number of valleys 150 at the distal portion 120 of the tubular member 100 protrude radially outward away from a central axis of the tubular member 100 at an angle. Such configuration allows axis of the apices 130 at the distal portion 120, and central axis of the tubular member 100 to not be parallel to each other.

A non-limiting exemplary embodiment may comprise beveled or serrated edges that extend a distance of 2 mm (millimeters) from the pointed tip 136 of the distal most end of the apices 130 to a base portion of the apices 130. The apex 130 or crown of the serrated tip is positioned about 0.18 mm radially outward from the central axis of the tubular member 100. The serrated tip or edges may have an inner diameter of about 0.64 mm and an outer diameter of about 0.88 mm.

Also shown in FIGS. 3-4, the distal portion 120 of the tubular member 100 may further comprise a collar or flange 110 with a greater diameter than diameter of the distal portion 120. The collar 110 may serve as a stopper, as illustrated FIG. 2. The collar 110 contacts the desired membrane of the inner ear and prevents or avoids deep or unwanted penetration of the tubular member 100 into the inner ear. The collar 110 may also provide an engagement portion (not shown) that is configured to engage a complementary engagement portion of the major portion of the tubular member 100 so that the distal portion 120 is removably connected to the rest of the tubular member 100. The complementary engagement portions may comprise a screw fastener or a tongue and groove fastener, for example. Alternatively, the distal portion 120 may comprise the serrated inside-beveled tip that can be adhesively attached to the tubular member 100. As such, the distal portion 120 may be releasably engaged with the tubular member 100.

Figure 5:
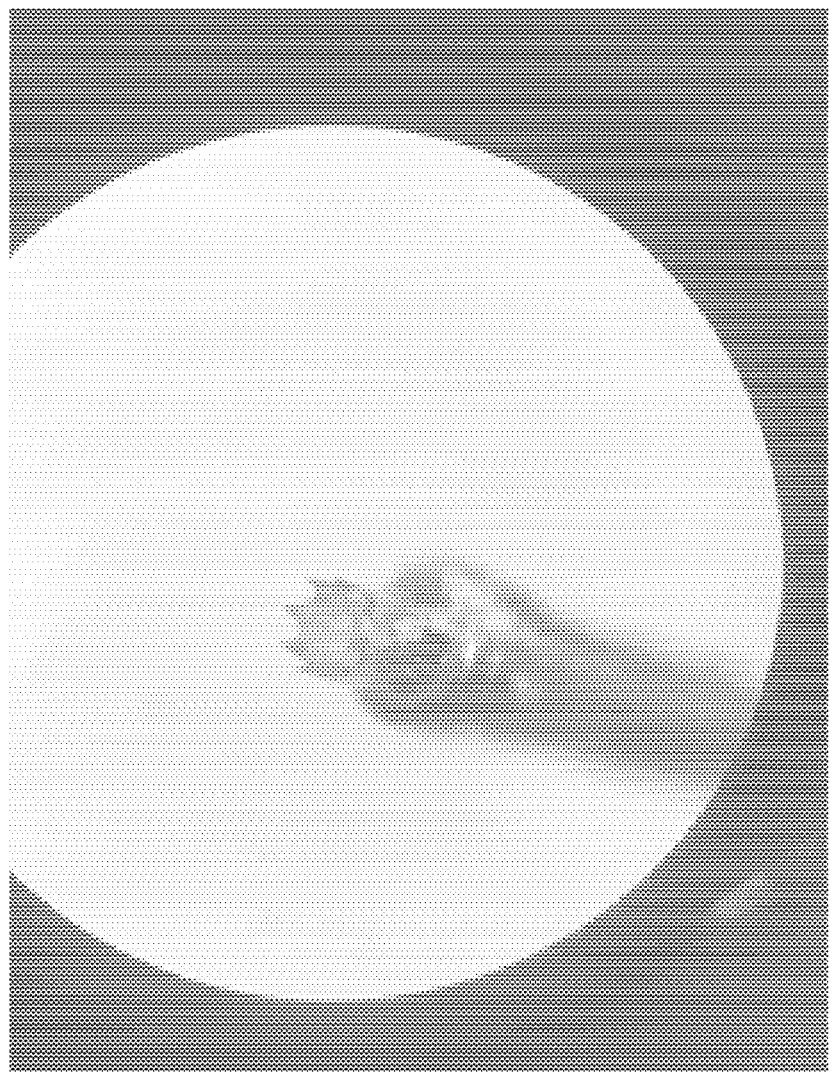
Figure 6:
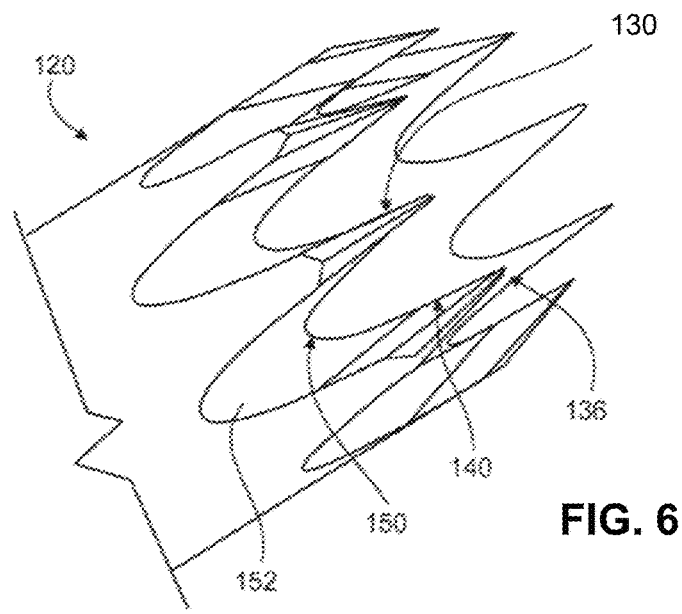
FIGS. 6 and 7 are perspective views of the distal section (tip) having an outside bevel of the apparatus illustrated in FIG. 2.
Figure 7:
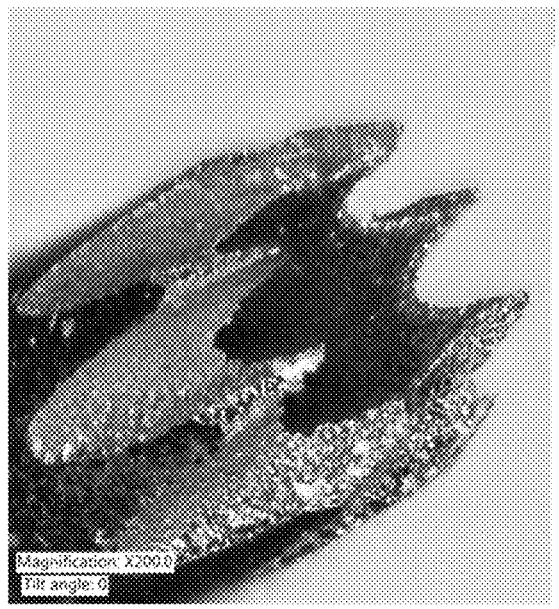

As used herein, the term "inside bevel" may refer to a bevel in which the face of the bevel is directed toward the interior of the tubular member 100. With an inside bevel, the outer surface of the tubular member 100 has a longer length than the inside surface of the tubular member 100, as shown in FIGS. 3-5. The term "outside bevel" may refer to a bevel in which the face of the bevel is directed toward the exterior of the tubular member 100. With an outside bevel, the outer surface of the tubular member 100 has a shorter length than the inside surface of the tubular member 100, as shown in FIGS. 6 and 7.

In some embodiments, the tubular member 100 may include an inside bevel angle of 15 degrees formed by the apices 130 and longitudinal length of the tubular member 100.

Figure 8:
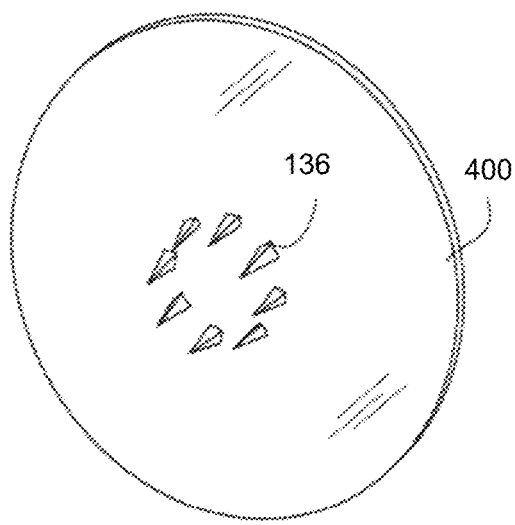
FIG. 8 is a bottom view of the tips of the apparatus penetrating a thin membrane.
Figure 10:
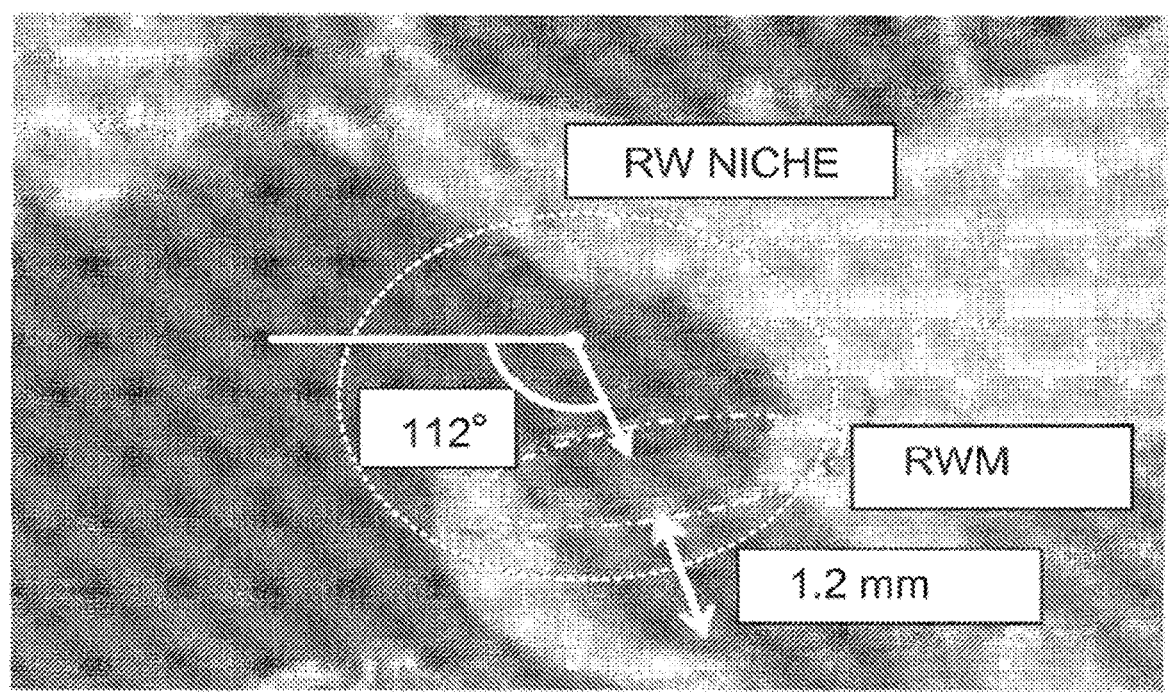
FIG. 10 is a micro CT scan image showing a round window niche and a round window membrane of a human cadaveric temporal bone.

As seen in FIG. 8, the tips 136 of the apices 130 penetrate the thin membrane 400 of the inner ear, for example, with minimal force application so that the deformation of the membrane can be minimized.

As schematically shown in FIG. 9, after penetration of the thin membrane 400 by tips 136, the blades perforate 138 the thin membrane 400, and a portion 410 of the membrane 400 is circumferentially disposed within the tubular member 100, and held in place by the plurality of apices 130. The thin membrane 410 is isolated from deformation of the membrane 400. As the distal end of the tubular member 100 is inserted deeper inside of the membrane 400 by increasing the force, the arris or ridges of the blades cuts the membrane 400 along the circular trace of the inner surface of the needle or the apices 130. Finally, as the arcuate bottom edges of the blades separates the thin membrane 410 inside apparatus from the remainder of the membrane 400, a hole which approximates the cross section of the inner circle of the tubular member 100 is left in the inner ear. The portion 410 of the membrane, e.g., RWM, that is severed by the serrated edges of the tubular member 100 can be captured and retained within at least one lumen of the tubular member 100. The at least one lumen may extend throughout the length of the tubular member 100. The inside bevel facilitates capture of this portion of the thin membrane 410 as a circular plug compared to previous tubular members comprising distal portions comprising outside bevels. The thin membrane 410 can be retained within the tubular member 100 and can be removed from the inner ear for analysis and diagnosis.

In other non-limiting example embodiments, depending on the tip configuration, only a portion of the RWM is severed to form a flap which maintains continuity with the remainder of the RWM via the unsevered portion. In other words, the cutting line does not circumscribe or extend completely around the needle tip. The flap may facilitate closure of the RWM following removal of the apparatus by providing a portion of membrane that can fill the hole and the edges of the flap and hole can heal together.

During this perforation of the membrane of the inner ear, the membrane undergoes significant deformation and deflection. However, the deformation within the region inside apparatus distal end will be minimized because the inside region will be pinned by the tips throughout the process. Therefore, the size and the shape of the holes or openings formed in the membrane 400 will be well-controlled predominantly by the shape of the tubular member 100, independent of the variability of the physical properties of the membrane of the individual patients as well as the technical variation of individual physicians. Although the apparatus is shown and described herein generally as having a circular cross section, other cross sections may also be contemplated, such as oval. In some example embodiments, the distal tip portion 120 may be configured to penetrate the membrane to form a slit that may more readily heal than a circular shape.

In an example embodiment, the tubular member 100 includes a stainless steel tube needle with ultra-thin wall, similar to a hypodermic needle, adapted with a plurality of alternating apices 130 and valleys 150 to form serrated blades extending distally from the tubular member. Although the non-limiting exemplary embodiment refers to eight octagonally-aligned serrations, it is understood that the needle or the distal portion 120 may be fabricated with a fewer or greater number of serrations, typically ranging from two to ten, with some embodiments having a number of, e.g., 3, 4, 5, 6, 7, 9, 10, 11, 12 symetrically-aligned serrations, while other embodiments may include even more serrations.

In example embodiments wherein a flap in the membrane is desired rather than a complete hole, one or more of the plurality of blades is absent and replaced with a gap or wider valley 150 without a cutting inside bevel edge in order to prevent cutting the membrane tissue in the locus where the gap engages the membrane. In a non-limiting exemplary embodiment, one of the sharp tips is absent, such that the octagonally inside-beveled needle is equipped with seven sharp points and one recessed wall section. A membrane that is penetrated by the seven sharp points followed by the cut at the arcuate bottom edges will still be attached at the locus where the recessed section of needle contacts the membrane.

Previous devices with outside bevels were prepared by a manufacturing method via wire electron discharge machining (WEDM). Wire electron discharge machining provides needles with the tubular member having an outside bevel, wherein the wire electron discharge machine cut lines can be made according to the plan shown in FIG. 6. FIG. 7 shows a microphotograph of a needle prepared by WEDM using the cut lines of FIG. 6. The photograph shows that the surfaces of the needle tip are somewhat rough at the microscopic level, leading to cutting edges that are not as sharp as desired. Such rough edges can result in undesirable tearing of the membrane instead of smoothly cutting the membrane.

Wire electron discharge machining cannot be used to prepare tubular members, or needles, with inside bevels. Furthermore, although WEDM can be performed on already manufactured commercially available hollow blunt needles, the sizes and tolerances related to the inside and outside diameters of the needle, as well as the material properties, are determined by the acquired needle.

A manufacturing method via two-photon polymerization (2PP) may be used to prepare the distal portion of the apparatus having an inside bevel. Ultra-high precision three dimensional (3D) molds can be made via 2-photon lithography, enabled by recent advancements in this technology. Two-photon lithography can be used to manufacture molds for making thermoplastic or metal distal tips as described herein.

Manufacturing precision needle molds using 2-photon lithography allows for direct manufacturing of needle tips with complex geometries or base structures for difficult-to-reach anatomic areas such as the RWM. Slanted or curved needles may also be manufactured using this method. These methods also permit a high level of resolution even at nanometer and micron level dimensions disclosed above. As a result, the distal tips described herein can include more sophisticated construction features than previous needles. For example, the outside diameter of the distal tip may be equivalent to or smaller than 31 gauge.

Since the precision of this manufacturing process may be very high, very smooth ultra-sharp needle distal portions can be made that are specifically engineered to reduce insertion force, thereby minimizing the damage to the membrane 400 and any surrounding tissue. Microscopic crown needles can be fabricated easily with desired geometries as necessary for different requirements, such as a specified tip diameter size, depth of penetration, bevel configuration and the like.

A simple and versatile fabrication process directly linking three-dimensional (3D) modeling and simulation with microscale printing and replication is described herein. The process involves micromolds fabricated by 3D stereolithography directly from CAD drawings, which are then used to provide shaped needles.

The molds can be used to fabricate polymeric needle distal tips by for example, press molding of epoxy, thermoset or thermoplastic materials. Direct 3D printing may also be used to prepare polymeric distal tips. Metal needle distal tips can be made using electrodeposition techniques.

The manufacturing process can be summarized as described below.

High precision 3D molds can be manufactured via multiphoton photolithography such as two-photon lithography. Other names for multiphoton photolithography include direct laser writing and direct laser lithography. In multiphoton photolithography, a mold precursor is transparent or substantially transparent to the wavelength of a light source so as to suppress single photon absorption relative to multiphoton absorption. The multiphoton absorption can cause a desired chemical change of the mold precursor. For instance, when the mold precursor includes or consists of a photopolymer, the multiphoton absorption can cause polymerization of the photopolymer and/or cross-linking of the photopolymer.

The fabrication method starts with manufacturing of the molds. For making metal needle distal tips, the molds are fabricated on a conductive substrate. Using the same order of magnitude feature sizes, the molds are made in the negative image of the desired needles by curing photoresist using two-photon lithography. The uncured photoresist is then stripped away by means of chemical treatment to leave cavities or voids in the mold. The substrate would then be left bare only at locations where the portions of the needles will be. For example, the distal tip(s) of the needle may be in contact with the conductive substrate. In other embodiments, the base of the needle is in contact with the conductive substrate.

The substrate needs to have a conductive surface to enable electrodeposition of metal. Every part of the conductive surface, except for the bare parts inside the patterned molds will need to be masked before being submerged into the electrolyte for electrodeposition. The mold-substrate assembly would then be submerged into an electrolyte and electrochemical deposition of metal would occur, filling the cavities or voids inside the molds, taking the shape prescribed by the voids.

After submersion, electrodeposition is conducted by flowing current or applying voltage to the system, growing the needles, tip-first, into the voids of the molds. The current density may be controlled by predicting the necessary current through mathematical models or keeping a constant voltage throughout the process.

After the molds are filled with metal, the molds can be stripped away by means of heat treatment or chemical treatment. The metal needles may be released as a final step by electropolishing or etching the underlying layer of material.

Hence, full metal needles will be manufactured in the shape of the voids inside the 3D lithographed molds, and this process in itself provides design freedom that is well suited and sometimes critical for a variety of applications. The needles can be slanted, curved or can take a shape necessary to conform to the necessities of the application in question. In particular, the needles comprise a plurality of alternating apices and valleys forming serrated blades and an inside bevel around their circumference.

Other suitable methods of filling the cavities include, but are not limited to, deposition and/or growth techniques such as chemical vapor deposition (CVD) or atomic layer deposition (ALD). These techniques are particularly useful when preparing microneedles with layers or shells comprising different materials. Since atomic layer deposition (ALD) can provide a coating with a thickness at the angstrom level, atomic layer deposition (ALD) is an example of a method that is suitable for preparing layers on the mold cavities having very small thickness levels. Atomic layer deposition (ALD) typically includes sequentially reacting different gas phase precursors with the surface of the mold cavities in a self-limiting chemical process. In some instances, the process is repeated in order to provide the shell layer with the desired thickness. Different shell layers can be formed using different deposition techniques or using the same deposition technique.

An alternative method for preparing the distal tips comprising applying a coating of an electrically conductive material to the interior surface of the mold cavity. In this way, the entire interior surface of the mold cavity is made conductive. Examples of conductive materials include metals such as copper, or compounds such as indium titanium oxide (ITO), titanium nitride (TiN), sometimes known as tinite, titanium carbon nitride (TiCN), titanium aluminum nitride (TiAlN or AlTiN), and titanium aluminum carbon nitride. These materials can be applied by physical vapor deposition (PVD, usually sputter deposition, cathodic arc deposition, electron beam heating, chemical vapor deposition (CVD) or atomic layer deposition (ALD). For example, copper can be applied using RF magnetron sputtering. A notable material is titanium nitride, an extremely hard ceramic material, often used as a coating to improve a substrate's surface properties. TiN is non-toxic, meets FDA guidelines and has seen use in medical devices such as scalpel blades where sharpness and edge retention are important. Titanium nitride may be applied by ALD.

Alternatively, such coatings can be applied to the distal tip after the molding described above.

Once the distal tips are prepared as described above, they may be mounted on sterile blunt syringe tips for practical use. For example, 23 gauge blunt tip syringe needles may be used as the main portion of the tubular member 100 of the apparatus. FIG. 5 shows a microphotograph of a needle tip mounted on the blunt end of a needle according to a non-limiting exemplary embodiment of the disclosed subject matter.

In accordance with another aspect of the disclosure, the apparatus is configured to aspirate fluid from the inner ear, e.g., perilymph aspiration. In this aspect, the apparatus described above can be configured with an aspirator to aspirate fluid from the inner ear after penetration of the inner ear membranes. The aspirator, for example, including but not limited to, may be a vacuum, suction or aspirating force engaged to the proximal end of the tubular member 100 or the handle 200. The vacuum, suction or aspirating force can be caused within the lumen of the tubular member 100 by creation of negative pressure.

The apparatus can both atraumatically perforate the human ear's RWM and subsequently aspirate samples of inner ear fluid, e.g., perilymph. The capability to sample perilymph from sufficient individuals can lead to the understanding of the presence or given concentration of a specific protein, ion, bacteria, or vial segment within the fluid which can be correlated to a patient's disease or risk factors. This information can lead to more personalized treatment plans, targeting the underlying etiology of each clinical presentation in a field that is currently wrought with ineffective treatments and ototoxic side effects.

For illustration purposes only, a non-limiting exemplary embodiment of the apparatus can be formed having an outer diameter of 0.25 mm and an inner diameter of 0.1 mm at the proximal end. The apparatus can include a flange or collar 110 disposed at the intersection of the proximal end of the tubular member 100 and the base of the tip having a first and second wedge shaped configuration forming dual-needles wherein the bevel is an inside bevel. The flange can be formed with an outer diameter equal to the outer diameter of proximal portion. In some example embodiments, the flange or collar 110 can be configured with a greater outer diameter so as to protrude or extend radially outward from the proximal portion of the needle. The flange 12 can be formed having a flat or planar surface at the distal, or axial, end thereof. The frictional forces generated between the flange and the RWM upon operation of the apparatus grabs the RWM and pushes or deflects the RWM downward. The larger diameter of the flange (relative to the distal crown needles) also serves as a plug which sealingly engages the border of the opening formed in the RWM, thereby ensuring that all fluid within the RWM is captured and aspirated through the lumen of the needle without any leakage externally of the needle.

In a non-limiting exemplary embodiment, dual-blade tips are formed having points comprising angles of ten degrees. However, alternative angles can be sized as so desired and are considered to be within the scope of the present disclosure. Moreover, the dual-blade tips can be formed with varying angles along their respective lengths to provide a contoured needle point, if so desired.

To promote healing after penetration, the dual blade needle and an elliptical cone positioning system are provided such that the flat blade tips cuts the RWM parallel to the direction of the collagen fibers (in the major axis direction of the elliptical membrane). In effect, the cutting operation disclosed herein severs the cross-linking between adjacent fibers rather than severing through the fiber itself. Cutting the RWM in this direction is advantageous in that it reduces the force needed for RWM penetration while also minimizing damage to the membrane's nano-scale collagen architecture. After the apparatus is removed, the scar shape is a line without any removal of the tissue. Furthermore, the surface tension can easily close a micro-hole formed in accordance with the present disclosure, facilitating the healing process after the aspiration.

To ensure precise penetration of the RWM without any contact of the needle to inner ear structures such as basilar membrane, a statistical approach can be applied to optimize the length of the blades and apparatus. Further, the apparatus may include a stopper to contact the membrane and control the extent of penetration into the inner ear. To access the RWM through the ear canal, the apparatus is designed to be small and flexible. The size can allow for simultaneous endoscopic visualization, to observe the insertion of an aspirator into the outer and middle ear space.

Figure 11:
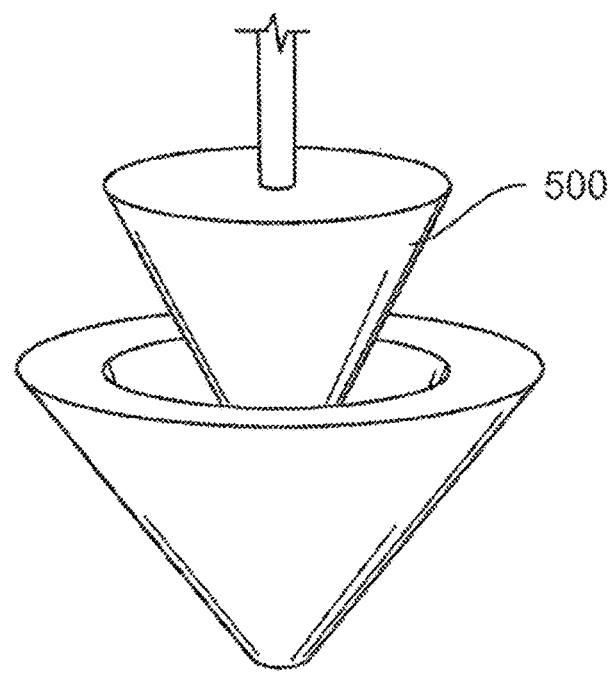
FIG. 11 is a schematic view of a non-limiting exemplary embodiment of a guide member for use with an aspirating tubular member in accordance with the disclosed subject matter.

Furthermore, to enable precise positioning above the optimal region of the RWM, micro CT scan data of the bony niche can be used to design a guide member, e.g., jig 500 as shown in FIG. 11. As the round window niche and RWM faces vertically from the outer ear, visually positioning a needle or apparatus is virtually impossible. The guide jig 500 allows manual positioning by a surgeon, and is optimized to fit the bony niche snugly. The funnel shape of guide member enables guidance toward a targeted spot on the RWM. The guide jig 500 can be formed with different size jigs to work with different size niches.

Alternatively, the proximal tip can be molded with an integrated guide member shaped to conform to a portion of the round window niche of the subject, so that proper alignment with the RWM can be achieved.

Additionally, or alternatively, sensors and/or an optical scope can be provided to monitor the location and displacement of the needle and RWM during deployment of the needle. In other example embodiments, an expandable device (not shown), e.g. balloon, can be employed as the guide member similarly to the guide jig 500 described above for precisely guiding the needle to the desired location. Use of a balloon can be particularly advantageous in that it can conform to the unique geometry of the patient, thereby ensuring a proper fit and accurate placement of the needle. In some example embodiments, the expandable guide member can be formed from a self-expanding shape-memory material such as nitinol which exhibits martensitic and austenitic properties. Furthermore, the apparatus can be formed with a steerable, or articulating, tip so that the distal tip of the needle can be oriented perpendicularly to the RWM while the remainder of the deployment apparatus may be angled as necessary to position the device within a patient's anatomy.

In a non-limiting exemplary illustration of the operation of the apparatus, the tip of the apparatus is oriented at the midpoint of the RWM using any of the guide member features discussed above. The needle is located at the midpoint of the RWM as this location will allow the greatest amount of deflection of the RWM, and thus the greatest amount of perilymph aspiration due to this compression or reduction in volume. As the tips of apparatus penetrate through the RWM, the perilymph fluid is aspirated through the lumen within the lumen of tubular member of apparatus 10. That is, the RWM can act as a diaphragm to pump the perilymph solution into the lumen as the tip of tubular member is pushed downward or into the RWM. The tubular member of apparatus can be formed with multiple lumens, with certain lumens dedicated for proximal flow (e.g. aspiration) and other lumens dedicated for distal flow (e.g. delivery of therapeutic agents) into the patient. Thereby, different lumens may be involved in different functions. To facilitate the aspiration of the perilymph solution into the needle, the inner surface of the needle lumen can be coated with a lubricant to reduce the capillary forces which can inhibit fluid transfer.

The proximal end of the tubular member can be coupled to a chamber or reservoir for collecting the aspirated fluid. For example, a 10-cm (centimeter) hose can be coupled to the lumen of tubular member 100 in which the hose extends outside the patient so as to be visible to the physician/operator and has a length/volume that equates to a predetermined amount of perilymph fluid. During operation, the operator can confirm that the desired amount of fluid has been aspirated by visually observing that the hose is completely filled. Additionally or alternatively, the collection chamber or reservoir can have graduations that enumerate the amount of fluid contained therein. In some embodiments, the collection chamber or reservoir is removably coupled to the tubular member 100 or the handle 200 and includes a closure, e.g. cap. After aspiration of the perilymph solution the collection chamber can be detached from the needle and closed for transport or subsequent processing.

In operation, to detect RWM penetration, an ion sensitive electrode with nano-scale coating of Ag/AgCl may be provided that can detect the chloride concentration change that comes from contact with the perilymph. Aspiration, meanwhile, can be assessed with a two-ring system equipped at the end of the catheter that continuously measures the impedance. A change from air to solution during aspiration is readily detected. Aspiration can be accomplished through spontaneous capillary action, assisted by the elastic energy stored within a displaced RWM. Essentially, after penetration the RWM acts as a diaphragm pump using this stored energy to send perilymph solution to the exit with the least fluidic resistance. The pressure necessary for fluid to enter the needle can be analyzed by applying Poiseuille's law:

$$\Delta P = \frac{8\mu L Q}{\pi r^4} \quad (1)$$

The pressure OP necessary to carry 1 μL (micro-liter) of Newtonian fluid, with viscosity of μ=0.001 Pa*s, through a tube of radius r=100 μm (micro-meter), at the volume rate of Q: 0.01 mm$^3$/s=1 μL/100 s, is 25.4 Pa (Pascal). Conversely, the experimental data of the penetration of the guinea pig RWM as well as computer simulation via ABAQUS predicts the displacement of the RWM and the resulting pressure within the inner ear to be up to 100s of μm and 10 kPa (kilo Pascsal). The RWM will relax and lose elastic energy as the perilymph solution is displaced into the catheter. Even at the moment of aspiration when we detect the sampling of the 1 μL of perilymph, the final pressure is expected to be well above 25.4 Pa. Therefore, the penetration and deformation of the RWM itself will store enough energy to drive perilymph through the catheter system. Additionally, the purity of the perilymph obtained can be assessed, meanwhile, by measuring its potassium or lactate dehydrogenase concentration. Their intracellular contents are high, and could be significantly affected by trauma to surrounding tissues or CSF contamination.

The apparatus described herein provides for quick, precise and minimally traumatic sampling of perilymph solution via a round window membrane (RWM) for the diagnosis of inner ear disease. To perforate RWMs with minimal trauma, the mechanical anisotropy was considered. The mechanical properties of the round window membrane (RWM) are thoroughly analyzed and disclosed with the use of nanoindentation, bulge testing, and microCT, as disclosed in PCT/US13/75105 and U.S. Provisional Application No. 61/981,458, the entirety of each is hereby incorporated by reference. Additionally, it has been discovered that most human tissues show anisotropy for functional and developmental reasons, with the collagen fibers of RWMs run in the direction of its major axis. The present disclosure also provides a biometrical study using μ-computed tomography to determine the size and variability of the human middle/inner ear anatomy. For instance, the human bony niche provides a narrow entrance (1 mm) to the RWM (2.5~3 mm).

In a dual tip needle embodiment, from a side view, the tips, each form one symmetrical wedge to sever a RWM parallel to the underlying collagen fibers so that the incision is linear, rather than round. To allow sampling, a 31G tubular member can be used for minimal hydrodynamic resistance.

Accordingly, a hollow tubular apparatus is provided that has the dual objectives of allowing atraumatic insertion into the cochlea through the RWM and subsequent aspiration of a consistent perilymph volume promptly.

Although described herein for penetrating the RWM, the device described herein can be used to penetrate other membranes in a subject's body where small well-defined holes are required. For example, the apparatus or tubular member 100 can be adapted for use in other areas such as ophthalmology where creation of precision holes is necessary.

Example 1

The apparatus is assembled with a micropipette for sampling perilymph solution of a guinea pig cochlea in vitro. The sampled solution is analyzed via UV-vis spectroscopy to confirm the existence of proteins.

Materials and Methods: Design of a Dual Wedged Needle

To design a needle optimized for the creation of a minimally traumatic hole, the mechanical properties of the RWM was taken into account. Unlike the name may suggest, the RWM has an oval shape in a plan view and is woven with nano-meter scale collagen fibers. These fibers run parallel to the major axis of the oval resulting in the property called anisotropy. This anisotropy is the mechanical property describing that the RWM is stronger in the major axis orientation than in the minor axis. Consequently, a perforation with a regular round needle tends to be an asymmetric oval shape. To take advantage of this anisotropy, a needle of the present disclosure makes a linear incision along the direction of the collagen fibers to reduce the energy of perforation and consequently minimize the trauma to facilitate subsequent healing process. The standard anatomical terms of location are used to define the direction. In the frontal plane view, the needle has a distal portion comprising two linear blades with inside bevels. In the longitudinal plane view, these two blades are aligned in the center of the needle making the shape of one symmetrical wedge. The two linear blades are intended to sever the collagen fibers parallel to them and open the linear incision by the wedge to allow for making a hole with minimum size necessary for the aspiration of the perilymph solution.

To realize prompt aspiration of perilymph solution at negligible small pressure, fluid dynamics was considered and the dimension of the needle is determined as follows. Smaller sizes of the needle diameter are less atraumatic to the RWM. However, the time necessary for the aspiration increases as the inner bore diameter become smaller. When a 31 gauge needle is used for aspiration, the pressure necessary for fluid to enter the needle can be estimated by applying Poiseuille's law, given in Equation 1, where the pressure AP necessary to carry 1 μL of Newtonian fluid, with viscosity of μ=0.001 Pa*s, through a tube of radius r=100 μm, at the volume rate of Q: 0.01 mm$^3$/s=1 μL/100 s, is 25.4 Pa (=2.5 mmH2O). This dimension will provide negligible hydrodynamic resistance for the aspiration of perilymph solution.

$$\Delta P = (8\mu L Q)/(\pi r^4) \qquad \text{Equation 1}$$

The angle of the wedge is minimized for the small force penetration to the extent in which the tip does not make any contact to the inner ear wall or basilar membrane. A micro CT scan image (SkyScan 1172; Bruker microCT, Belgium) of a human cadaveric ear can be used to map the dimensions needed for the apparatus to penetrate the RWM. A fresh temporal bone was purchased (Science Care, Phoenix, AZ) and drilled to optimize the resolution of the scan. The distance between the RWM and the basilar membrane was estimated to be 1.2 mm. Therefore, the length of the wedge was determined to be 0.6 mm such that the wedge has enough sharpness to penetrate a RWM.

In some example embodiments, a tubular member 100 according to the present disclosure meets the following anatomical criteria related to the distal portion: length limit of about 1.2 mm to prevent or avoid inner ear damage; a curved aspiration canal system: a bendable/flexible tube. In some example embodiments, a needle according to the present disclosure meets the following mechanical property criteria: Anisotropic strength of RWMs: penetration of a RWM in a weaker direction; Minimal size of an incision to minimize the damage to a RWM. In some example embodiments, a tubular member meets the following fluid dynamic criteria: A few to 60 seconds aspiration-negligible fluidic resistance. In some embodiments, a tubular member according to the present disclosure meets the following anatomical criteria: Wedge length of about 0.6 mm; Stopper at about 1.0 mm from the distal portion 120; A flexible gauge 30 polyimide tube. In some example embodiments, a tubular member 100 according to the present disclosure meets the following mechanical property criteria related to the distal portion: Sharp linear wedge shape (tip radius of curvature 2 μm or less); Size of the needle: about 0.14×0.256 mm. In some example embodiments, a tubular member according to the present disclosure meets the following fluid dynamic criteria: 31 gauge needle: 256/128 μm outer/inner diameter.

Figure 1:
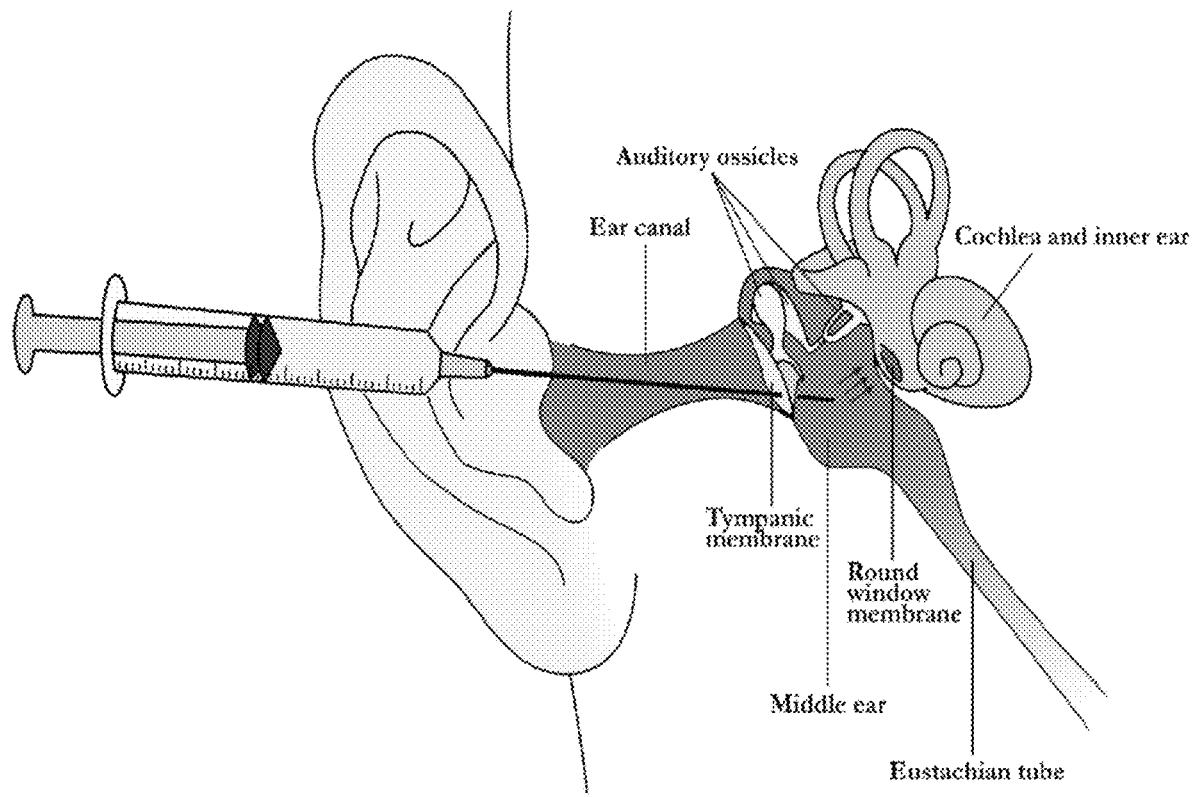
FIG. 1 is a cross-sectional view of prior art surgical procedures in the inner ear.
Figure 2:
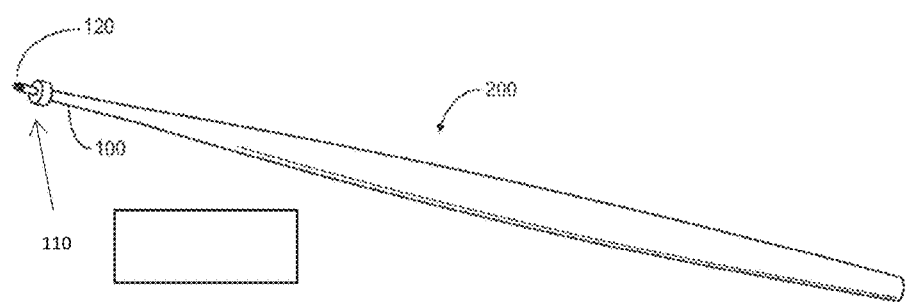
FIG. 2 is a perspective view of an apparatus in accordance with a non-limiting exemplary embodiment of the disclosed subject matter.

As in the example embodiment of FIG. 2, the aspirating tubular member can include a stopper or a physical mark to determine when to stop insertion of the tubular member in the ear. In the longitudinal plane, proximate the wedge portion of the tubular member, a 0.4 mm length sliding stopper is provided. This "slide and stop" region of the tubular member provides a stop point of penetration and start point for sampling of fluid. This region can be larger than the inner diameter and thinner than the outer diameter of the tubular member such that the perforation in the RWM becomes narrower.

In Vitro Demonstration with a Guinea Pig Cochlea

Guinea pig cochleae may be used for demonstration. The size of the RWM and the volume of the cochlea of guinea pigs are much smaller than those of humans. Therefore, the demonstration in this smaller size may provide a strong case for concluding that a larger sized human RWM will be less traumatic than the results in this study.

Guinea pigs with no history of middle ear disease are euthanized under pentobarbital anesthesia according to IACUC at Columbia University. Within 10 minutes after euthanization, both cochleae are harvested. The cochlea bones are trimmed by drilling to remove the bone hanging over the RWMs and to ensure the passage of the needle yet with minimal damage to the canals of the inner ear. The cochlea bones are fixed on a petri dish filled with saline solution providing moisture. And, the dual blade needle is lowered slowly with the control of micromanipulator. The penetration of the RWM is confirmed with a binocular microscope. The needle is lowered until the wedge is lowered below the membrane completely. The micropipette attached to the dual wedge needle is used to aspirate 1 μL of perilymph solution. After the aspiration, the dual wedge needle is retracted. The aspirated perilymph solution is ejected to 39 μL of saline solution in a microcentrifuge tube.

Immediately after the sampling experiment, the inner ears are fixed in 10% neutral buffered formaldehyde solution overnight. The detail of dehydration process for scanning electron microscopy is described previously. Briefly, after dehydration using ethanol, critical point drying is performed with hexamethyldisiloxane. After coating of gold, scanning electron microscopy is performed to determine the shape and size of the incision.

UV-Vis Absorbance Spectroscopy of Sampled Perilymph Solution for Protein Analysis To demonstrate the analysis of protein in the perilymph and confirm the success of sampling biological solution, the sampled perilymph solution is analyzed via UV-Vis absorbance spectroscopy using a plate reader Synergy 4 (Biotek®, VT). The solution is kept temporarily in a microcentrifuge tube and mixed with a vortex mixer. The 20 μL solution is transferred to a Corning® UV plate flat bottom for 96 wells and additional 20 μL saline solution is poured. The plate reader procedure is 30 second shake followed by absorption spectroscopy of UV and visible light (200~800 nm). The concentration of protein mixtures is roughly estimated by Equation 2 where X: the concentration (mg/mL), A: absorbance, and L: path length (cm). Path length of the specimen is calculated as 0.63 mm by dividing the volume of 40 μL by the surface area of the bottom from the diameter of 6.35 mm. The ratio of the dilution is taken into account.

$$X = A/L \qquad \text{Equation 2}$$

An assembled apparatus has an adapted needle for sampling perilymph using a micro-pipette at the proximal end of the apparatus for suction. A polyimide tubular member disposed between the micro-pipette and adapted needle is used for flexibility and tight fit with the dual wedge needle. In this study, an oversize stainless steel tube is put on over the polyimide tube to stabilize the needle during the penetration of the guinea pig RWM. FIGS. 14B and 14C show detailed views of the tip of a needle according to the present disclosure.

Linear Incision in the Guinea Pig RWM

The moment of initial penetration is easily confirmed when the RWM pops up by the spring-back-action of the RWM. Further penetration is terminated visually at the stopper 110 of the needle. Each hole may have a flattened oval shape. All of the RWM keeps the integrity intact except for the oval hole. The average major and minor axis diameter may be about 320-380 and 120-170 μm Pearson's r between the major and minor diameter is 0.4. These two types of values suggest that the size of hole varies with small geometrical similarity, with aspect ratio of about 0.4-0.43 with standard deviation of 6.7%. Typically, the hole expands as great as 5 times in both major and minor axes when a round needle penetrates the RWM of a guinea pig.

The Concentration of Protein in the Perilymph Incision

Absorbance spectroscopy of the sampled perilymph solution can be compared with that of saline solution. The subtraction curve of the two curves in the wavelength range of 240 to 320 nm. Can be used to show a difference that suggests the presence of protein. The subtraction curve may show peaks of at or about 205, and 270 and 280 nm (nanometer).

The flexible tubular member can be useful for embodiments in which the sampling tube needs a curved canal. In this embodiment, the tubular member can be formed from material with suitable flexibility such as polyimide and other polymers with similar durometer. When a needle is inserted through an external ear canal, the RWM does not face perpendicular to the angle of these approaches. Thus, some embodiments have a curved shape close to the tip in order to approach and penetrate the RWM vertically against it. Like tools such as a Rosen needle that has the curve at the tip, this flexible polyimide tube enables embedding in the canal system for aspiration.

Precise and Quick Sampling

The 31 gauge needle used in some embodiments has small enough fluidic resistivity to aspirate 1 μm of perilymph solution within a few seconds with great accuracy. This fluidic resistivity provides enough room to further improve the atraumacity of perilymph sampling. In addition to the precise control over the volume of the perilymph sample, minimizing intrascalar pressure is also critical for atraumacity of the inner ear structure. Some complications that can be caused by intracochlear pressure change are suggested in the cases of cochlear implantation, Meniere's disease or barotrauma experienced by divers. While minimizing the volume of perilymph solution removed alone will reduce the risk of physical damage caused by the pressure, slowing down the aspiration will likely minimize the pressure and the risk as well.

The volume of the human scala tympani is on the order of a 44 μL. Thus, 1.0 μL of perilymph removal is 2.2% of the entire volume. The scala tympani is connected to the entire inner ear through helicotrema and the partially sealed cochlea aqueduct next to the RWM communicates moderately with cerebrospinal fluid. The fluidic conductance through these routes is limited and the dynamic pressure grows proportionally to the fluidic resistance and the speed of fluidic flow. Although, the rate of the perilymph flow rate in a healthy human individual is not yet known, the flow rate of a guinea pig is 0.001 to 1 μL/min. Therefore, some embodiments have a pressure, flow rate, and volume control system to slow down the aspiration speed from 0.3 down to 0.01 μL/sec. Further, this aspiration method may be validated with an intrascalar pressure sensing experiment. Lastly, these systematic approaches will also evaluate possible contamination from the cerebro spinal fluid to ensure the high quality sampling of perilymph solution.

Atraumatic Sampling: Force Required to Penetrate, Shape of the Hole

Larger holes seen in a RWM than the holes contemplated being formed by the apparatus disclosed herein in are known to heal spontaneously within a few days without significant damage to hearing. The results herein demonstrate that a needle of the present disclosure is capable of leaving incisions of an oval shape with the minor axis diameter smaller than the diameter of a 31 gauge needle. A healthy RWM is under pretension and, without proper care, penetration can rip the hole causing catastrophic rupture and resulting in complete loss of the RWM. The consistent size and shape of the perforation demonstrates that the sampling via the prototyped needle minimizes such a risk. The human RWM has much larger size than a guinea pig. Thus, penetrating a human RWM using a needle disclosed herein has better chances of minimizing the trauma due to structurally stronger human RWM ("HRWM") than a guinea pig RWM.

Molecular Analysis of the Sampled Perilymph Solution

The protein constituents of the sampled solution can be analyzed and identified via liquid chromatography-mass spectrometry. In guinea pig model, by independently identifying the protein constituents of perilymph from the apex of the cochlea and CSF from spinal cord, we can quantify the proportion of perilymph and CSF.

A tubular member 100 having a dual wedge tip or more complex structures can be fabricated using 2PP as described herein. The tubular member 100 can be fabricated with high quality, i.e. excellent sharpness at the tip as well as smooth surface. A precise aspiration can be provided in conjunction with a micropipette, or other device causing an aspirating force to suction of vacuum the fluid from the inner ear. Perilymph can be sampled from a cochlea while leaving a controlled oval perforation.

The devices and systems described herein can be used for in-office diagnosis via sampling of perilymph solution. An effective sampling method of the perilymph through the RWM will greatly ameliorate the current proteomic analysis of the contestants for diagnosis and facilitate more directed approaches to treatment. Moreover, medications can be specifically targeted to the faulty outer hair cells typically associated with SSNHL, while leaving other parts of the inner ear undamaged. The growth of new hair cells in mammals can be induced through the inhibition of the Notch signaling pathway. Once the etiology and pathophysiology of a given patient's presentation is understood, the specific affinity properties of carrier materials may be used to target tissues, cell-specific receptors/promoters, or the restricted biochemical reactiveness of proteins in cells. This provides the foundation for molecular therapy for inner ear disorders. An atraumatic, precise approach to perilymph sampling provides the basis for effective fluid analysis through various techniques, including liquid chromatography-tandem mass-spectrometry (LC-MS/MS). Such analysis allows the amount of data describing gene expression and proteomics to rapidly grow.

However, prior tools used to sample the perilymph solution for diagnosis have not been optimized for the patients to outweigh the benefit of perilymph sampling over risk associated to the operation. During major surgeries for cochlear implantation or tumor resection, previous studies for perilymph collection was performed intra-operatively using a glass capillary. A diagnosis must be performed without any major surgery. The use of a fragile glass capillary has the risk of failure of the tool as well as the extended duration of sampling due to the slow process of the capillary action. In animal studies, methods of perilymph sampling have utilized the creation of a basal or apical cochleostomy, requiring disruptive surgical drilling of the cochlear wall and putting the patient at risk for hearing loss. Alternatively, the round window membrane (RWM), is the membranous entrance into the perilymph-filled scalae of the cochlea, provides a promising portal for fluid aspiration that can heal spontaneously. As a matter of fact, there is no other route than through the ear canal, middle ear and the RWM where a physician can have access to the inner ear space without causing permanent damage to a patient. The tools of the present disclosure that facilitate to aspirate the perilymph solution during exploratory tympanostomy tremendously reduce the risk for a patient and improve the quality of diagnosis based on molecules in the inner ear fluid.

In another exemplary embodiment microneedles are disclosed herein. Microneedles facilitate IT injection, which utilizes diffusion across the RWM to deliver therapy without manipulating cochlear anatomy. Microperforations of the RWM, which can be provided by microneedles as described herein, can both increase the rate of diffusion and offer greater control over inner ear drug levels, as discussed below. The microneedles disclosed herein are durable and can safely create precise perforations in the RWM in vivo that heal within one week and have minimal effect on hearing.

Microneedles for Perforation of the RWM

Figure 21:
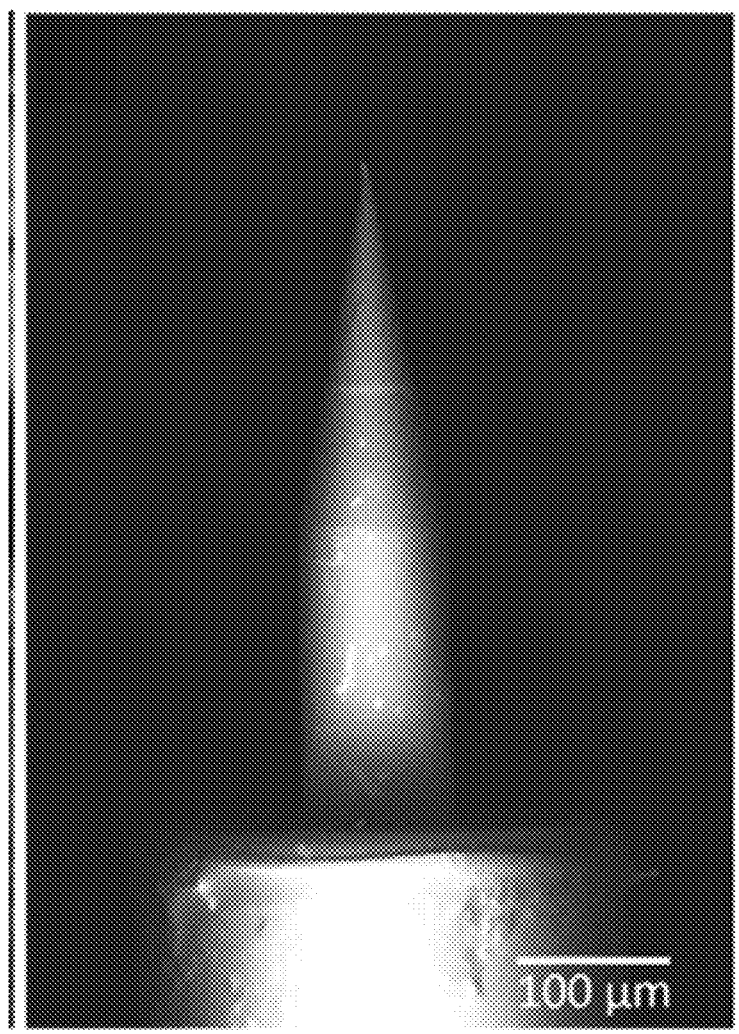
FIG. 21 is an enlarged image of the apparatus in accordance with the exemplary embodiments of the disclosed subject matter.

The microneedles were fabricated using two-photon polymerization lithography by Photonic Professional GT system (Nanoscribe GmbH, Karlsruhe, Germany). The photoresist employed was IP-S (Nanoscribe GmbH). Each microneedle had a diameter of 100 µm, length of 150 µm, and an ultra-sharp tip with a tip radius of curvature of 500 nm, designed specifically to perforate the RWM of a guinea pig. The needle shafts were constructed with varying angles from vertical, including 0° and 30°, to accommodate variation in RWM surgical access. The needles were mounted to the ends of 30 gauge, blunt, stainless steel syringe needles (Howard Electronic Instruments, El Dorado, Kansas) using commercial epoxy resin. Mounted needles were sterilized with ethylene oxide gas prior to survival surgeries. Microneedles used for the perforation of the guinea RWM are illustrated in FIG. 21 (after use) and are substantially identical, except for the dimensions discussed herein, to the microneedle apparatus 700 illustrated in FIGS. 45-47.

Figure 12:
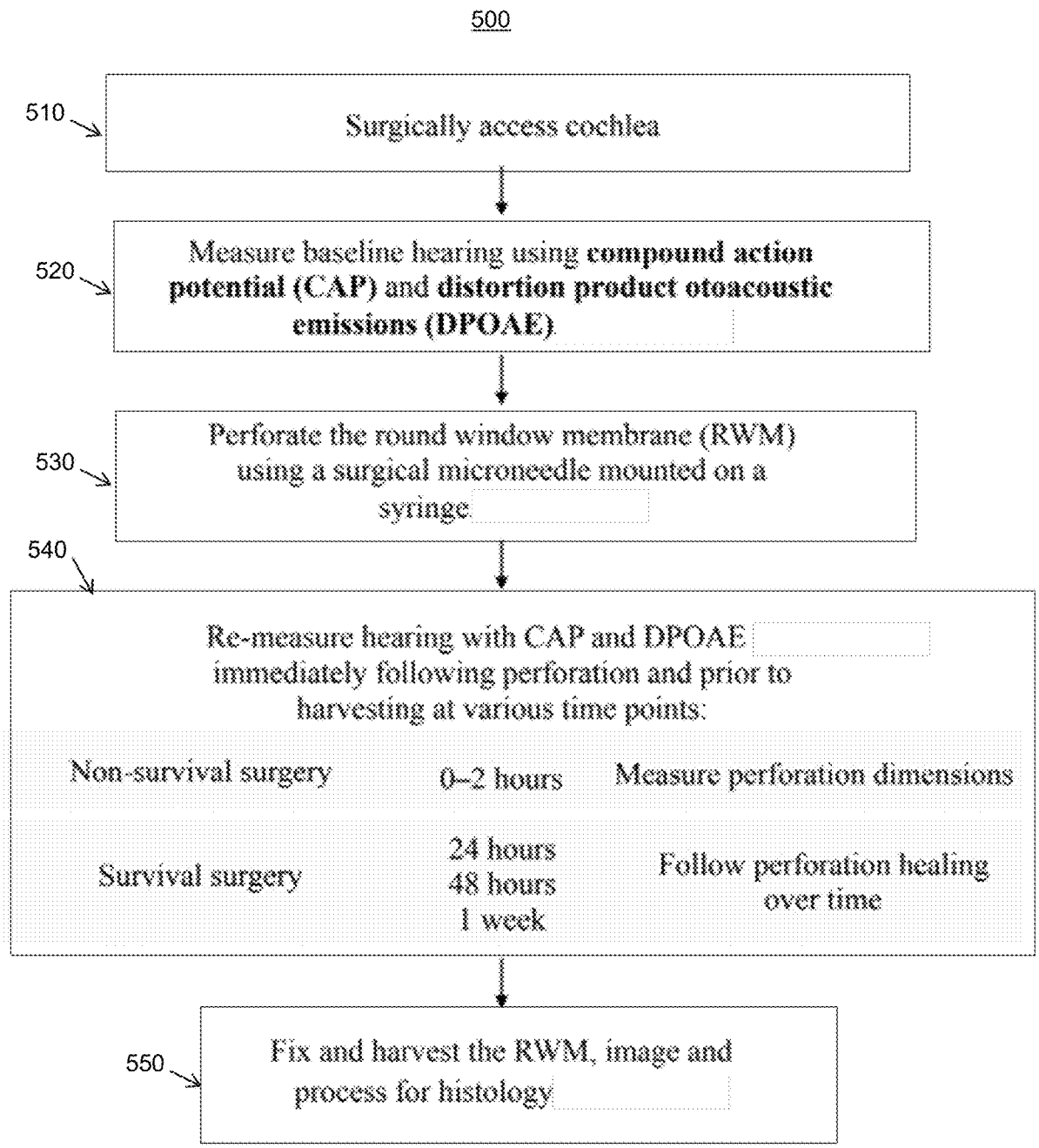
FIG. 12 is a flow-chart illustrating a surgical procedure in accordance with an exemplary embodiment.
Figure 13:
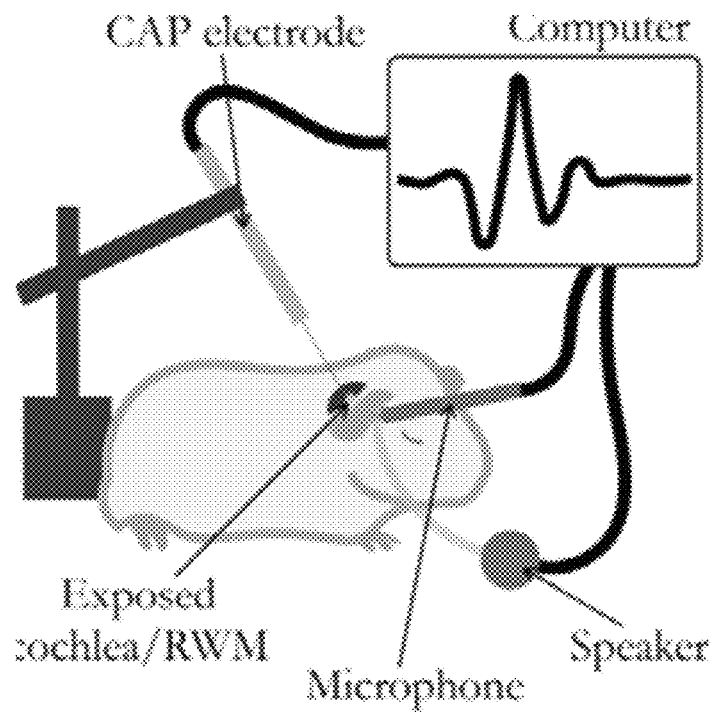
FIGS. 13-14 are schematic diagrams illustrating the surgical procedures and apparatus discussed regarding FIG. 12.

Twenty-seven adolescent guinea pigs (Hartley strain) weighing 200 to 400 grams and age 1-6 weeks were obtained from a commercial vendor (Charles River, Inc., Massachusetts). As illustrated in FIG. 12, each guinea pig underwent surgery with RWM perforation according to flowchart 500. An early step 510 is to surgically access the cochlea. At step 520, baseline hearing is measured using compound action potential (CAP) and distortion product otoacoustic emission (DPOAE), as illustrated in FIG. 13. At step 530, the round window membrane (RWM) is perforated using the microneedle mounted on a syringe, as described herein and illustrated in FIG. 14. At step 540, hearing is measured again with CAP and DPOAE immediately following perforation and prior to harvesting.

Figure 15:
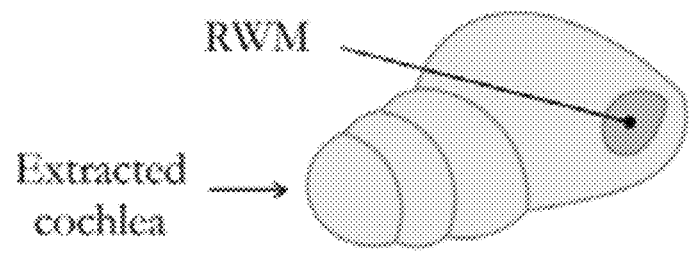

At step 550, the perforated RWM was harvested for analysis at one of four time points following the procedure (post-perforation) (FIG. 15). For non-survival surgeries, harvesting was performed 0-2 hours post-perforation (n=7). These procedures were performed to evaluate perforation size and the reliability of the microneedle surgical technique. For survival surgeries, harvesting was performed at 24 hours (n=6), 48 hours (n=6), and 1 week (n=6) post-perforation. These experiments were used to assess RWM healing over time.

Figure 14:
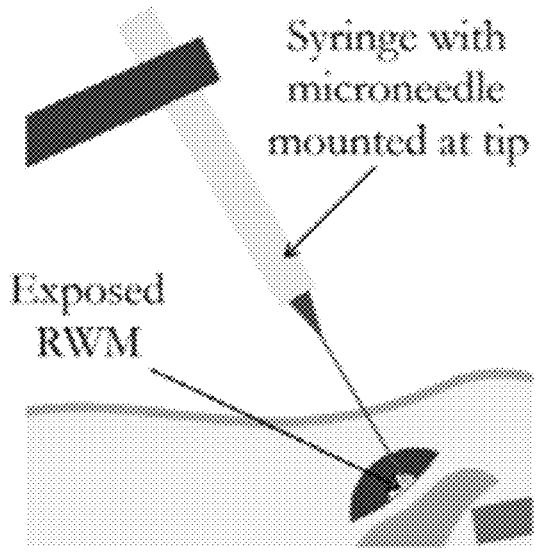

All surgeries were performed on the animal's right ear. The animals were anesthetized using isoflurane gas (induction at 3.0% and maintenance at 1.0-3.5%). Anesthesia depth was determined by respiratory status and toe pinch. Lidocaine was injected subcutaneously for local anesthesia. For survival experiments, 0.5 mg/kg meloxicam and 1.0 mg/kg buprenorphine sustained release formula were administered as additional analgesics. The RWM was accessed via a postauricular incision and by creating a small opening through the skull into the bulla using a Stryker S2 piDrive drill (Stryker, Kalamazoo, Michigan). 2-3 mm of temporal bone were removed to expose and visualize the RWM. The surgical microneedle was secured onto a micromanipulator and was used to create a microscopic perforation in the RWM. (FIG. 14). Perforations were confirmed by one of several signs: visualization of the perforation, bleeding of the RWM, or pooling of perilymph in the round window niche and middle ear. Audiometric testing was conducted at several time points during each experiment: 1) after opening the bulla but prior to perforation, 2) 0-2 hours after perforation, and 3) immediately prior to RWM harvesting at 24 hours, 48 hours, or 1 week post-perforation. The animals were euthanized using pentobarbital overdose. The right temporal bone was extracted using blunt dissection and the RWM was fixed immediately with buffered formalin.

Audiometric Testing

Compound action potential (CAP), which measures auditory nerve activity, and distortion product otoacoustic emissions (DPOAE), which measure outer hair cell health, were used to evaluate effects of microperforation on hearing. A silver ball electrode connected to a silver wire served as a CAP recording electrode and was positioned at the base of the cochlea bone. A reference electrode was placed subcutaneously 7-10 mm from the incision site and a ground electrode was placed subcutaneously between the shoulders. An AC amplifier with a first order high pass filter and a second order low pass filter, with a pass band of ~200 Hz-4 kHz, was used to measure the CAP response. Sound stimulation was generated by a Tucker Davis Technologies (TOT) System (Tucker Davis Technologies Inc., Alachua, Florida) driving a Radio Shack dynamic speaker, connected in a closed-field configuration to the ear canal. Calibration of sound was performed within the ear canal using a Sokolich ultrasonic probe microphone. The CAP stimulus was composed of a 3 ms tone pip of variable frequency presented every 12 ms, with alternating polarity to eliminate the linear component of the cochlear microphonics from the averaged responses CAP responses were collected for 18 frequencies ranging from 0.5 kHz to 40 kHz. Stimulus intensity was steadily increased in 5 dB increments to determine a hearing threshold. The threshold was defined as the lowest stimulus level that evoked a recognizable response curve. CAP threshold shifts for each sampled time point and each frequency were considered significantly greater than zero at a threshold of a=0.025 using one-tailed paired t-tests. To measure DPOAE, a speaker and microphone held fixed to the ear canal were used to provide 70 dB sound stimuli with a fixed frequency ratio f2/f1=1.2 at 1 kHz increments between 1 kHz and 32 kHz and measure resulting distortion products from the ear.

Confocal Imaging of the RWM

Dissected, fixed temporal bones were washed with phosphate buffered saline (PBS) after one hour of fixation. Bony structures surrounding the cochlea were removed carefully using a Stryker 82 πDrive drill and forceps. The RWM was soaked in 1 mM rhodamine B (diluted in PBS), a fluorescent stain selective for elastic tissue, in PBS for 5 minutes, then rinsed with PBS three times and soaked in PBS for 15 minutes. Confocal imaging was performed with a Nikon AlR scanning confocal attachment on an Eclipse TiE microscope stand (Nikon Instruments, Melville, NY), using a 10/0.45 Plan Apo or 20×/0.75 Plan Apo VC objective lens (Nikon). An excitation wavelength of 561 nm was chosen for the laser, and emitted light from 570 nm to 620 nm was allowed to pass to the detector. A stack of images was generated at several focal heights spaced 5 μm and 1 μm apart for the 10× objective and the 20× objective, respectively. At 10× magnification, the pinhole was set at 0.8 Airy unit (AU) to create an optical Z section of 6.35 μm, at 20× magnification, the pinhole was set at 0.9 AU to create an optical Z section of 2.3 μm.

Histology

RWM samples were fixed in 10% formalin immediately post-mortem for one hour and washed in PBS prior to imaging. Following imaging, samples were transferred to 70% ethanol. The remaining histological processing was performed at Molecular Pathology Shared Resource of the Herbert Irving Comprehensive Cancer Center of Columbia University. Samples were decalcified, paraffin-embedded, and cut into 5 μm sections A Russell-Movat Pentachrome Stain was used to view connective tissue of the RWM.

SEM Imaging of Microneedles

After use in surgery, the microneedles were imaged using a scanning electron microscope (SEM) to examine for breaking and bending (Zeiss Sigma VP Scanning Electron Microscope).

Data Analysis

Confocal image analysis was conducted using ImageJ-Fiji software. Perforation sizes were measured using 0-2 hour post-perforation samples, based on a maximum intensity projection image Measurements consisted of perforation area, major axis (an estimation of perforation length from corner to opposite corner), and minor axis (an estimation of perforation width approximately perpendicular to the major axis). Perforation closure over time was evaluated using a maximum intensity projection image and individual focal height images for each membrane. A perforation was considered open if the area within recognizable borders contained no fluorescence. The perforation was considered completely closed if the area within recognizable borders contained no areas lacking fluorescence. All other perforations were considered partially or incompletely closed.

Anatomical Consequences of RWM Perforation

Based on confocal images of RWM samples harvested at 0-2 hours post-perforation, perforations created by the microneedles were fully open and lens-shaped. (FIGS. 16-20). FIG. 16 illustrates a 10× magnification of a membrane, and FIGS. 17-20 illustrate 20× magnification of four separate perforations on different membranes. The microneedles created perforations, measuring 93.1±29.0 μm the major axis and 34.5±16.8 μm the minor axis. The total perforation area averaged across all perforations measured 2572.3±489.3 μm². Furthermore, all microneedles were intact and minimally bent after creating the perforations. One of the microneedles used in the perforation experiments is shown in FIG. 21.

Figure 26:
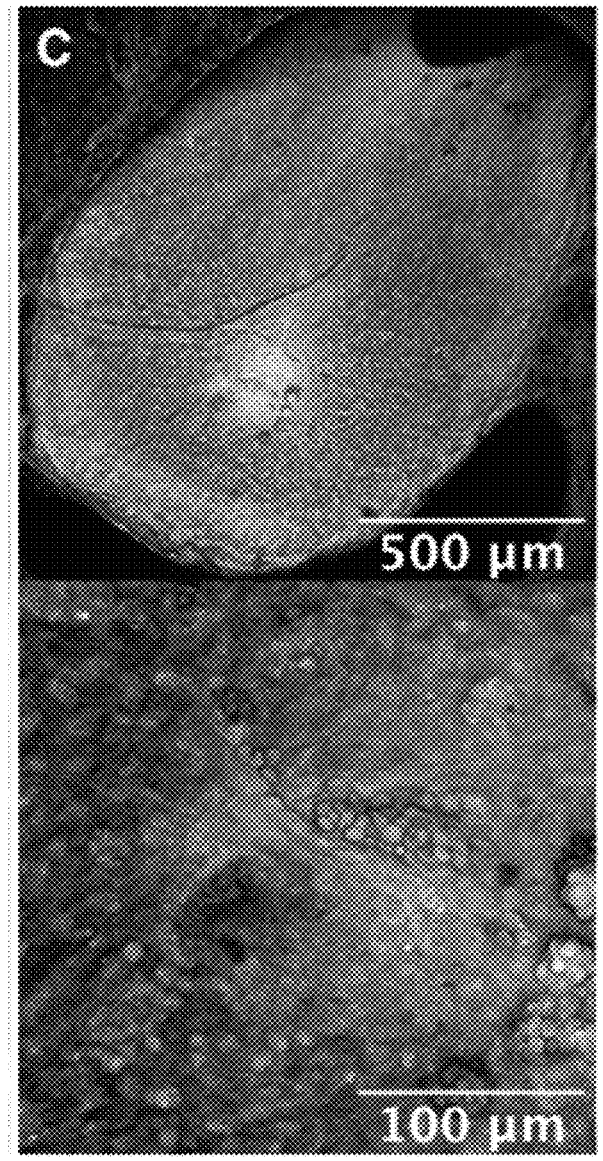
Figure 28:
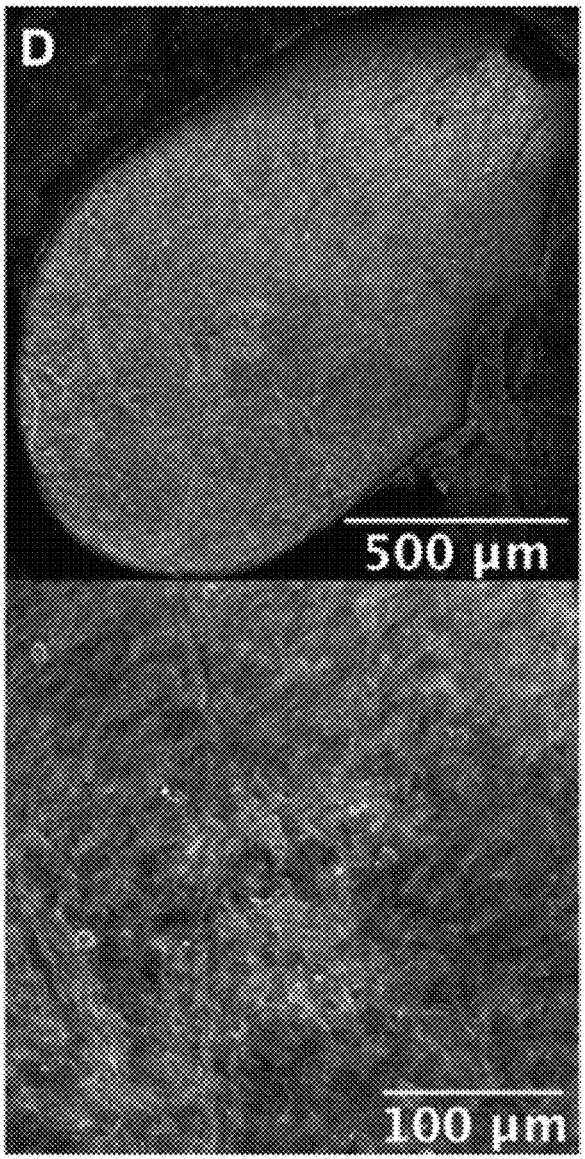

To investigate the longer-term anatomical effects of microneedle perforation, RWM samples harvested at later time points were examined for perforation closure (FIGS. 22-29). FIGS. 22, 24, 26, and 28 are illustrated under 10× magnification, and FIGS. 23, 25, 27, and 29 are illustrated under 20× magnification. FIGS. 22 and 23 illustrate membrane at 0-2 hours post-perforation. At 24 hours, perforations appeared partially closed, with the original perforation shape still evident (FIGS. 24-25). In addition, a collection of tissue was observed within the area of the perforation at 24 hours (FIGS. 24-25). A pentachrome stain of two histological sections confirmed the presence of blood cells and clumps of epithelial cells in the perforation area. FIGS. 30-33 illustrate a first perforation sample taken 24 hours after perforation, shown with increasing magnification. FIGS. 34-37 illustrate a second perforation sample, also taken 24 hours after perforation. The arrows in FIGS. 30-37 point at the perforation location Epithelial cells are aggregated around the perforation sites. At 48 hours, perforations appeared closed, with the original perforation shape still evident (FIGS. 26-27). By one week post-perforation, all harvested RWMs showed complete perforation closure with signs of reconstituted connective tissue fibers appreciated on 20× magnification images. There was little to no extra tissue or debris observed covering the perforation area (FIGS. 28-29). Perforations were not detectable in histologic sections at 48 hours or 1 week.

Functional Consequences of RWM Perforation

The effects of micro needle perforation on bearing were investigated using CAP and DPOAE. FIG. 38 illustrates a mean CAP threshold shift (compared to baseline) for each frequency, shown for all time points. Error bars are two times the standard error. A mild positive CAP threshold shift of 5-10 dB from baseline was observed at 0-2 hours after surgery in the high frequency range from 22 to 40 kHz ($p<0.025$) (FIG. 38). At subsequent time points, no positive CAP threshold shifts were observed except for two frequencies at the lower bound of the testing range—1 kHz and 2 kHz—measured at 48 hours post-perforation ($p<0.025$). Of note, there were negative CAP threshold shifts in the high frequency range observed in survival surgery time points, indicating improved hearing thresholds after perforation compared to baseline Examples of negative high frequency threshold shifts from an individual 48-hour experiment are shown in FIG. 39, at baseline, 0-2 hours and 48 hours after perforation. FIG. 40 illustrates a 1-week experiment, showing measurements at baseline, 0-2 hours and one week after perforation.

DPOAE is a measure of the cochlear condition and is due to the cochlea's active process, which originates in outer hair cells. DPOAE were at the frequency 2f1-f2 in response to a 70 dB stimulus over all survival experiments at baseline, 0-2 hours (FIG. 41, n=18), 24 hours (FIG. 42, n=6), 48 hours (FIG. 43, n=6), and one week (FIG. 44, n=6). Solid gray lines show average noise for the plotted experiments and the shaded gray area shows two times the standard error of the noise. Solid black lines show the mean measured baseline DPOAE signal and densely shaded areas show two times the standard error. Dotted lines show mean DPOAE signal for 0-2 hours, 24 hours, 48 hours, and one week experimental time points and lightly shaded areas show two times the standard error for respective experiments. All DPOAE measurements were web out of the noise level and were similar between baseline and post-perforation time points a small DPOAE level increase can be seen in measurements from survival surgery time points (24 hours. 48 hours, and 1 week) compared to baseline.

Microneedles according to the above embodiments can accurately and precisely perforate the RWM in vivo without producing permanent hearing loss, in addition, these perforations heal within one week. All guinea pig surgeries successfully produced RWM perforations that were comparable in size and shape to those produced in vitro: lens-shaped with an average major axis length approximately equal to microneedle shaft diameter of 100 μm. The minor axis and perforation area were also similar to measurements obtained in vitro. These results illustrate the repeatability of microperforations using the microneedles in vivo, even when performed by different investigators. In addition, due to the inherent constraints of performing in vivo surgery, the angles at which perforations were introduced differed from those performed under more controlled conditions in vitro. Nevertheless, the perforation sizes remained consistent, suggesting that variation in the angle of perforation does not affect perforation size. Importantly, the microneedles bent only minimally after perforating the RWMs.

The safety of microneedle perforation of the RWM was evaluated in this study by examining perforation healing and effects on hearing. Confocal imaging demonstrated that healing of guinea pig RWM microperforations begins within 24 hours with notable progress by 48 hours and complete closure by 1 week. This process occurs more quickly than in full RWM rupture, which has been observed to require two weeks for complete healing. Healing of RWM microperforations within a week is clinically important because it sets a time frame for drug diffusion across the microperforations. Moreover, RWM healing prevents long-term leakage of perilymph from the inner ear.

Beyond establishing a time frame for perforation healing, confocal images and histological sections also provided detailed insight into the healing process. At 24-48 hours, aggregated epithelial cells were visible in and around the perforations but, by one week, these aggregates were no longer visible and the perforations were completely healed. In fact, by one week, perforations were often difficult to locate because the healed perforation areas appeared to have fibrous regrowth, resembling the surrounding un-perforated membrane. The healing of the RWM appears remarkably similar to the healing process described in the tympanic membrane, which also begins with epithelial migration followed by possible fibrous regrowth. Future investigation into cell signaling and growth factors would help to elucidate the long-term healing of the RWM.

CAP and DPOAE measurements evaluated changes in hearing thresholds and outer hair cell health associated with RWM perforation, and demonstrated a temporary high frequency hearing loss that resolves within 24 hours. Of note, CAP measurements taken at least 24 hours after surgery indicate a negative threshold shift in the 20-40 kHz range. A similar phenomenon was observed in the DPOAE measurements, where survival surgery measurements were slightly higher than baseline measurements starting at 24 hours. It is likely that this threshold shift was a result of acoustic trauma from the surgery prior to measurement of baseline hearing; surgical access to the cochlea has been shown to cause temporary hearing loss in this range of 20-40 kHz in guinea pigs. As such, the results may underestimate the positive CAP threshold shifts in the high frequency range Observed at 0-2 hours. Nevertheless, improved post-perforation CAP responses compared to the measured baseline indicate that microneedle perforation itself does not cause permanent hearing loss.

Perforation of Human RWM with Microneedles

Two microneedle prototypes in accordance with exemplary embodiments—their designs based on the thickness and mechanical properties of the human RWM (HRWM)—are capable of precisely perforating the HRWM with minimal membrane trauma and limited microneedle displacement to avoid intracochlear trauma.

The efficacy of the microneedles is evaluated by measuring peak force of perforation, displacement of the microneedle during perforation, and size of perforation. These measurements were guided by clinical concerns: a small peak force is desired for minimizing membrane trauma, the distance traveled by the microneedle during perforation must be sufficiently small to avoid contact with structures behind the HRWM, and the size of perforations determines the precision of our microneedles.

Based on the thickness of the HRWM and characterizations of its mechanical properties, microneedles were designed to perforate the HRWM while minimizing trauma, membrane deformation, and intracochlear pressure. Microneedle experiments in guinea pigs showed that perforation of the guinea pig RWM requires approximately 1 mN of force. As the HRWM is approximately 4-5× thicker than in the guinea pig, the microneedles designed for human use required a sturdier construction that resists microneedle bending or damage. Several design modifications were made to the previous microneedle design to compensate for the larger perforation force that was expected, as discussed below.

Figures 45, 46:
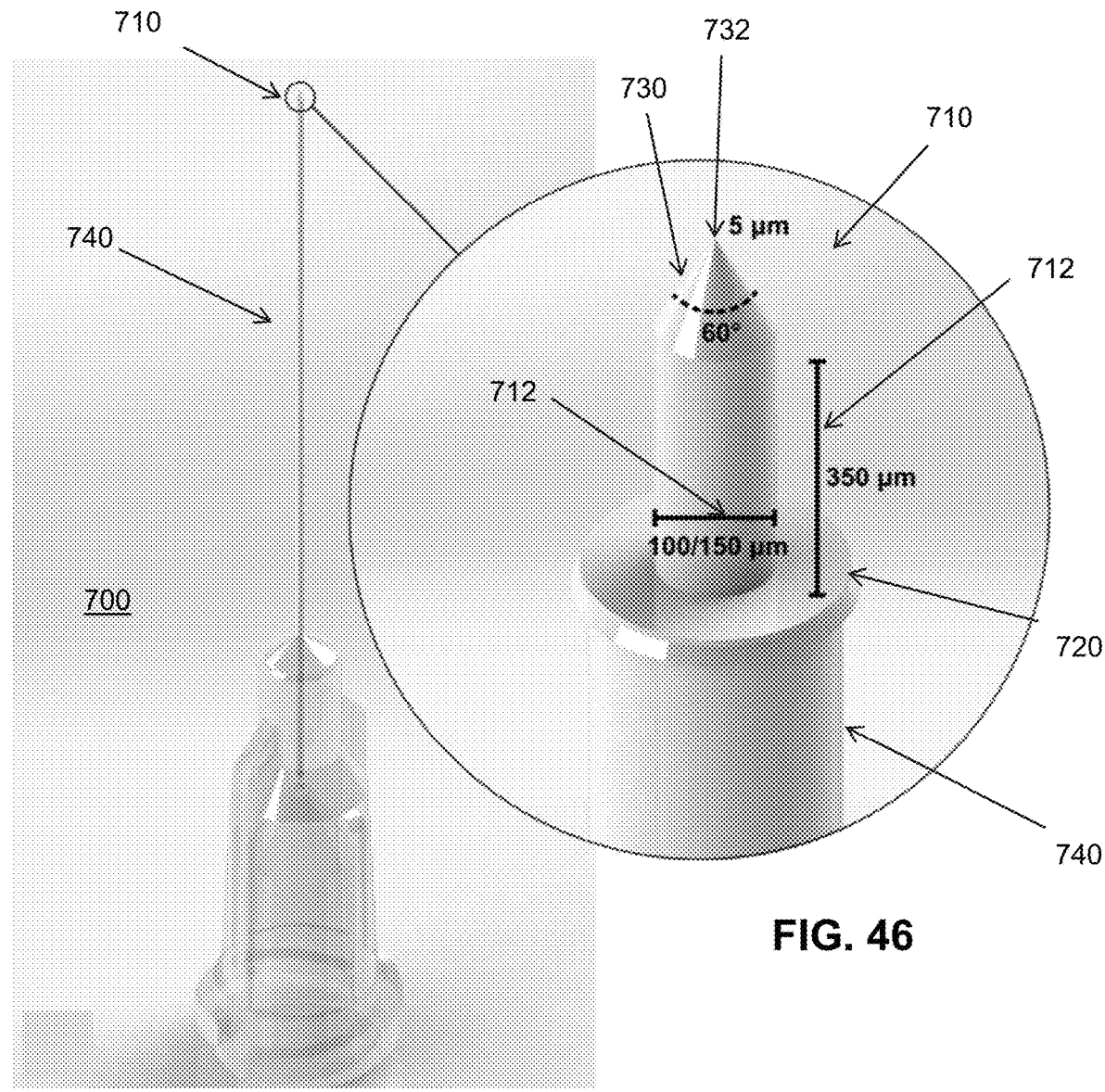
Figure 47:
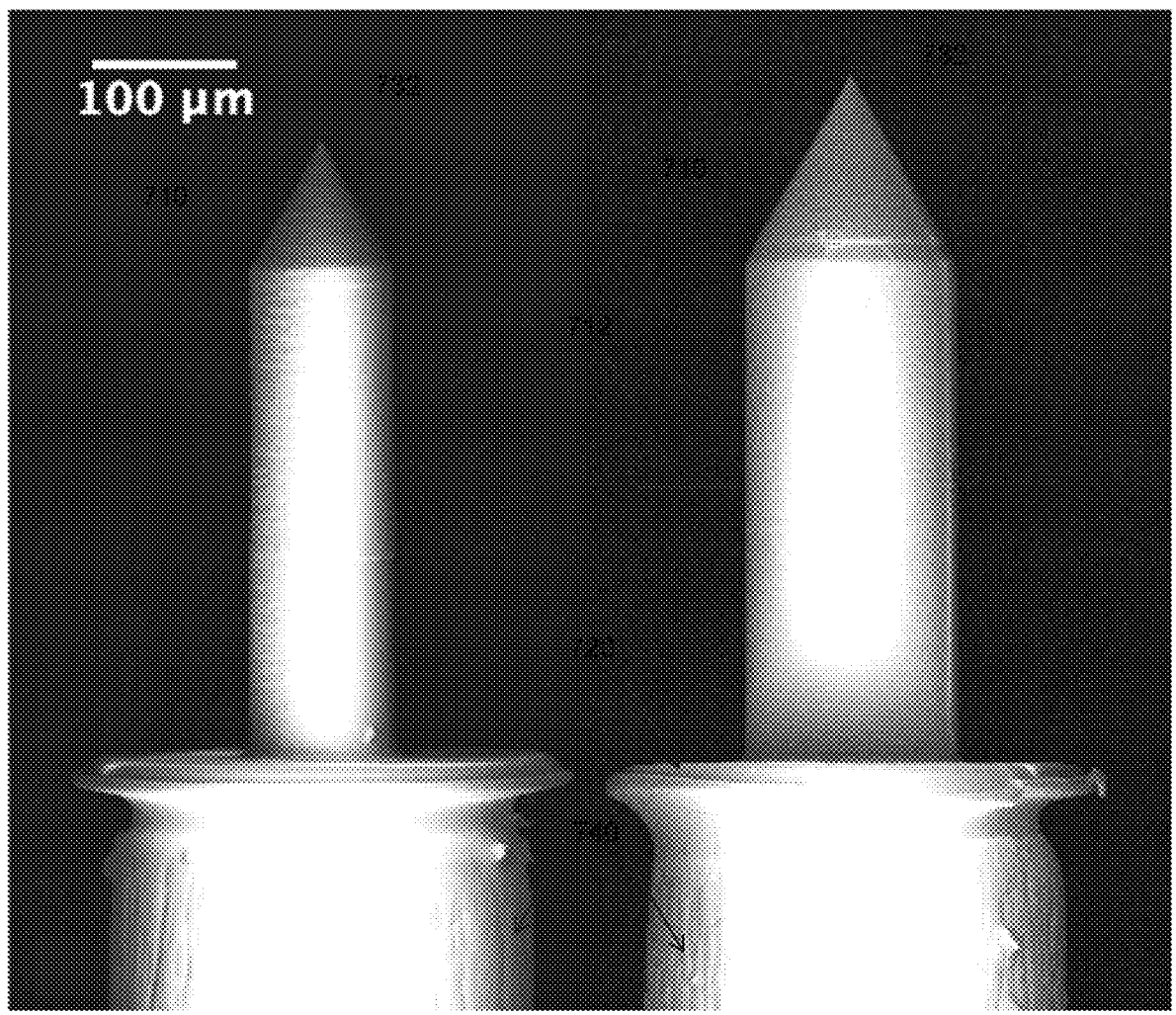
FIG. 47.

As illustrated in FIGS. 45-47, apparatus 700 includes microneedle 710 mounted on base 740, such as a hypodermic needle. Microneedles 710 were fabricated with two shaft diameters 712: 100 µm diameter (left in FIG. 47) and 150 µm diameter (right in FIG. 47). The 3D-printing technology allows great flexibility in microneedle design, including variable shaft sizes for creating holes of any size. As illustrated in FIG. 46, each microneedle 710 has a shaft height 714 of 350 µm, which is larger than in guinea pig microneedles, to accommodate the deformation that the HRWM undergoes during perforation so the hilt 720 of the microneedle does not contact the HRWM during perforation. All microneedles have a shaft-to-tip taper angle 730 of 60°, which is larger than in guinea pig microneedles, to prevent the microneedle from bending during perforation. The microneedle tips 732 have a 75 µm radius of curvature, which is larger again for strength and stabilization. As illustrated in FIGS. 45 and 47, the base of each microneedle 710 was designed for mounting onto base 740, such as a commercially available 30-gauge syringe needle (Industrial Unsterilized Blunt Tip Dispensing Needle with Luer Lock from BSTEAN, USA) with an inner diameter of 160 µm and outer diameter of 300 µm.

The microneedles were 3D-printed using two-photon polymerization (2PP) lithography with the Photonic Professional GT system (Nanoscribe GmbH, Karlsruhe, Germany). The substrate material was a crystal Si (100) wafer and the photoresist was IP-S (Nanoscribe GmbH) in a Dip-in Laser Lithography configuration with a 25× objective (Nanoscribe GmbH). Stereolithography files were generated using the SolidWorks (Dassault Systems SolidWorks Corporation, Concord, New Hampshire) computer aided design (CAD) software. These files were subsequently converted into Direct Laser Writing commands using the Describe (Nanoscribe GmbH) software. After completion of 2PP, the microneedles were rinsed in a propylene glycol monomethyl ether acetate solution and subsequently in two baths of isopropyl alcohol. At this point, the microneedles were ready for use, and were mounted onto the syringe needles with resin epoxy.

Six temporal bones (ages 62-74) were dissected to completely expose the HRWM from the middle and inner ear sides with the following steps: first, the cochlea was exposed with a canal wall down mastoidectomy and by opening the facial recess. The cochlea was removed from the surrounding temporal bone. Finally, the HRWM was isolated within a thin ring of bone and cleared of false membranous tissue and basilar membrane attachments. The prepared HRWMs were transported in phosphate buffered saline (PBS) and kept hydrated during all stages of experimentation.

The HRWMs were perforated three times each from the middle ear side, using same size microneedles within a HRWM. Three HRWMs were perforated with 100 µm microneedles, and the other three with 150 µm microneedles using an in-house microindenter setup (n=18 perforations). Perforation locations depended on the surgical anatomy of each HRWM. The microindenter setup includes a motorized linear translator to which the microneedle is secured (Zaber Technologies Inc., Vancouver, British Columbia, Canada) and a force transducer to measure the axial force exerted on the microneedle during perforation (Transducer Techniques, Temecula, California). For stabilization the HRWMs were bonded to plastic 3D109 printed stages using dental cement. A 3D digital microscope (VHX-5000, Keyence Corporation of America, Elmwood Park, New Jersey) was used to visualize the experiments and capture videos, which were used to position the HRWMs in relation to the microneedles and to identify perforation events. The perforations occurred at a prescribed rate of 150 µm/minute.

The HRWMs were imaged prior to perforation for overall structure and thickness and after perforation to inspect individual perforations. In preparation for imaging, the HRWMs were immersed in 1 mM Rhodamine B dissolved in PBS for 30 minutes, serially rinsed in PBS three times, and then soaked in PBS for 12 hours. Confocal imaging was performed using a Nikon A1R scanning confocal attachment on an Eclipse TiE microscope stand (Nikon Instruments, Melville, New York). Images of the entire HRWM were taken using a 10×/0.45 Plan Apo objective lens (Nikon) and required stitching (ImageJ-Fiji). Orthogonal slices were used to measure the thickness of the HRWM, with twenty-five measurements per HRWM, equally spaced in the orthogonal plane and the stacking direction (FIGS. 48, 49($a$), 49($b$)). To measure perforation sizes, images using a 20×/0.75 Plan Apo VC objective lens (Nikon) were projected in the stacking direction with maximum intensity to visualize a flattened membrane. Perforation sizes were measured manually and confirmed by scrolling through images slices in ImageJ-Fiji. If debris obstructed visualization of a perforation under fluorescence microscopy, transmitted white light was used 126 instead. The areas of the perforations were measured by outlining each perforation and computing the area.

After perforating the HRWM, the microneedles were examined for potential bending and damage using scanning electron microscopy (Zeiss Sigma VP Scanning Electron Microscope).

Statistical analysis was performed in MATLAB. All data are presented as their mean±standard deviation (SD). Linear mixed effects models were used to compare measurements between the two microneedle sizes while accounting for intermembrane variability. The significance threshold was set at 0.05.

Figure 48:
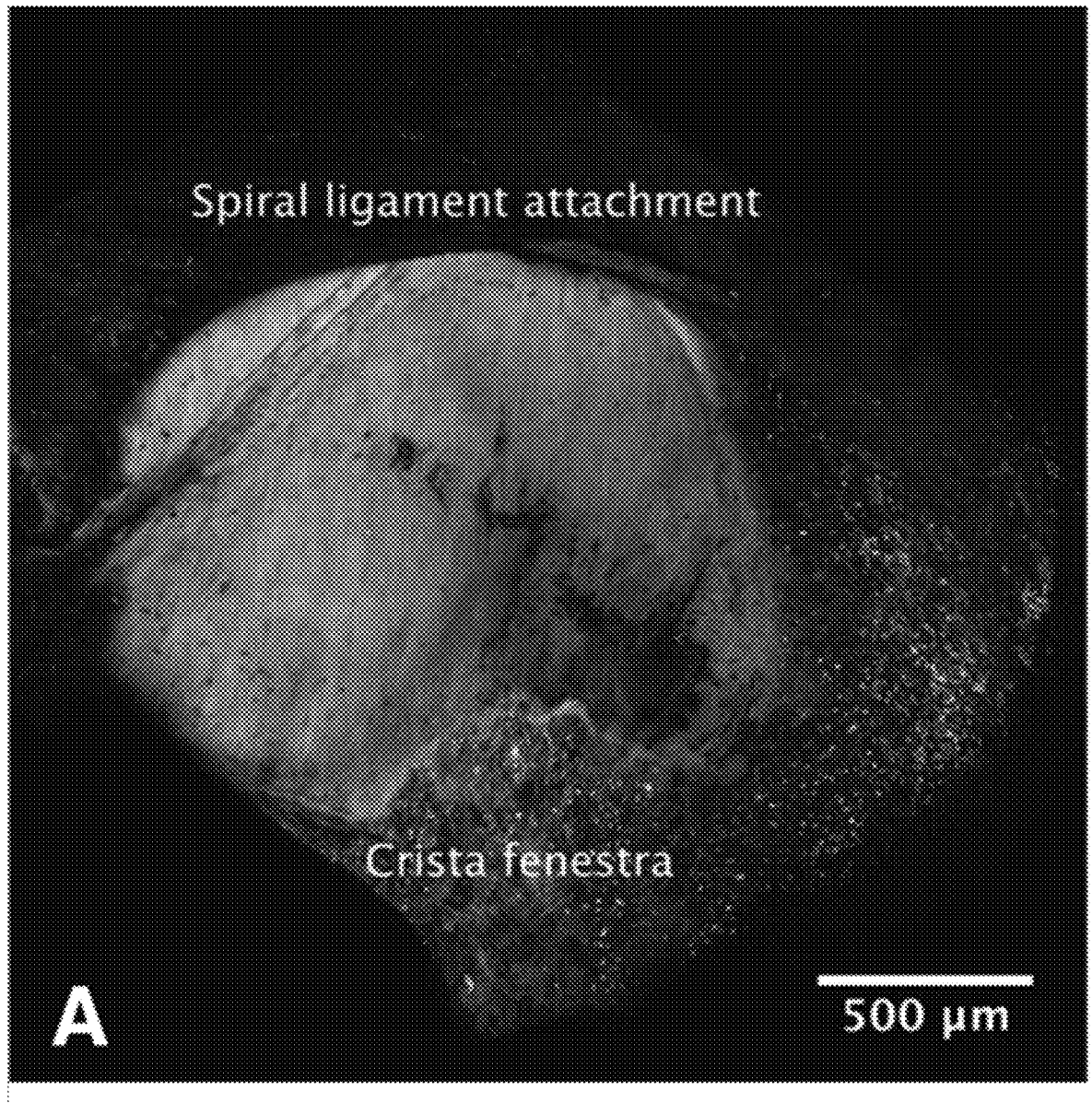
FIG. 48 is an enlarged view of the human RWM viewed from the inner ear side.
Figure 49A:
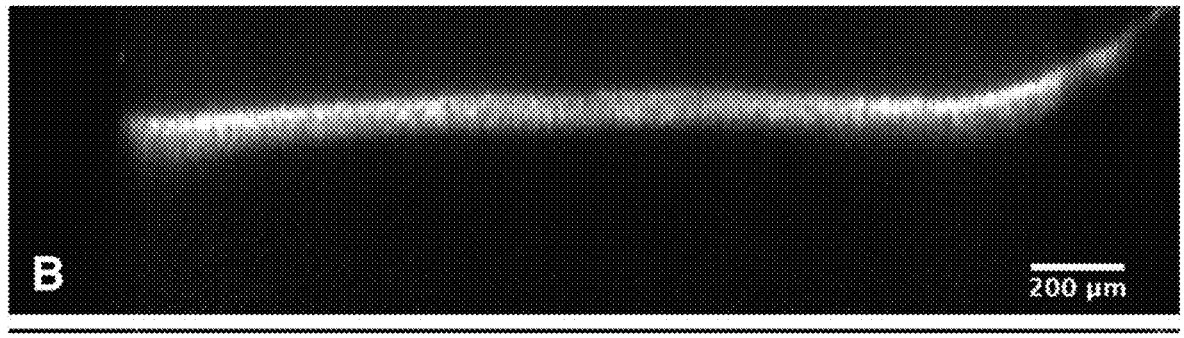
FIGS. 49(a) and 49(b) are enlarged cross-sectional views through the human RWM in different locations.
Figure 49B:
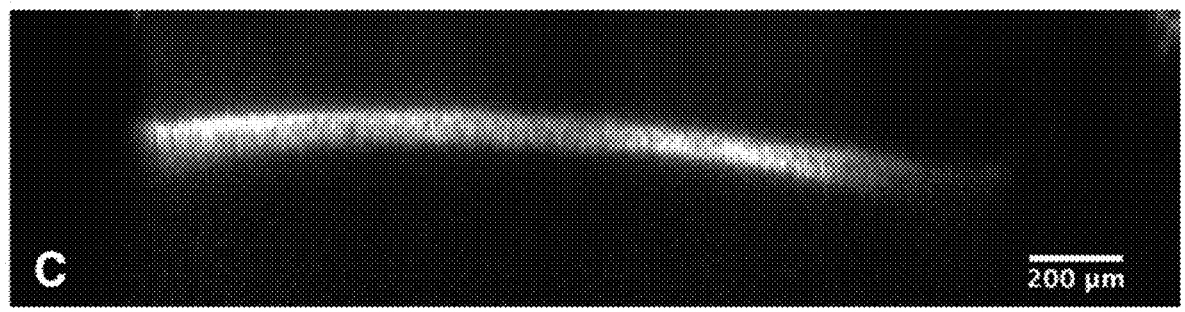

The thickness across all HRWMs, determined by confocal microscopy, was 60.1±14.6 (SD) Rhodamine B staining of the HRWM, which allows for visualization of the HRWM collagen and elastin tissue fibers, showed marked uniformity in the orientation of collagen and elastin fibers (FIG. 48).

Perforation Size and Shape

Figure 50:
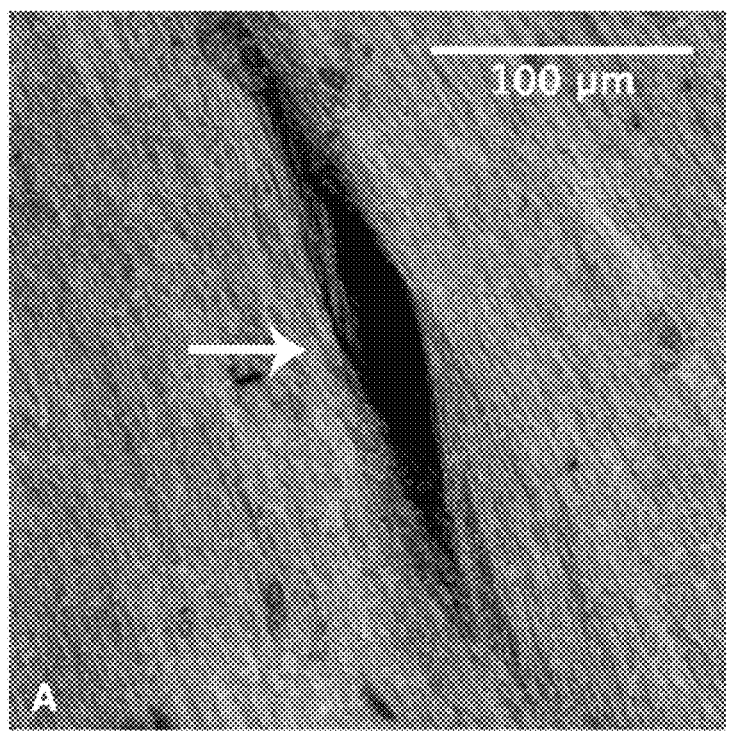
FIG. 50 is an enlarged view of the human RWM following perforation.

The microneedle perforations were slit-shaped with distinct major axes and minor axes (FIG. 50). In all cases, the major axis aligned with the orientation of collagen and elastin fibers in the HRWM with the minor axis perpendicular to the fiber direction. Average dimensions of perforations created from each needle size are shown in TABLE 1 with standard deviation.

Note that the major axes of the perforations are approximately equal to the microneedle shaft diameters. During a perforation, an opening is created in the HRWM that is at least as large as the microneedle shaft diameter. After withdrawing the microneedle, the perforation partially closes along the minor axis while the major axis retains its length, resulting in the slit-shape. Although the major axis of the perforation is directly correlated with the diameter of the microneedle shaft, the relationship between microneedle diameter and perforation minor axis is less clear (TABLE 2). There was a significant difference in perforation minor axis between different microneedle shaft sizes (p=0.01), as determined by a linear mixed effects model with perforation minor axis as a fixed effect and specific HRWM sample number as a random effect to account for intermembrane variability.

TABLE 2

| Microneedle Size (µm) | Major Axis (µm) | Minor Axis (µm) | Area (µm²) |
| --- | --- | --- | --- |
| 150 | 153.9 ± 20.9 | 15.9 ± 7.9 | 1865.8 ± 1235.6 |
| 100 | 103.4 ± 17.1 | 7.7 ± 2.6 | 705.2 ± 187.7 |

Figure 51:
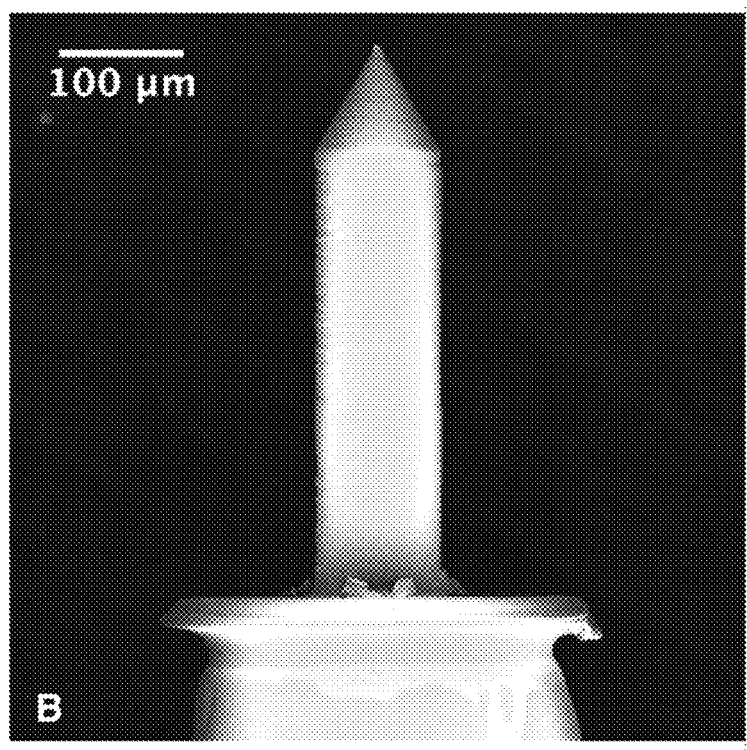
FIG. 51 is an enlarged view of the apparatus of FIGS. 45-47 following perforation.

The used microneedles were indistinguishable from unused microneedles under light microscopy. SEM of the microneedles after perforation confirmed that the microneedles did not undergo notable deformation or damage; only the tips of the microneedles had minimal signs of blunting or bending after use (FIG. 51).

Figure 52:
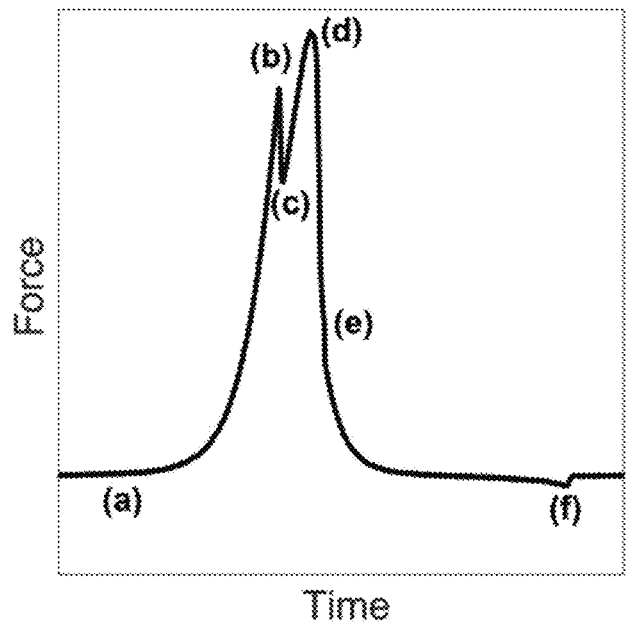
FIG. 52 is a plot illustrating force on the human RWM as a function of time during perforation.
Figure 53:
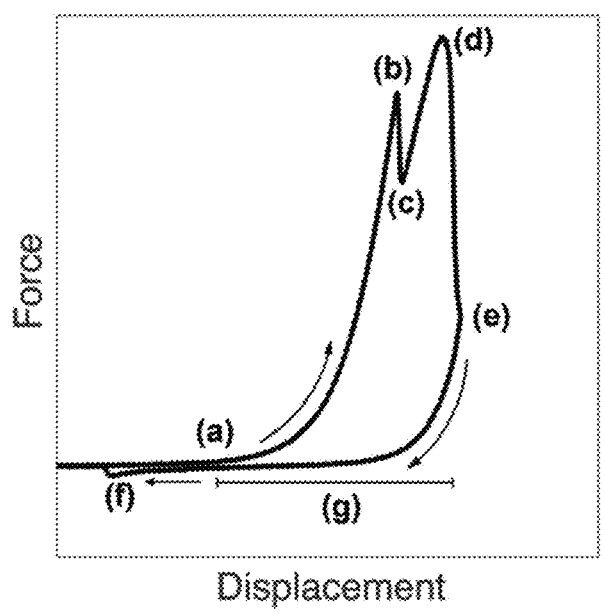
FIG. 53 is a plot illustrating force on the human RWM as a function of displacement during perforation.
Figure 54:
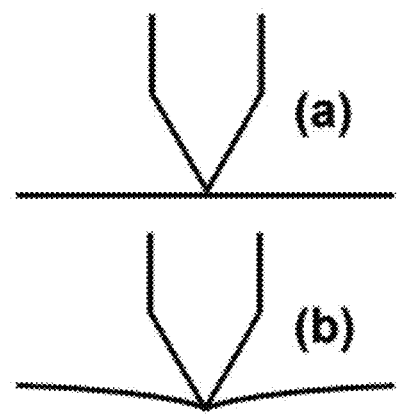
FIG. 54 is a schematic diagram illustrating four stages of perforation, referenced to the same stage of perforation in FIGS. 52-53.

A representative example of the force applied to the HRWM during microneedle indentation is illustrated in FIG. 52 as a function of time and as a function of microneedle displacement (FIG. 53), and a schematic of the relative microneedle and HRWM locations throughout perforation (FIG. 54). Positive displacement indicates microneedle movement towards the HRWM. These force curves explain the events that occur during perforation. Upon microneedle contact with the HRWM (a), the force increases until a first peak (b) when the microneedle tip is about to perforate the membrane. The microneedle tip then perforates the membrane, indicated by the temporary drop in force (c). The force rises again to a second peak (d) as the microneedle taper expands the perforation to the size of the microneedle diameter. Immediately, the force drops due to slipping of the needle along the microneedle shaft, indicating a complete perforation, at which time the microneedle is withdrawn (e). The microneedle then encounters a negative force (f) due to friction between the membrane and the microneedle. Although individual experiments were associated with minor variations in the shape of the force curves, the majority followed the shape described in FIGS. 52-53. In what follows, peak force (d) is defined as the maximum force during a perforation, trough force (f) is the minimum (usually negative) force during perforation, and the microneedle displacement (g) is the distance that the microneedle travels during perforation, which can be obtained from the difference in microneedle positions between (d) and (a).

As detailed above, each HRWM was perforated three times in different locations. There was no apparent difference in peak forces between one perforation and subsequent perforations within the same HRWM.

Figure 55:
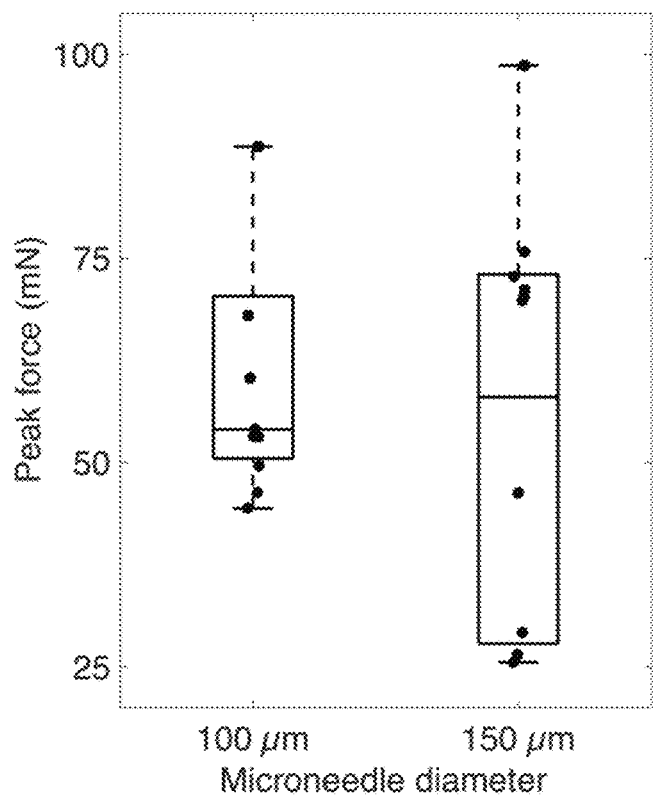
FIG. 55 is a box-plot illustrating peak force during perforation for each of the needles illustrated in FIG. 47.

The average peak force across all perforation experiments was 58.11±19.41 (SD) mN. For 150 µm microneedles, the average peak force was 58.61±23.77 mN. For 100 µm microneedles, the average was 57.56±12.92 mN. There was no significant difference in peak force between microneedle shaft sizes (p=0.862), as determined by a linear mixed effects model with microneedle size as a fixed effect and HRWM sample number as a random effect to account for intermembrane variability. The box-plot in FIG. 55 shows the distribution of peak forces according to microneedle shaft size.

Figure 56:
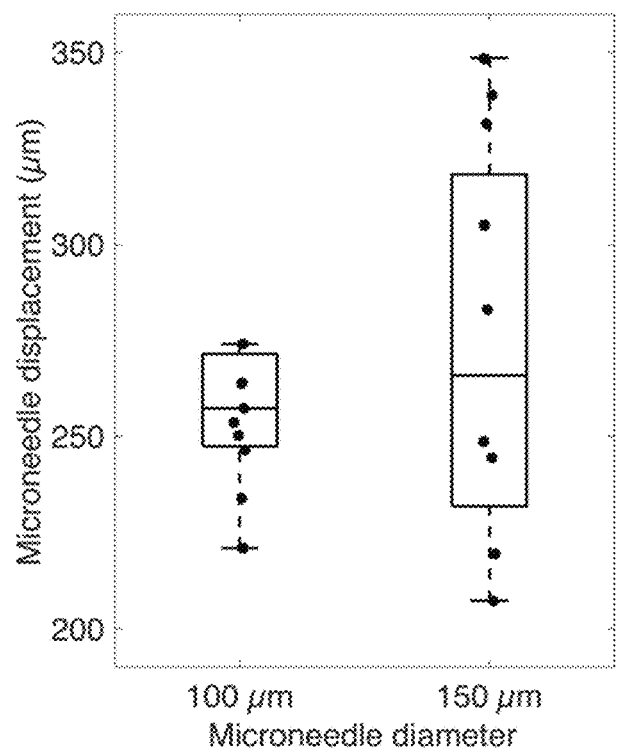
FIG. 56 is a box-plot illustrating microneedle displacement during perforation for each of the needles illustrated in FIG. 47.

The average microneedle displacement across all perforation experiments was 270.52±42.88 µm. For 150 µm microneedles, the average microneedle displacement was 287.51±51.69 µm. For 100 µm microneedles, the average was 251.64±15.34 µm. There was no significant difference in microneedle displacement between microneedle shaft sizes (p=0.06), as determined by a linear effects model with membrane displacement as a fixed effect and specific HRWM sample number as a random effect. The box-plot in FIG. 56 shows the distribution of microneedle displacement according to microneedle shaft size.

Two novel designs of 3D-printed microneedles for perforating the HRWM with the goal of enhancing diffusion of therapeutic and diagnostic agents into the inner ear are described herein. Both 100 µm and 150 µm microneedles have been shown to create accurate and precise perforations in the HRWM. The shaft diameter of the microneedle plays a role in determining both the major and minor axes of the slit-like HRWM perforations. The dimension of major axis closely approximates the shaft diameter of the needle. On the other hand, the relationship of shaft size to the minor axis is more complex; the mean minor axis from 100 µm microneedles was less than half the size of those from 150 µm microneedles.

In comparison with guinea pig RWM perforations, the HRWM perforations were narrower than expected; whereas the perforations in guinea pigs were lens-shaped with the minor axes representing ~25% of the major axes, the perforations in HRWM were slit-shaped with minor axes representing 7-11% of the major axes. This finding suggests that the HRWM may be under higher tension than the guinea pig RWM, although further investigation into its mechanical properties is necessary. Previous research regarding the round window membrane has shown that a membrane with uniformly oriented collagen and elastin fibers is stiffer than a membrane with randomly oriented fibers. The fibers in the HRWM appear to be more uniformly oriented than in the guinea pig RWM; this stiffness may be contributing to the slit-shape of the perforations. Moreover, the slit-shape suggests that the primary mechanism of HRWM perforation is fiber-fiber separation, rather than tearing of the HRWM. This is further supported by the observation that the collagen and elastin fibers remain continuous along the sides of the perforation without signs of damage. These findings are promising indicators for the ability of the HRWM to heal after perforation; in vivo studies will clarify the healing process of the round window membrane after microneedle perforation.

Consistent with expectations, the thicker HRWM and broader microneedle taper design required higher peak perforation forces (average=58.11 mN). There was no significant difference in the peak forces between 100 µm and 150 µm diameter microneedles, which indicates that shaft diameter alone does not affect peak force during perforation. The radius of curvature of the microneedle tip or the taper angle of the microneedle tip is believed to play a role in determining the peak force. These insights are important for further improving microneedle design. Importantly, SEM of the microneedles post-perforation show that the microneedles are durable and can withstand at least the peak forces measured in this study.

The sharp tip of the microneedles succeeded in reducing membrane deformation during perforation. Membrane deformation during perforation is important because large deformations may increase risk of unintentional trauma to the HRWM. Moreover, large membrane deformations can decrease intracochlear volume and thus increase intracochlear pressure during the perforation process. In the microneedle force curves, the decrease in force after the first peak and before the second peak indicates the release of elastic strain energy in the HRWM induced by the initial perforation by the microneedle tip. Afterwards, the microneedle glides through the HRWM, expanding the size of the perforation laterally. During the lateral expansion of the perforation (second peak), friction between the HRWM and the microneedle contributes to further deformation of the HRWM in the direction of microneedle movement (axial). This is in contrast to perforations using blunt-tip needles (no taper to the tip), in which we expect single-peaked force curves. With a blunt needle, the membrane deforms continuously from initial needle contact until complete perforation when the entire needle diameter passes through the HRWM. Membrane relaxation does not occur until after complete perforation—thus, all aspects of a blunt needle perforation contribute to deformation of the HRWM. In comparison, the microneedles in this study induce less HRWM deformation and minimize increases in intracochlear pressure associated with microneedle perforation.

The microneedle displacement that occurs during perforation was also studied to ensure that the distance that the microneedle travels is less than the available space behind the HRWM. The distance between the HRWM and the basilar membrane—the nearest structure within the inner ear—is approximately 1.2 mm. Across all perforation experiments, the mean microneedle displacement was 270.52 µm and the maximum across all experiments was 348.56 less than half the distance that is available behind the HRWM. There was no significant difference in microneedle displacement between 100 µm and 150 µm microneedles. Both microneedles, regardless of shaft diameter, thus show promise as surgical tools that can safely create perforations in the HRWM without damaging inner ear structures.

In accordance with exemplary embodiments, the microneedles described herein are envisioned for use in the operating room. It is understood that these microneedles may find use for minimally invasive office-based procedures for the diagnosis and treatment of inner ear diseases via the HRWM. Recent advances in the development of microendoscopes and mini-otoscopes have demonstrated access to the RWM via transtympanic approach. The availability of tools for in-office visualization of the RWM will greatly facilitate the broad application of microneedles as diagnostic and therapeutic tools for the practicing otolaryngologist.

Drug Delivery Across the RWM

A technique for enhancing IT injection for more effective and consistent drug delivery across the RWM and into the cochlea is described herein. In particular, use of the microneedle designs, such as though discussed hereinabove, to make multiple microperforations with a large total cross-sectional area can further augment diffusive transport. Compared to a single large perforation in the RWM, multiple microperforations with the same total cross-sectional area are advantageous because holes of smaller diameter exhibit higher viscous resistance to fluid flow, simultaneously enhancing diffusive transport of therapeutic reagents into the cochlea and reducing outward leakage of perilymph. Moreover, the interaction between microperforations and novel gelatinous drug carriers—as compared with conventional saline solution—provides additional therapeutic advantages as discussed below.

According to another exemplary embodiment, a method of treatment of the inner ear is disclosed herein. A first step is providing a plurality of microperforations in the membrane of the inner ear. As will be discussed below, the procedure can include four or more perforations about 100 μm in size. The microneedles being used can include the microneedles discussed above and illustrated in FIGS. 45-47. A next step in the procedure is injecting the region via intratympanic dosing adjacent to the microperforations with a drug formulation dissolved in a compound that undergoes gelification at human body temperature. As discussed below, the compound is a hydrogel. The hydrogel can includes polaxamer 407. Drug formulations to be used in connection with this procedure is gentamicin, or other similar antibiotics.

According to another exemplary embodiment, a system for treating a membrane of the inner ear via intratympanic dosing includes at least one needle for providing a plurality of microperforations in the membrane; and a drug formulation dissolved in a compound that undergoes gelification at human body temperature. The needle being used for these procedures defines an outer diameter of about 100 μm (microns), as discussed above and illustrated in FIGS. 45-47. In some embodiments, the membrane in the round window membrane (RWM). In some embodiments, the drug is gentamicin, or other antibiotics. In some embodiments, the compound is a hydrogel. In some embodiments, the hydrogel includes poloxamer 407.

An adjunct to microneedle-based drug delivery to the inner ear is the development of sustained-release drug formulations that minimize the variability in a perilymph pharmacokinetic profile. Of particular interest due to its thermosensitive properties, the hydrogel poloxamer 407 is a liquid when kept cool, but transforms into a semi-solid hydrogel at higher temperatures. This gelification phenomenon is reversible, and higher poloxamer 407 (P407) concentrations result in lower transition temperatures and greater gel strength. P407 acquires its unique physical traits from a combination of distinct hydrophilic and hydrophobic blocks, whose solubilities in water are temperature dependent; its chemical structure appears below:

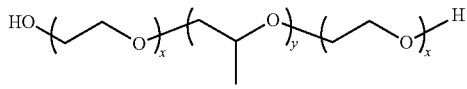

Drugs and other solutes can be dissolved into liquid P407 solutions without significantly inhibiting gelification. Via conventional IT dosing, a room-temperature P407-based solution containing otologic therapy can be injected into the middle ear space, where body temperature triggers transformation of the mixture into a gel. In turn, gelification can prolong the residence time of the injected solution and maintain contact between the drug and the RWM. In humans, a P407-based antibiotic formulation (OTIPRIO®; Otonomy, Inc) administered via IT injection has been approved for the treatment of middle ear infections. Since these infections affect structures immediately adjacent to the cochlea, this drug delivery technique is believed useful to treat inner ear disease. Indeed, animal studies have demonstrated that P407-based dexamethasone formulations, delivered via IT injection, allow for sustained-release drug delivery to the cochlea.

A Valia-Chien cell apparatus separated by an artificial barrier membrane was used to compare the in vitro drug delivery kinetics of the small molecule Rhodamine B delivered via P407 and saline solution, both with and without perforations. The applied methods for measuring transmembrane diffusion were adapted from the American Association of Pharmaceutical Scientists as well as the Federal Drug Administration recommendations for in vitro percutaneous absorption rate studies (EPA, Recommended Protocol For In Vitro Percutaneous Absorption Rate Studies, Federal Register Notices, 61(65):14773-14778, 1996. Agency Docket: OPPTS-42186A.)

Rhodamine B (RhoB) (479.01 g mol$^{-1}$, log Pow 1.95, >99% purity; ACROS 29657) is a fluorescent tracer that can be rapidly and accurately quantified with fluorescent microscopy (Acros Organics, Pittsburgh, PA). RhoB has previously been used as a proxy for relevant otologic therapies and has a molecular weight comparable to that of gentamicin. Accordingly, it is expected that the results for RhoB will be equivalent to those for gentamicin dissolved in saline or P407. A solution of 0.10 mM RhoB dissolved in phosphate-buffered saline (PBS) was used as the therapeutic proxy for 40 mg mL$^{-1}$ solution of gentamicin (0.08 mM), a common concentration used in IT injections for the treatment of Meniere's disease. Throughout the description, the terms PBS and saline are used interchangeably.

P407 powder (Spectrum Chemical, Gardena, CA) was mixed with demineralized water and RhoB to create a 0.1 mM RhoB solution in 18% P407 by weight. The resulting mixture was stirred at room temperature and kept overnight in a refrigerator at 3 to 4° C. to facilitate dissolution of the P407 powder. At the chosen P407 concentration, the mixture transitioned into gel upon placement within the room-temperature testing apparatus.

Figure 57:
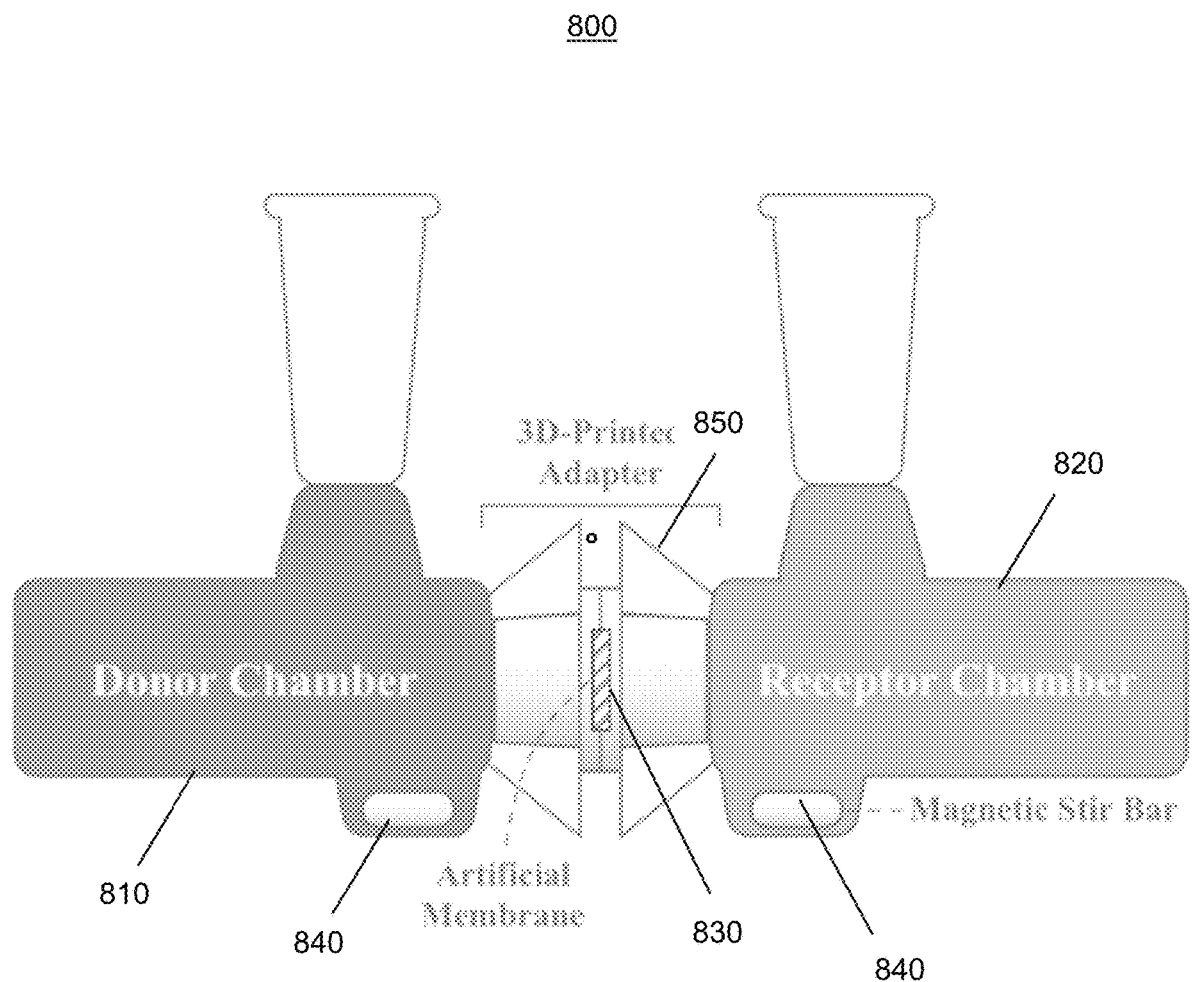
FIG. 57 is a schematic view of a horizontal diffusion cell apparatus.

Diffusion of RhoB through an artificial membrane barrier was performed using 9 mm clear unjacketed Valia-Chien diffusion cells (PermeGear Inc., Hellertown, PA) with 5 mL volumes and flat-ground joints. The cell 800, as shown in FIG. 57, includes three parts: (1) a donor half-cell or chamber 810, (2) a receptor half-cell or chamber 820, and (3) an artificial membrane barrier 830 separating the two. The Valia-Chien diffusion cells 800 were arranged horizontally, mitigating the effects of gravity on particle movement and allowing for active stirring of both the donor 810 and receptor compartments 820 by magnetic mini-stirrers 840 (HI 190M-1, Hanna Instruments, Woonsocket, RI). A 3D-printed adapter 850 was used as a conduit between the chambers 810, 820.

The donor chamber 810 was filled with 5.0 mL volumes of: (A) 0.1 mM RhoB in PBS or (B) 0.1 mM RhoB in 18% P407. An additional sample of donor solution was reserved for the calibration of fluorescence detection, as detailed below. Active stirring of the donor chamber 810 was performed for experiments utilizing PBS, but not those utilizing gelified P407. Initial filling of the donor chamber marked time zero for each experiment.

The receptor chamber 820 was filled with 5.0 mL of PBS prepared by dissolving 9.6 g of Dulbecco's Phosphate Buffered Saline powder (Sigma-Aldrich) in 1.0 L deionized water. An Eppendorf micropipette was used to withdraw 75 μL of fluid from the receptor chamber every 15 minutes, from 0 min to 165 min, for a total of 12 samples. The collected samples were placed in individual wells of a 96-well plate for further analysis. The withdrawn solution was replaced with 75 μL of PBS to prevent advection of fluid within the system. The concentration in the receptor chamber 820 was significantly lower than that in the donor chamber 810 for the entirety of experiments; as such, this process had minimal effect on subsequent measurements of donor chamber concentrations. Active stirring of the receptor chamber 820 was performed for all experiments.

Figure 58:
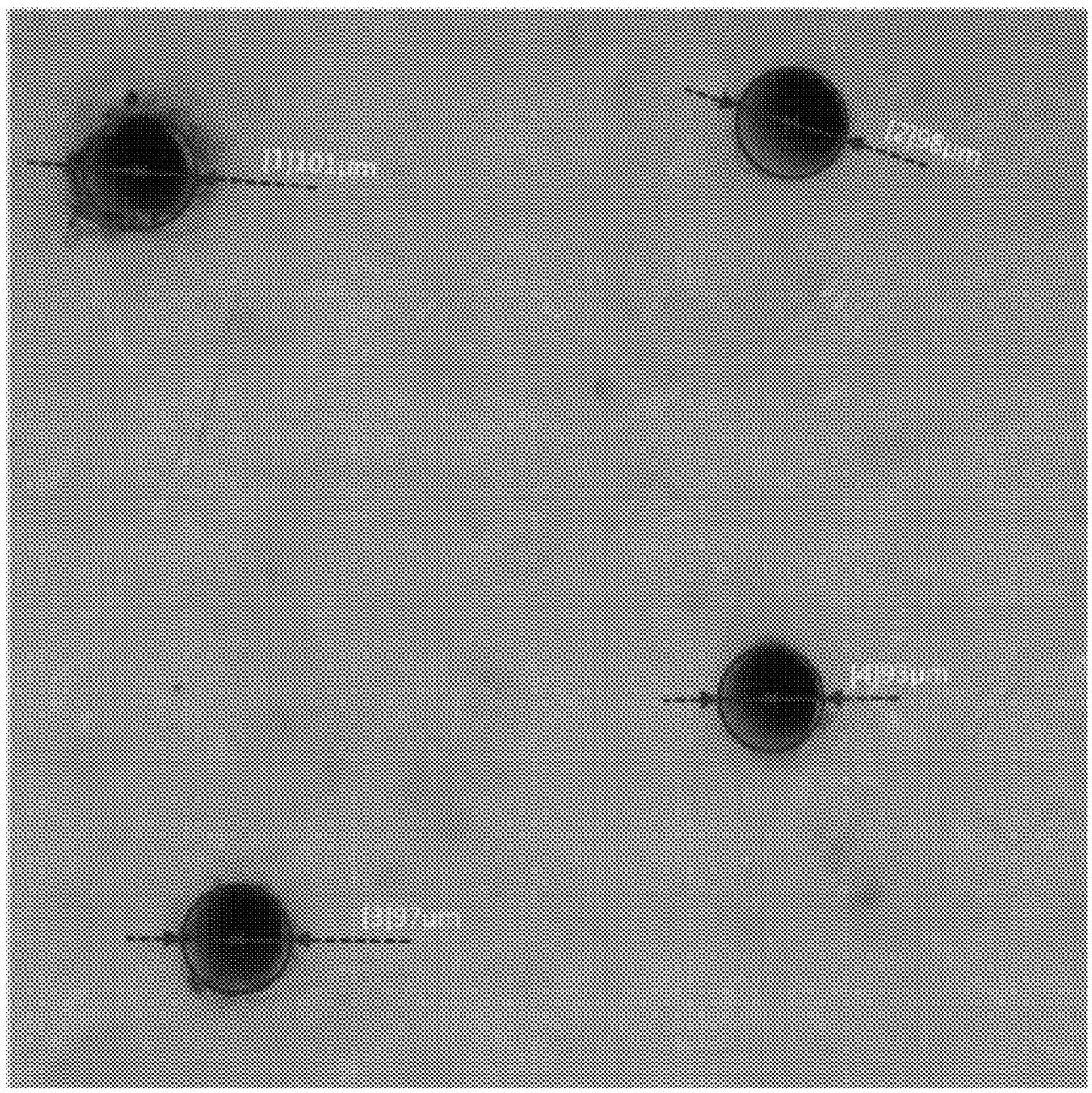
FIGS. 58-59 are enlarged views of perforations in the filter membrane of the diffusion cell apparatus.
Figure 59:
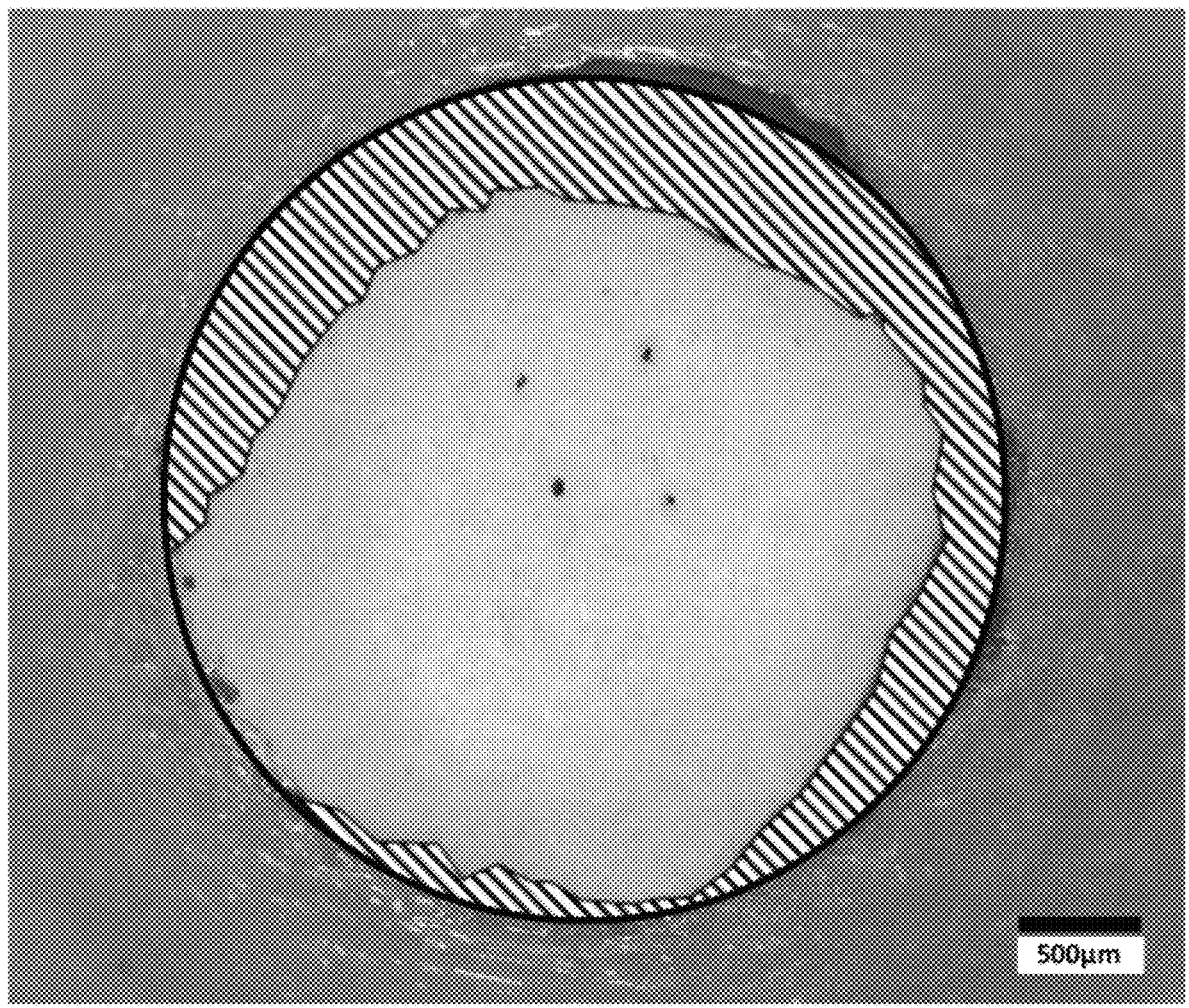

Whatman™ Grade 2 Qualitative Filter Paper with diameter 5.5 cm, thickness 190 μm and pore size 8.0 μm (Whatman Limited, England) was used as an artificial membrane 830 barrier separating the donor and receptor chambers. This filter paper was used as a proxy for anatomical membranes such as the RWM, which experimentally exhibits highly variable thickness and permeability. Using an artificial barrier controlled for pore size as well as membrane thickness. The filter paper was cut to fit a custom 3D-printed diffusion cell adapter, which was circumferentially sealed with general-purpose epoxy. Teflon tape was used to prevent leakage between the 3D-printed adapter and the joint, which were secured with a standard Valia-Chien cell clamp. The filter paper was equilibrated in PBS solution for 30 min prior to any contact with donor substance. Microperforations were introduced in the filter paper with manual application of a stainless steel minutien insect pin with diameter tip of 12.5 μm and diameter shaft of 100 μm and 200 μm (Austerlitz, Czech Republic) under a stereoscopic microscope. Imaging by 3D digital microscope was used to confirm the presence and sizing of perforations in the filter paper (FIG. 58). Original MATLAB code was written to measure the area of the exposed portion of the filter paper barrier, which varied with leakage of epoxy from the diffusion cell adapter (FIG. 59). A summary of all experimental setups, differing by solvent and size and number of perforations, is described in TABLE 2. (Experiments with different characteristics are organized by type (A through H). Perforation area was calculated assuming circular perforations. Average membrane area was calculated using mean data from MATLAB code.)

TABLE 2

| Experiment Type | Solvent | Number of Holes | Perforation Diameter (μm) | Calc. Perf. Area (mm2) | Avg. Membrane Area (mm2) |
|---|---|---|---|---|---|
| A | PBS | 0 | — | — | 7.06 |
| B | PBS | 1 | 100 | $7.854 \times 10^{-3}$ | 8.20 |
| C | PBS | 2 | 100 | $1.571 \times 10^{-2}$ | 7.49 |
| D | PBS | 4 | 100 | $3.142 \times 10^{-2}$ | 8.13 |
| E | PBS | 1 | 200 | $3.142 \times 10^{-2}$ | 9.37 |
| F | 18% P407 | 0 | — | — | 7.33 |
| G | 18% P407 | 4 | 100 | $3.142 \times 10^{-2}$ | 6.63 |
| H | 18% P407 | 1 | 200 | $3.142 \times 10^{-2}$ | 6.59 |

Samples from each time point were analyzed for relative RhoB concentration by detection with fluorescent microscopy. These samples were diluted with PBS by a factor of 10 to prevent gelification of the solution prior to fluorescent microscopy. A 96-well plate containing 13 samples (1 reference sample from the donor chamber and 12 samples from the receptor chamber) was analyzed using a Synergy™ 4 BioTek Multi-Detection Microplate Reader (BioTek, Winooski, VT) with excitation and emission wavelengths set to 554 nm and 590 nm, respectively. Calibration curves were constructed using standards of RhoB concentrations between 0.01 μM and 10.0 μM.

The experiments described above can be modeled mathematically according to equations derived from Fick's second law of diffusion. Combining the equations for unsteady state mass transfer between two chambers and for steady state flux across a membrane leads to an approximate solution for our experiments. This solution holds for thin membrane such as ours where the membrane quickly reaches its steady state condition.

In the steady state condition of the membrane, not to be confused with the steady state condition of the two chambers, the flux across the membrane is proportional to the concentration difference between the two chambers such that $$j_{RhoB} = k_p(C_D - C_R) \tag{2}$$

where $j_{RhoB}$ is the flux at the interface expressed in concentration per area per time [$m^{-2}s^{-1}$], $C_D$, $C_R$ are the RhoB concentrations per volume [$m^{-3}$] in the donor and receptor chambers, respectively, and $k_p$ is the membrane permeance of RhoB in dimensions of velocity [m/s].

The mass balance equations of the Valia-Chien chambers are $$V\frac{dC_D}{dt} = -Aj_{RhoB} \tag{3a}$$

$$V\frac{dC_R}{dt} = +Aj_{RhoB} \tag{3b}$$

where A is the membrane's area and V the volume of each chamber (both the same in our case). Dividing these mass balances by the chambers' volume V, subtracting the two equations, and combining with the flux from Eq. (2) yields a differential equation describing the mass balance between the two chambers $$\frac{d}{dt}(C_D - C_R) = k_p\tilde{\beta}(C_R - C_D) \tag{4}$$

where $$\tilde{\beta} = \frac{2A}{V} \tag{5}$$

with initial condition $$t=0, \ C_D - C_R = C_D^0 - C_R^0 \tag{6}$$

where $C_D^0$ and $C_R^0$ are initial in the donor and receptor chamber, respectively. If the receptor chamber is initially filled with pure solvent, then a is zero.

Integrating the differential equation subject to this condition gives the desired result:

$$\frac{C_D - C_R}{C_D^0 - C_R^0} = \exp(-k_p\tilde{\beta}t) \tag{7}$$

or $$k_p\tilde{\beta}t = \ln\left(\frac{C_D^0 - C_R^0}{C_D - C_R}\right) \tag{8}$$

If we assume that $C_D = C_D^0 - C_R^0$ and $C_R^0 = 0$ then $$k_p \tilde{\beta} t = \ln\left(\frac{C_D^0}{C_D^0 - 2C_R}\right); \tilde{\beta} = \frac{2A}{V}. \quad (9)$$

Thus, the membrane permeance $k_p$ in RhoB is obtained in this case from the slope of the ln $$\left(\frac{C_D^0}{C_D^0 - 2C_R}\right) \text{ vs. } \tilde{\beta} t$$

plot.

The concentration profile versus time is given by $$C_R = \frac{1}{2} C_D^0 [1 - \exp(-k_p \tilde{\beta} t)]. \quad (10)$$

Moreover, for an experiment that does not reach its membrane steady state condition until a known time $t^{ss}$, then the conditions at time $t^{ss}$ are $C^{ss}_D = C0_D - C^{ss}_R$; $C_D = C0_D - C_R$; and $C^{ss}_R$ and $C_R$ are measured. Under these conditions the membrane permeance, $k_p$, can be derived from $$k_p \tilde{\beta} (t - t)^{ss} = \ln\left(\frac{C_D^0 - 2C_R^{ss}}{C_D^0 - 2C_R}\right) \quad (10)$$

and the concentration profile versus time can be obtained from adaptations of the equations above.

A linear mixed model was used to derive membrane permeance, $k_p$, from the slope of $$\ln\left(\frac{C_D^0}{C_D^0 - 2C_R}\right) \text{ versus } \tilde{\beta} t,$$

as defined in Eq. (9) above. The fixed effects were: number of holes (categorical), time, and interactions between numbers of holes and time. A random intercept was included for each experiment run. The interaction between the number of holes and time was examined by using a global likelihood ratio test, comparing the previously mentioned model to one without interaction terms. All permeance values are reported with the standard error derived from the model. A p-value threshold of 0.05 was used for all tests.

Experimentally measured receptor chamber concentration of RhoB for all experiments, normalized by exposed membrane area, is shown in FIGS. 60-63 The maximum concentration of RhoB measured in the receptor chamber at 165 min was 100.1 µM mm$^{-2}$ for experiments using PBS and 10.5 µM mm$^{-2}$ for experiments utilizing P407, corresponding to 9.69% and 0.73% of donor chamber concentration respectively. These concentrations meet the conditions for continuous infinite dosing. It was found that polymer and copolymer drug carriers with temperature dependent liquid-gel transitions often release treatment at a high rate in the initial phases before reaching a steady-state rate of material transfer. This effect is known as burst release. We observed this effect in the initial stages of all P407-based experiments.

To account for the burst release observed in experiments utilizing P407, the data from the first 45 minutes were excluded from the linear mixed models, in accordance with established methods for measuring time of burst release. Predicted concentration curves using these permeance values were then constructed in accordance with Eq. (10) and are shown overlying the experimental data in the above-mentioned FIGS. 60-63.

Permeance values, $k_p$, for all experiments are reported in TABLE 3 with standard error. Two measures of statistical significance are included in the analysis: (1) p-values for the difference in permeance $k_p$ between experiments with perforations and experiments of the same delivery substance without perforations, i.e., p-values* for A versus B through E, and for F versus G and H; (2), p-values for the difference in $k_p$ between experiments of the same delivery substance with different number of perforations but equivalent perforation cross-sectional areas, i.e., p-values** for D versus E, and for G versus H.

TABLE 3

| Experiment Type | Solvent | Number of Holes | Perforation Diameter (µm) | kp (10$^{-6}$ m/s) | p-value* | p-value** |
|---|---|---|---|---|---|---|
| A | PBS | 0 | — | — | — | |
| B | PBS | 1 | 100 | 7.854 × 10$^{-3}$ | 0.037 | |
| C | PBS | 2 | 100 | 1.571 × 10$^{-2}$ | <0.001 | |
| D | PBS | 4 | 100 | 3.142 × 10$^{-2}$ | <0.001 | |
| E | PBS | 1 | 200 | 3.142 × 10$^{-2}$ | <0.001 | } 0.627 |
| F | 18%P407 | 0 | — | — | — | |
| G | 18%P407 | 4 | 100 | 3.142 × 10$^{-2}$ | 0.749 | |
| H | 18%P407 | 1 | 200 | 3.142 × 10$^{-2}$ | <0.001 | } 0.002 |

Experiments Utilizing PBS as Solvent

As shown in TABLE 3, the permeance of RhoB in PBS across an unperforated artificial membrane was 3.04×10$^{-6}$ m s$^{-1}$. The introduction of one or more microperforations was associated with increased permeance of RhoB in PBS across the membrane (p<0.05). The permeance of RhoB in PBS also increased with each additional perforation as well as with greater total perforation cross-sectional area. As hypothesized, there was no difference between the permeance of RhoB in PBS across membranes with equal perforation areas (i.e., four 100 µm perforations and one 200 µm perforation; p=0.627).

Experiments Utilizing P407 as Solvent

The permeance of RhoB in P407 was 2.2×10$^{-7}$ m s$^{-1}$ across an unperforated artificial membrane. This permeance is more than an order of magnitude lower than that of RhoB in PBS (p<0.001). The permeance of RhoB in P407 across a membrane with one 200 µm perforation was 3.0×10$^{-7}$ m s$^{-1}$, which is higher than the permeance in an unperforated membrane (p<0.001). In contrast to experiments in PBS, there was a significant difference between the permeance of RhoB in P407 across membranes with equal perforation areas (i.e. four 100 µm perforations and one 200 µm perforation; p<0.002). Moreover, there is no difference in permeance of RhoB in P407 across a membrane with four 100 µm perforations compared to the absence of perforations (p=0.749).

Figure 60:
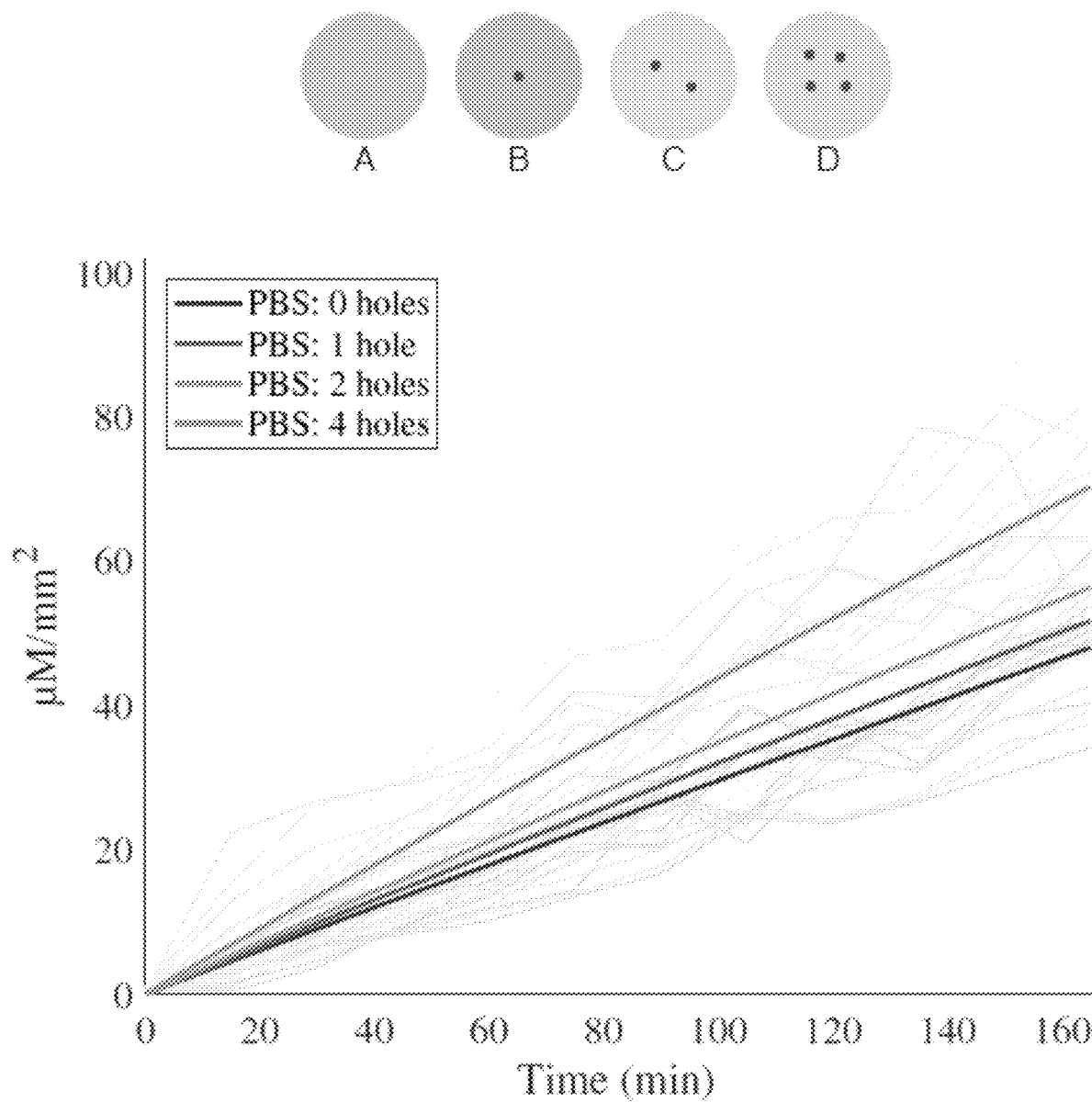
FIGS. 60-61 illustrate predicted and experimental diffusion through the filter membrane of a drug dissolved in saline, as a function of time.
Figure 61:
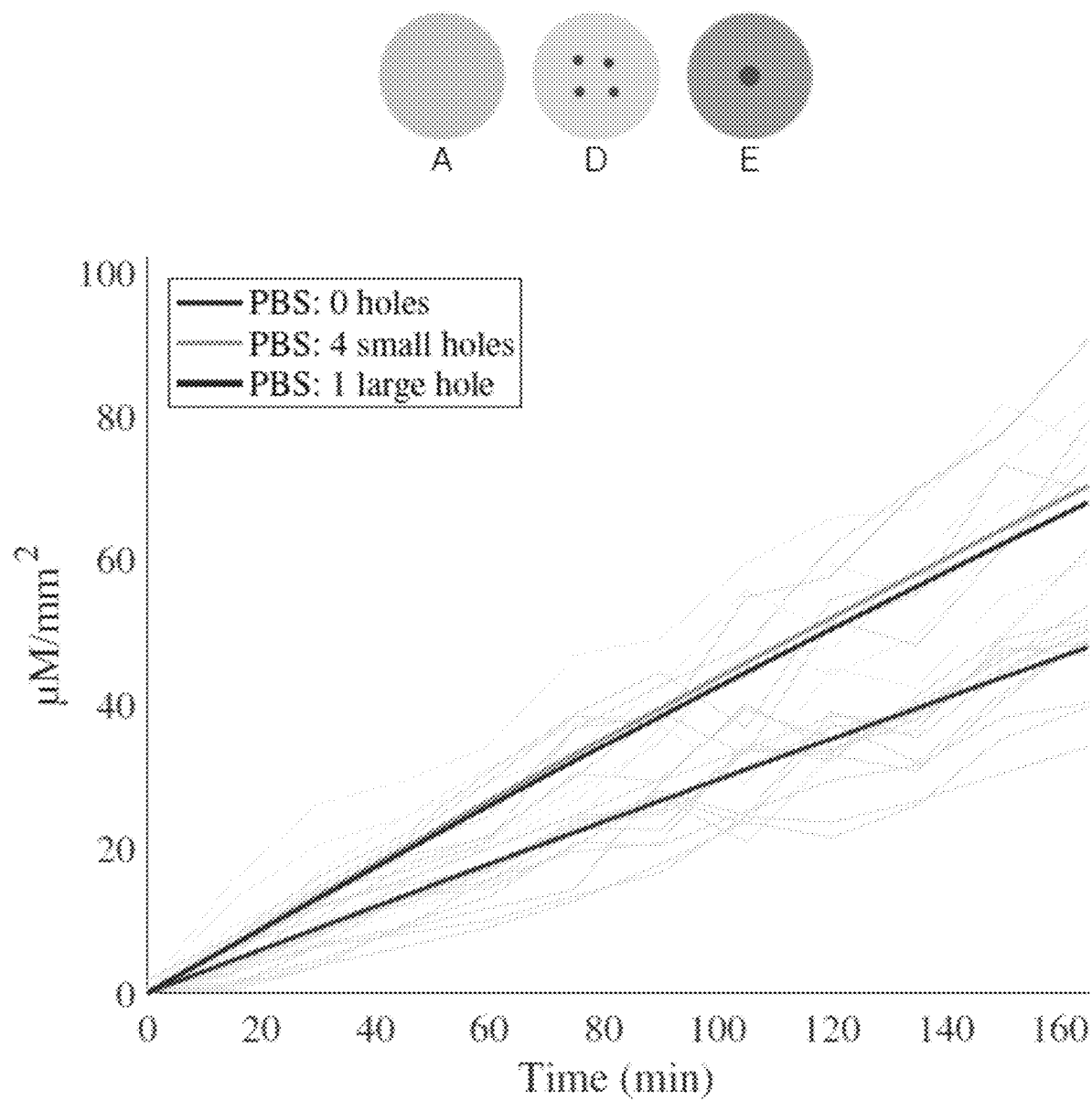

FIGS. 60 and 61 illustrate diffusion of RhoB in PBS. All data is depicted as RhoB concentration in the receptor chamber, normalized by membrane area, as a function of time. Results are coded by experiment type, as indicated by legend and the schematic.

FIG. 60 illustrates predicted concentration profiles for 0, 1, 2 and 4 holes of 100 µm diameter (solid lines), along with raw data (transparent lines). 34 total experiments are represented. In FIG. 60 the first (top) line in the legend and the bottom solid line in the graph represents experiment "A" with 0 holes. The second line in the legend and the third line from the top in the graph represents experiment "B" with 1 hole of 100 μm diameter. The third line in the legend and the second line from the top in the graph represents experiment "C" with 2 holes of 100 μm diameter. The fourth line in the legend and the top line in the graph represents experiment "D" with 4 holes of 100 μm diameter.

FIG. 61 illustrates predicted concentration profiles for experiments utilizing holes with the same total cross sectional area (one hole 200 μm diameter, and four holes 100 μm diameter) in comparison with 0 holes, with raw data. 24 total experiments are represented. In FIG. 61 the first (top) line in the legend and the bottom solid line in the graph represents experiment "A" with 0 holes. The second line in the legend and the top line from the top in the graph represents experiment "D" with 4 holes of 100 μm diameter. The third line in the legend and the second line from the top in the graph represents experiment "E" with 1 holes of 200 μm diameter.

Figure 62:
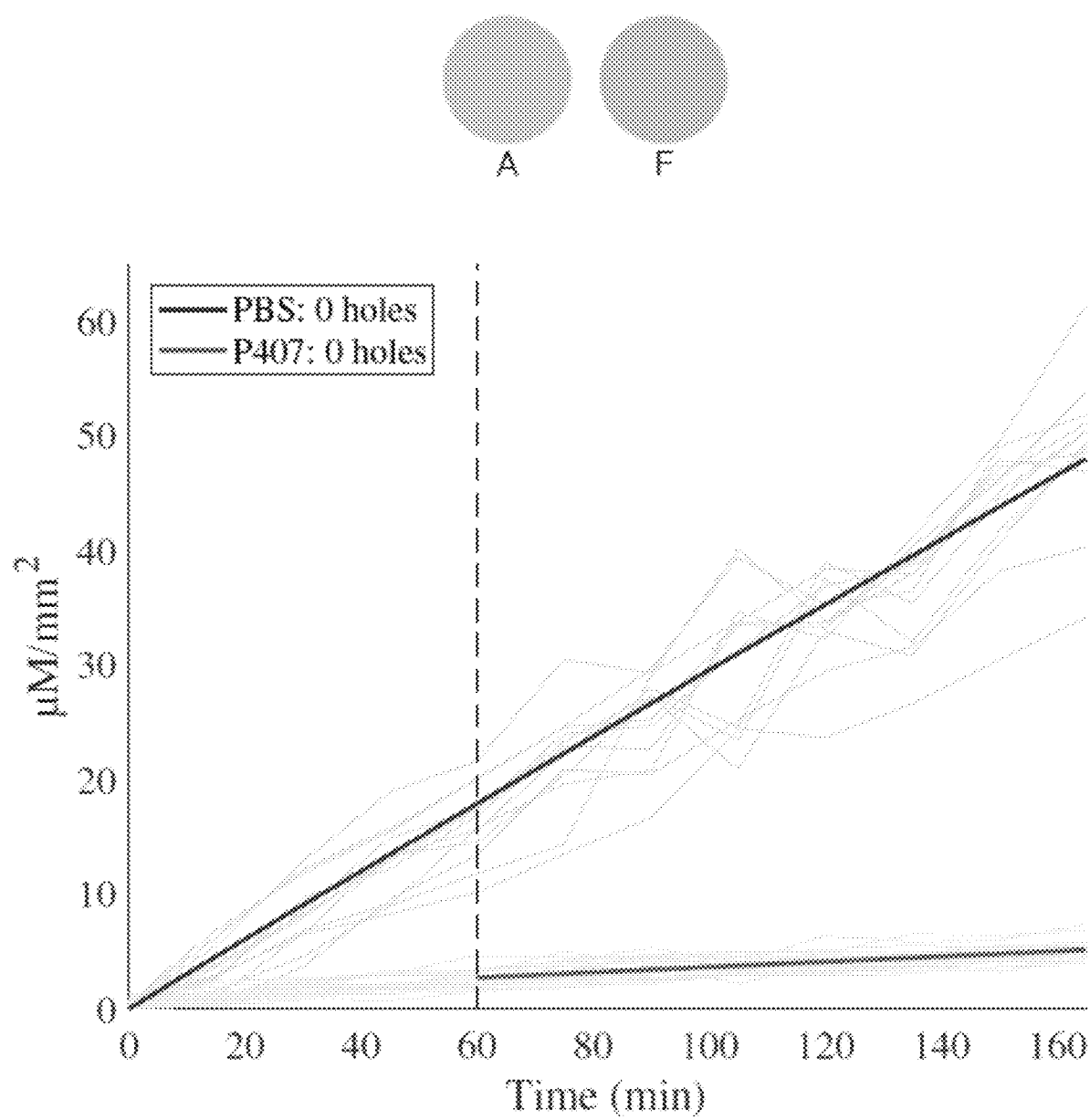
FIGS. 62-63 illustrate predicted and experimental diffusion through the filter membrane of a drug dissolved in P407, as a function of time.
Figure 63:
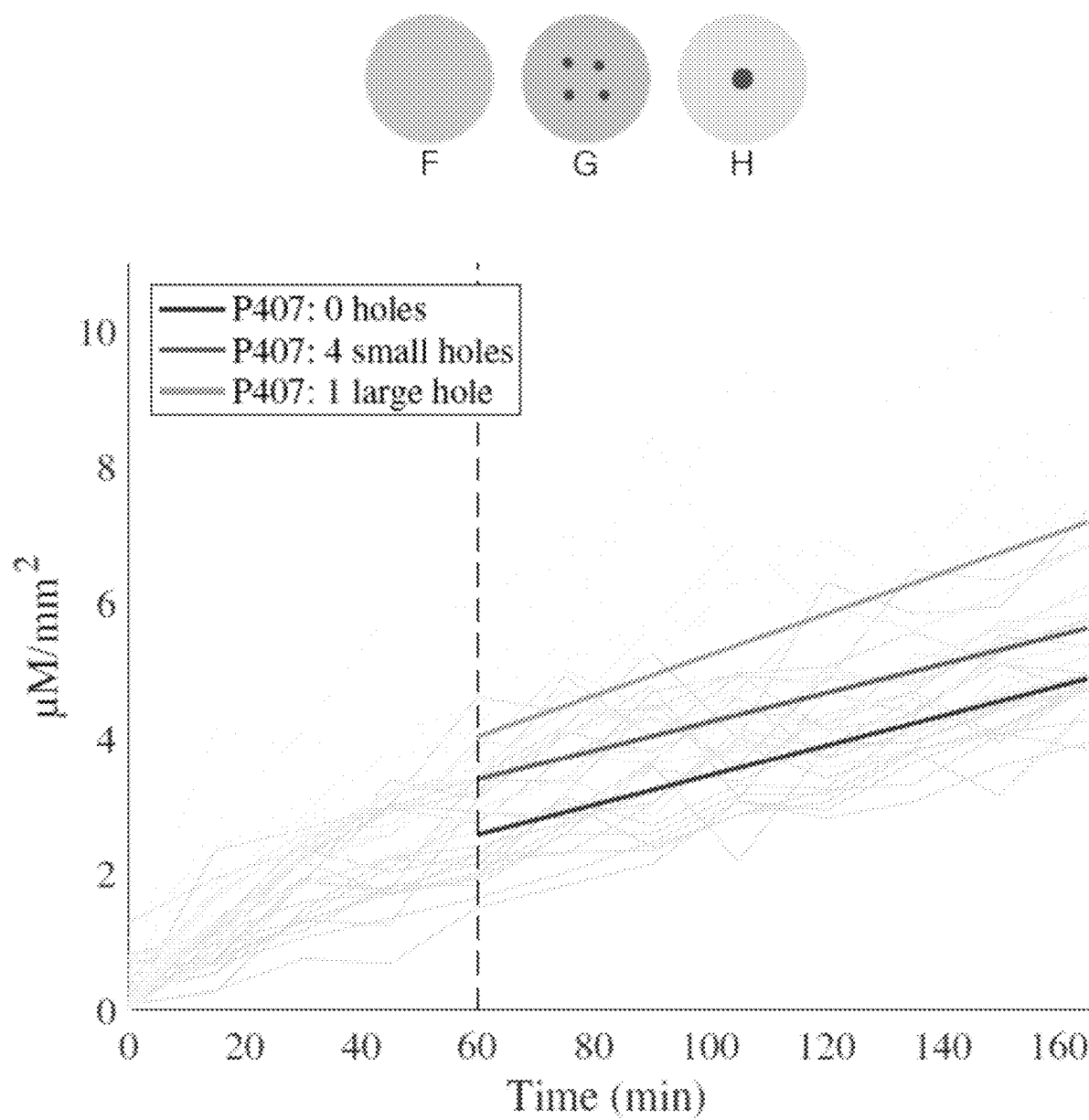

FIGS. 62 and 63 illustrate diffusion of RhoB in P407. All data is depicted as RhoB concentration in the receptor chamber, normalized by membrane area, as a function of time. Results are coded by experiment type, as indicated by legend and schematic.

FIG. 62 illustrates predicted concentration profiles for 0 holes (solid lines), along with raw data shown (transparent lines). 32 total experiments represented. The top line in the legend and the top line in the graph represent experiment "A," diffusion of RhoB in PBS, and the bottom line in the legend and the bottom line in the graph represent experiment "F," diffusion in P407. FIG. 63 illustrates diffusion of RhoB in P407. Predicted concentration profiles for holes with same total cross sectional area (one hole 200 μm diameter, four holes 100 μm diameter) in comparison with 0 holes, in P407 with raw data. 38 total experiments are represented. The first (top) line in the legend and the bottom solid line in the graph represents experiment "F" with 0 holes. The second line in the legend and the second line from the top in the graph represents experiment "G" with 4 holes of 100 μm diameter. The third line in the legend and the top line in the graph represents experiment "H" with one hole of 200 μm diameter.

Using an adapted Valia-Chien cell diffusion system, a standardized and controlled method for studying the permeance of small molecules across thin anatomic barriers was performed, including but not limited to the RWM. Based on prior work, the introduction of multiple microperforations was expected to enhance diffusive transport across the artificial membrane barrier, regardless of solvent (i.e., saline versus P407). The study compared the effects of perforation size and number of perforations on permeance. This experimental question was guided by clinical concerns; large perforations in the RWM can cause leakage of perilymph from the inner ear, although the exact conditions under which this pathology occurs are experimentally unclear. Small perforations, however, are thought to minimize the risk of outward leakage of perilymph. To this end, the study investigated whether many small perforations in the membrane would enhance diffusion to the same degree as one large perforation of equal cross-sectional area.

As expected, in experiments utilizing saline as the solvent for RhoB, an increase in permeance for all perforated membranes was observed, regardless of perforation size or number. Permeance across the membrane also steadily increased with the number of uniformly-sized 100 μm perforations. Of note, no difference in permeance was observed across perforated membranes with equivalent cross-sectional perforation areas. Together, these observations provide a strong basis for predicting diffusion patterns under other conditions. For example, membranes with up to four 100 μm perforations resulted in a 1.5-fold increase in measured permeance. Extrapolation of these results suggest that a three-by-three array of nine perforations representing less than 1% of the total membrane area could more than double the rate of diffusion. This finding—that multiple small perforations can dramatically increase the rate of diffusion across a membrane from a saline reservoir—is highly encouraging for the use of microperforations to enhance diffusive therapy in the ear.

Experiments utilizing P407 gel as the solvent for RhoB demonstrated a different pattern of diffusion. An initial burst release of solute was observed—a behavior that has frequently been documented in studies of therapies delivered by hydrogel carriers. Of note, the introduction of perforations appeared to enhance the effects of burst release. Without being tied to a particular explanation, several explanations are believed applicable for the observed burst release.

Figure 64:
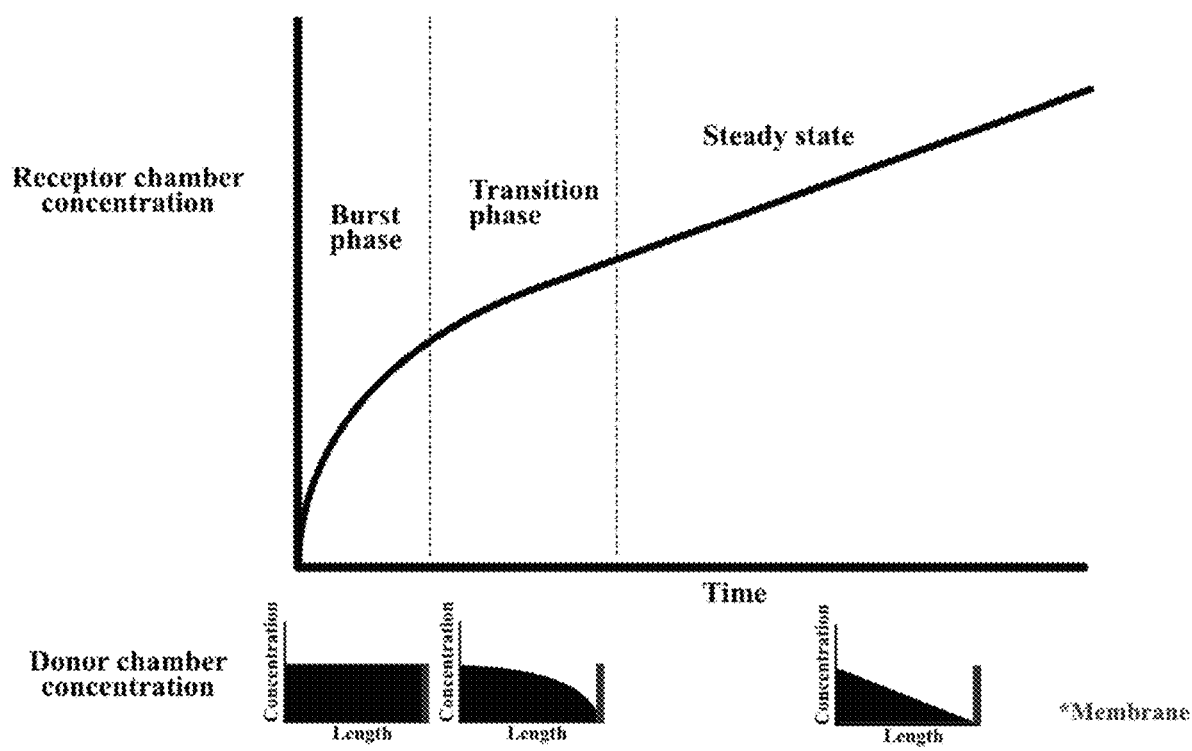
FIG. 64 illustrates receptor chamber concentration through the membrane for a drug dissolved in P407, as function of time. Also illustrated is donor chamber concentration as a function of time.

First, the initial flux of solute across the membrane is high due to a high concentration of solute dissolved uniformly throughout P407. FIG. 64 illustrates phases of burst release in receptor chamber shown with corresponding solute concentrations in donor chamber. Slow movement of solute through P407 in areas far from the membrane causes delayed repletion of areas immediately adjacent to the membrane. This phenomenon results in a concentration gradient in the P407 gel where the concentration of solute is high in areas far from the membrane, and low in areas near the membrane. Eventually, the concentration gradient of solute in P407 is such that the flux across the membrane reaches a steady state. As a result, in the receptor chamber, we observe an initial high rate of diffusion, with a steady decline until the rate of diffusion reaches a steady state. In P407 the donor chamber, a high concentration of solute is dissolved uniformly during initial burst release. During the transition phase, local depletion in the donor chamber occurs in areas near the membrane (vertical line at right side). Afterwards, the flux across the membrane reaches its steady state condition. This phenomenon is likely exacerbated by our inability to stir P407 gel and uniformly disperse the contained solute, unlike in experiments using saline as the solvent.

Second, the initial burst effect is likely compounded by a change in permeance of solute through poloxamer over time due to incomplete setting of the polymer at the start of the experiment. This phenomenon causes immediate release of solute from non-gelified solution (high permeance) and slower release of solute after complete gelification (low permeance).

Overall, the RhoB diffusion rate in P407 after the initial burst release was more than 10 times lower than that in saline. This reduced rate of diffusion and release of solute from P407 has important clinical implications for drug delivery to the inner ear. Current treatment protocols utilizing IT injection require the patient to lie supine for 15 minutes after injection, during which the delivered substance remains in contact with the RWM. Afterwards, the patient sits and the liquid solution delivered with IT is lost via the Eustachian tube. In contrast, P407-based solutions delivered via IT injection reside in the middle ear for one to two weeks, allowing for extended time of drug diffusion. The results suggest that P407 may require approximately two and a half hours to release the same amount of drug released by saline in the clinically mandated 15 minutes. Including the effects of burst release, P407 may require even less time, approximately one and a half hours, to deliver the same amount. Over the one to two weeks that P407 remains in the middle ear, the solution could release 50 times the amount of drug released by saline in 15 minutes; further experimentation is necessary to clarify the role of long-term gelatinous drug carriers for inner ear therapy.

Experiments using P407 as a solvent also demonstrated an unexpected effect of perforations on membrane permeance—while a larger perforation increased the steady state permeance of solute across the membrane, smaller perforations did not have any effect on the steady state rate of diffusion, despite appearing to enhance the initial burst release of RhoB across the membrane. These findings may be explained by diffusion characteristics that are intrinsic to gel-based carriers. For example, the surface tension between the donor P407 gel, the barrier membrane, and the saline within the receptor chamber may prevent diffusion across the system below a critical perforation size. Other interactions between P407 solvent and membrane perforation may also help explain this unexpected finding. Of note, local repletion of solute in the immediate vicinity of a perforation may scale non-linearly with perforation size. Alternatively, using Eq. (2) we can describe the steady state permeance of the total system, $k_t$, using the interactions between various components of the system. In this model of our system, the permeance through solvent, $k_s$, is in parallel with both the permeance across the membrane, $k_m$, excluding the effects of perforations, and the permeance across the perforations, $k_h$, in series, such that $$k_t = \frac{1}{\frac{1}{k_s} + \frac{1}{k_m + k_h}}. \quad (11)$$

Although this model fails to explain why one large perforation would produce different results from four small perforations of equivalent cross-sectional area, it helps to explain why the permeance of solute in P407 with four small perforations is similar to the permeance without perforations: if $k_s \ll k_m + k_h$, then the effects of $k_m + k_h$ are negligible. In this case, $k_t \approx k_s$, so the effects of perforations are smaller when using a solvent with a low permeance such as P407. On the contrary, if $k_s \gg k_m + k_h$, then $k_t \approx k_m + k_h$, so the effects of perforations are larger when using a solvent with higher permeance such as saline. This proposed explanation is consistent with experiments using saline, as described previously. Lastly, it is possible that longer experimental timescales are necessary to compare the permeance of solute in P407 with four small perforations against the permeance without perforations.

Overall, the experiments in saline suggest that multiple small microperforations are an effective means for enhancing saline-based drug diffusion across thin anatomical membranes, while reducing the risk of clinical complications. Meanwhile, the experiments in P407 provide insight into the complexities of hydrogel-based drug delivery with regards to microperforations—specifically that small 100 μm perforations may have little effect on P407-based drug diffusion and that larger perforations are necessary to increase drug diffusion rate. Although larger perforations may increase the risk of fluid leakage, in practice, P407, being a viscous gel, likely forms a seal over the perforations. In guinea pigs, hydrogels including P407 were shown to seal RWM perforations after direct intracochlear injections, leading to significantly increased drug retention. These injections involved smaller perforations of 20-40 μm diameter over the course of 40 minutes; the use of P407 to seal a larger perforation and for longer time periods has not been explored. Therefore, it is important to further investigate the properties of P407 drug delivery when coupled with microperforations, such as the minimum microperforation size needed to enhance drug delivery, the maximum microperforation size allowed for clinical safety, the ability of P407 to seal large perforations, and the rate of perforation healing in vivo.

The experiments show that the diffusion of RhoB in saline solution across an artificial membrane increases with larger total cross-sectional area of microperforations applied to the membrane. The diffusion-enhancing effects of microperforations on gel-based drug delivery are more complex and do not scale with total cross-sectional area of microscopic perforations. Diffusion of RhoB in P407 across an artificial membrane increases with a large perforation, but not with multiple small perforations, perhaps due to diffusion characteristics intrinsic to gel-based drug carriers.

In another aspect, a method of treatment of the inner ear is provided. The method comprises providing a plurality of microperforations in the membrane of the inner ear; and injecting the region adjacent to the microperforations via intratympanic dosing with a drug formulation dissolved in a compound that undergoes gelification at human body temperature.

The plurality of microperforations comprise providing four or more perforations about 100 μm in size. The compound comprises a hydrogel, such as polaxamer 407. The drug formulation comprises gentamicin.

In one embodiment, an apparatus for treating a membrane of the inner ear via intratympanic dosing comprises at least one needle for providing a plurality of microperforations in the membrane; and a drug formulation dissolved in a compound that undergoes gelification at human body temperature. The needle defines an outer diameter of about 100 μm (microns). The membrane in the round window membrane (RWM). The drug is gentamicin. The compound is a hydrogel. The hydrogel comprises poloxamer 407

While the disclosed subject matter is described herein in terms of certain non-limiting exemplary embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments. In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of non-limiting example embodiments of the disclosed subject matter has been presented for purposes of illustration and description. It is not intended to be exhaustive or to limit the disclosed subject matter to those embodiments disclosed herein.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. An apparatus for penetrating an anatomic membrane, comprising:
  a tubular member including a proximal portion, a distal portion, and inner and outer surfaces defining a circumference around the tubular member,
  a plurality of apices extending from a distal end of said tubular member and arranged around the circumference,
  a plurality of valleys arranged around the circumference, wherein each valley adjoins neighboring apices, wherein the plurality of apices and the plurality of valleys define a plurality of serrated blades around the circumference and the plurality of apices and valleys define a circumferential crown shape,
    wherein each of the valleys are configured to include an inside bevel disposed on the inner surface of said tubular member in which the face of the inside bevel is directed toward a central axis of the tubular member, and
    the tubular member being configured to:
    translate between a first position and a different second position upon entering a membrane, and
    extract a portion of the membrane by engaging at least one apex of the plurality of apices with the membrane.

2. The apparatus of claim 1, wherein at least two serrated blades are defined by the plurality of apices and valleys.

3. The apparatus of claim 2, wherein a respective one of the at least two serrated blades includes a wedge configuration.

4. The apparatus of claim 1, wherein the apparatus includes at least eight serrated blades disposed around the circumference of the tubular member.

5. The apparatus of claim 1, wherein each of the plurality of apices includes a tip at a most distal end, and a proximal portion, and further wherein a cutting edge extends proximally from the tip of the respective apex to an edge of an adjacent valley.

6. The apparatus of claim 1, wherein the tubular member is a metallic needle.

7. The apparatus of claim 1, wherein the inside bevel forms a cutting edge.

8. The apparatus of claim 7, wherein the inside bevel includes an inner surface, the inner surface forming an angle of about 15 degrees with a longitudinal axis of the tubular member.

9. The apparatus of claim 1, wherein the tubular member has an outer diameter and inner diameter of about 1 mm (millimeter).

10. The apparatus of claim 1, wherein the tubular member has an inner diameter of about 0.6 mm (millimeter) to about 0.8 mm.

11. The apparatus of claim 1, wherein the tubular member has an outer diameter of about 0.8 to about 1.1 mm (millimeter).

12. The apparatus of claim 1, wherein the distal portion of the tubular member has a length of about 2 mm (millimeter).

13. The apparatus of claim 1, wherein the tubular member further includes a stopper disposed proximal to the distal portion of the tubular member.

14. The apparatus of claim 1, wherein the proximal end of the tubular member is configured to engage a handle.

15. A system for penetrating an anatomic membrane, comprising:
  a tubular member having a proximal portion, a distal portion and a lumen there between, wherein the distal portion includes a plurality of alternating apices and valleys to define a plurality of serrated blades, wherein the distal portion comprises an inside bevel around a circumference of a distal end of the distal portion such that the face of the inside bevel is directed toward a central axis of the tubular member; and
  an aspirator operatively engaged to the tubular member.

16. The system of claim 15, wherein the tubular member includes a stopper coaxially disposed about the tubular member.

17. The system of claim 15, wherein the plurality of alternating apices and valleys define at least two spaced apart serrated blades.

18. The system of claim 15, wherein the serrated blades have a wedge shaped configuration.

19. The system of claim 15, wherein,
  the plurality of apices includes a first apex and a different second apex, the first apex and the second apex are spaced apart from each other with a respective valley of the plurality of valley in between the first apex and the second apex.

* * * * *